US006479274B1

(12) United States Patent
Antalis et al.

(10) Patent No.: US 6,479,274 B1
(45) Date of Patent: Nov. 12, 2002

(54) DNA MOLECULES ENCODING HUMAN HELA2 OR TESTISIN SERINE PROTEINASES

(75) Inventors: Toni Marie Antalis, Toowong; John David Hooper, Herston, both of (AU)

(73) Assignee: Amrad Operations Pty., Ltd., Victoria (AU)

( * ) Notice: Subject to any disclaimer, the term of this patent is extended or adjusted under 35 U.S.C. 154(b) by 0 days.

(21) Appl. No.: 09/023,942

(22) Filed: Feb. 13, 1998

(30) Foreign Application Priority Data

Feb. 13, 1997 (AU) .............................................. PO5101
Nov. 18, 1997 (AU) .............................................. PP0422

(51) Int. Cl.$^7$ .......................... C12N 1/20; C12N 15/00; C12N 5/00; C12N 9/50; C07H 21/04
(52) U.S. Cl. .............................. 435/252.3; 435/252.33; 435/432.5; 435/320.1; 435/219; 536/23.2
(58) Field of Search ...................... 536/23.2; 435/252.3, 435/320.1, 325, 219, 252.33

(56) References Cited

PUBLICATIONS

Beaubien et al., Biochemistry, 30, 1628–1635, Feb. 1991.*
genbank–est111, accession No. AA161187, Dec. 1996.*
E. Vey et al. (1996) "Expression and Creavage of Tumor . . . Cell Lines Upon Direct Contact With Stimulated T Cells" *Eur. J. Imm.* 26:2404–2409.
Y. Nakabo and M.J. Pabst (1996) "Lysis of Leukemic Cells By Human Macrophages: Inhibition by 4–(2–2–aminoethyl)–benzenesulfonyl Flouride (AEBSF) . . . " *J. Leukocyte Biol.* 60:328–336.
D.J. McConkey (1996) "Calcium–dependent, Interleukin 1 converting Enzyme Inhibitor–insensitive Degradation of Lamin B1 . . . " *J. Biol. Chem.* 271:22398–22406.

S.S. Choi et al. (1996) "Prostaglandin–E2 Regulation of Tumor Necrosis Factor Receptor Release in Human Monocytic THP–1 Cells" *Cellular Immunology* 170:178–184.
N. Arese et al. (1994) "Involvement of a Serine Protease in the Synthesis of Platelet–activating by Endothelial Cells Stimulated By Tumor Necrosis . . . " *Eur. J. Immunol.* 24:3131–3139.
J.L. Dickinson et al. (1995) "Plasminogen Activator Inhibitor Type 2 Inhibits Tumor Necrosis Factor –induced Apoptosis" *The Journal of Biological Chemistry* 270 (46):27894–27904.
R. Sood et al. (1997) "Construction of a 1–Mb Restriction–mapped Cosmid Contig Containing the Candidate Region for the Familial Mediterranean Fever Locus . . . " *Genomics* 42:83–95.
N.A. Doggett et al. (1995) "An Integrated Physical Map of Human Chromosome 16" *Nature 377* (28):335–365.
L.E. Sower et al. (1996) "Short Communication: Extracellular Activities of Human Granzymes . . . " *Cellular Immunology* 171:159–163.

* cited by examiner

Primary Examiner—Rebecca E. Prouty
Assistant Examiner—Maryam Monshipouri
(74) Attorney, Agent, or Firm—Scully, Scott, Murphy & Presser

(57) ABSTRACT

The present invention related generally to novel molecules and more particularly novel proteinaceous molecules involved in or associated with regulation of cell activities and/or viability. The present invention is particularly directed to novel serine proteinases and a novel kinase and to derivatives, agonists and antagonists thereof. In one embodiment, the present invention provides a novel serine proteinase, referred to herein as "HELA2" or "testisin", which has roles in spermatogenesis, in suppressing testicular cancer and as a marker for cancers.

10 Claims, 62 Drawing Sheets

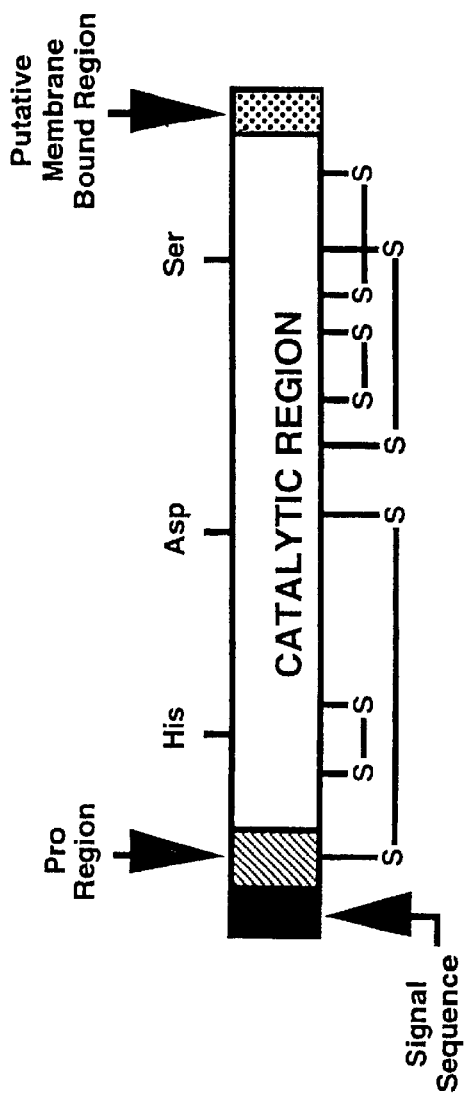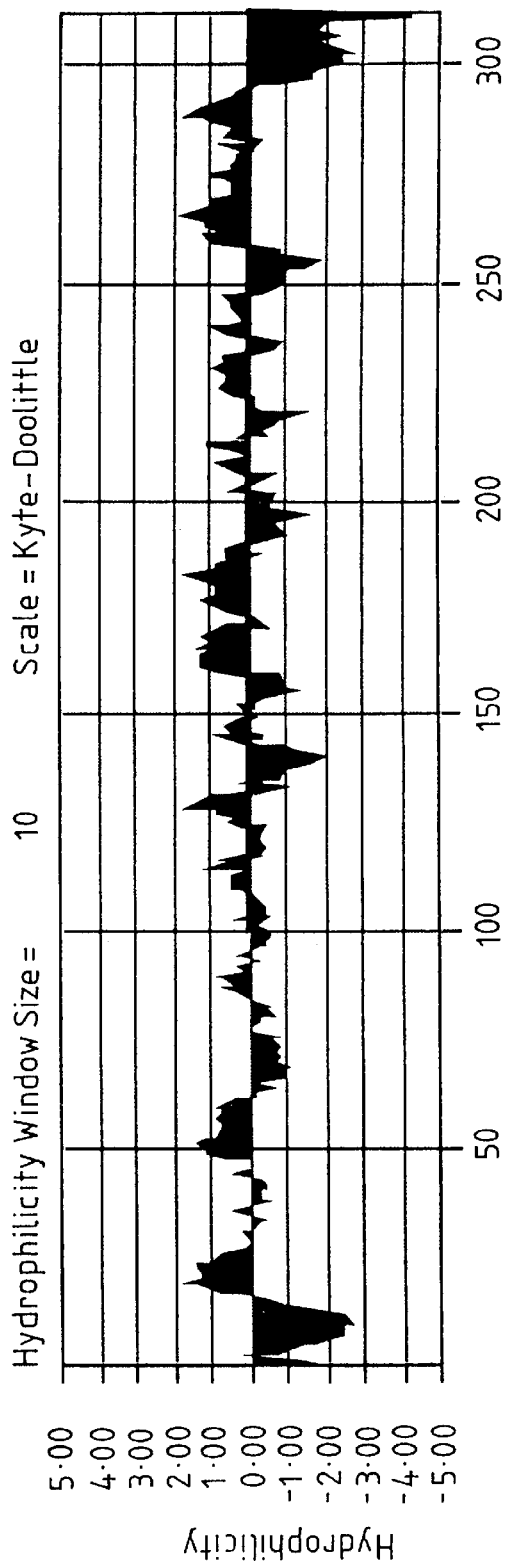
FIG 1

FIG 2A

| FIG 2A(I) | FIG 2A(II) |
|---|---|

Sequence comparison of HELA2(Testisin) and prostasin

```
                   Signal sequence              Light Chain
prostasin  MAQKGVLGPGQLGAVAILLYLGLLRSGTGAEGA--EAPCG-VAPQARITGGSSAVA
HELA2      MGARGAL----L--LALLLARAGLRKPESQEAAPLSGPCGRRVITSRIVGGEDAEL
           *  . *      *    * *** *      * .      * *       *** *
                                                    ASP
                                                     *
prostasin  KVSTLKDIIPHPSYLQEGSQGDIALLQLSRPITFSRYIRPICLPAANASFPNGLHC
HELA2      TRYFVSNIYLSPRYLG-NSPYDIALVKLSAPVTYTKHIQPICLQASTFEFENRTDC
              .   *       . .  ****..**.* *..:: :**** *:   *   *
                                          S-S                  N-gly
                                                                *
                            SER
                             *
prostasin  ACGGDSGGPLSCPVEGLWYLTGIVSWGDACGARNRPGVYTLASSYASWIQSKVTEL
HELA2      ACFGDSGGPLACNKDGLWYQIGVVSWGVGCGRPNRPGVYTNISHHFEWIQ-----
           ** ******* *   **** *.:**** .**  ******* .* : ***
                                         S-S                N-gly
```

FIG 2A(I)

Sequence comparison of HELA2(Testisin) and prostasin

```
                                                HIS
                                                 *
prostasin   GQWPWQVSITYEGVHVCGGSLVSEQWVLSAAHCFPSEHHK-EAYEVKLG----AHQLDSYSEDA
HELA2       GRWPWQGSLRLWDSHVCGVSLLLSHRWALTAAHCFETDLSDPSGWMVQFGQLTSMPSFWSLQAYY
            * ****  *   * ***** ** **   * **** * *  *                *
                              └──S-S──┘                    YS
                                                        (Long Isoform)
                              Heavy Chain prostasin   TVTGWGHVAPSVSLLTPKPLQQLEVPLISRETCNCLYNIDAKPEEPHFVQEDMVCAGYVEGGKD
HELA2       WVTGWGYIKEDEALPSPHTLQEVQVAIINNSMCNHLFLKYSFRKD--IFG-DMVCAGNAQGGKD
             ****          * *  ****    *     * **    *    *  ******  ****
                                        N-gly
                                         └──S-S──┘

┌─Putative──────────┐
                                                   │ Transmembrane     │
                                                   │ Domain            │
prostasin   QPRVVPQTQESQPDSNLCGSHLAFSSAPAQGLLR      │PILFLPLGLALGLLSPWL │  SEH
HELA2       --KLMAQSGMSQPD-----------PS----W        │PLLFFPLLWALPLLGPV  │
              *    *  * *           *    *         │ * ** *  *** *  * │   *
                                                   └───────────────────┘
```

FIG 2A(II)

In vitro transcription / translation of HELA2 (Testisin)

FIG 3(iii)

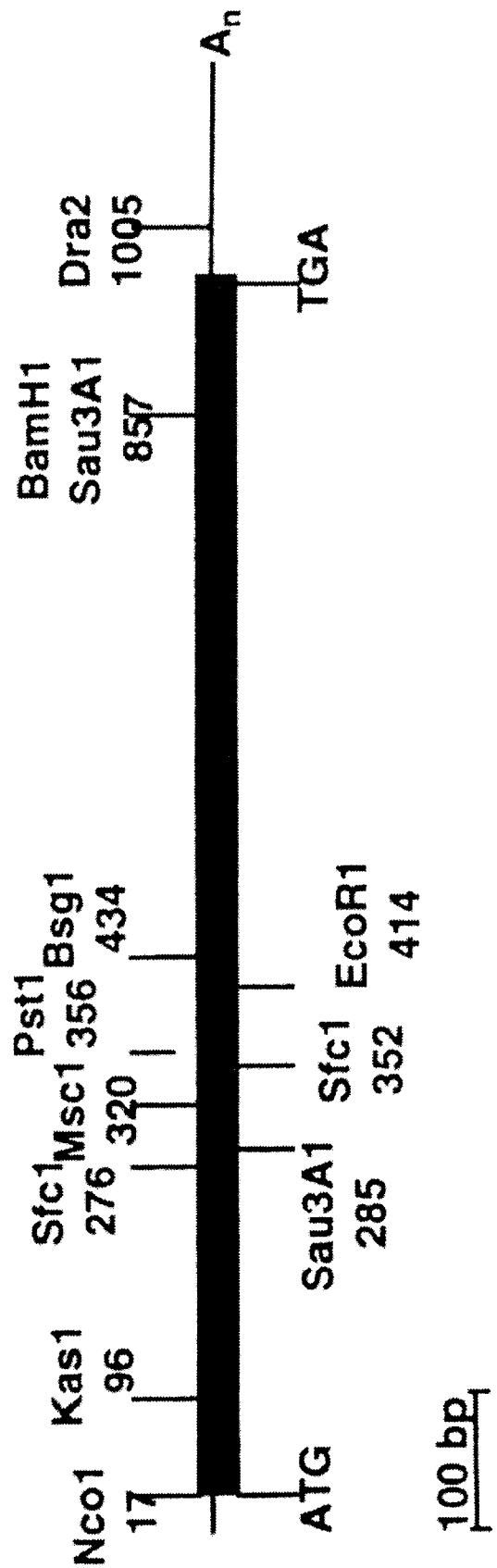
FIG 3(iii)

FIG 4(iii)

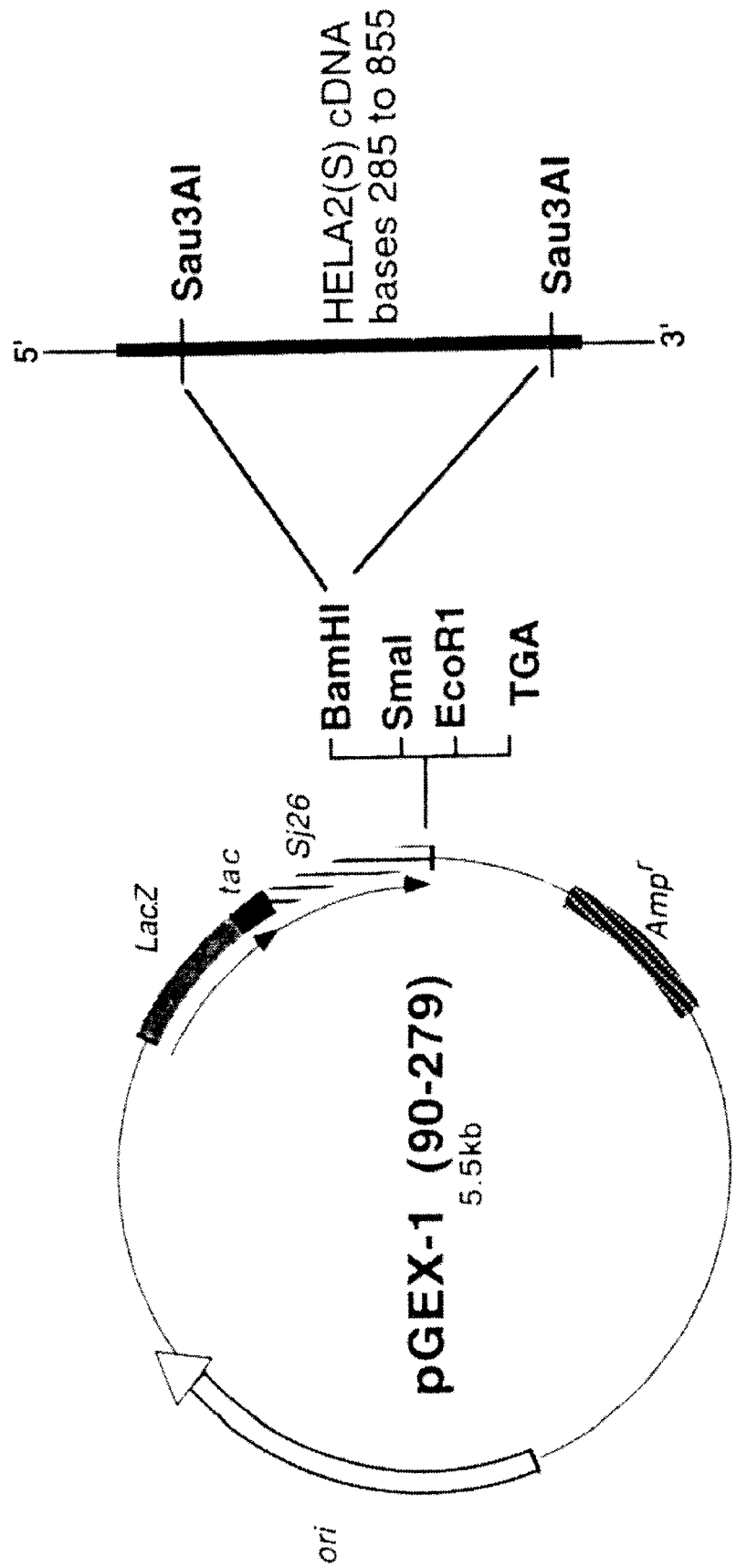
FIG 4(iii)

FIG 5
A. Expression of recombinant Testisin in E. coli.
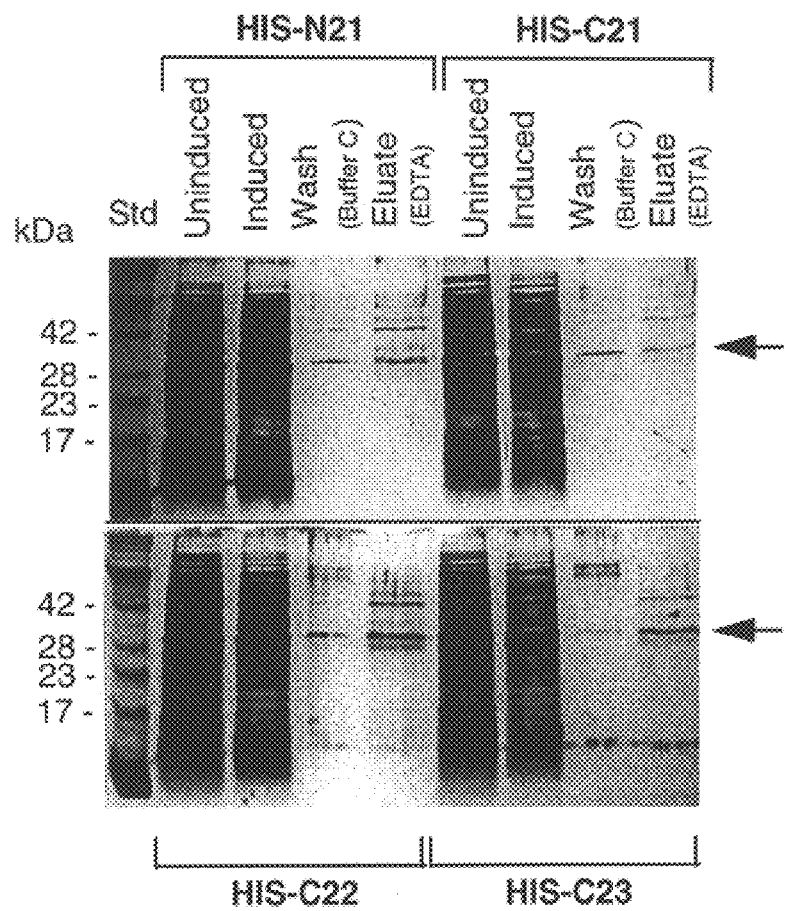
B. Western blot of recombinant Testisin
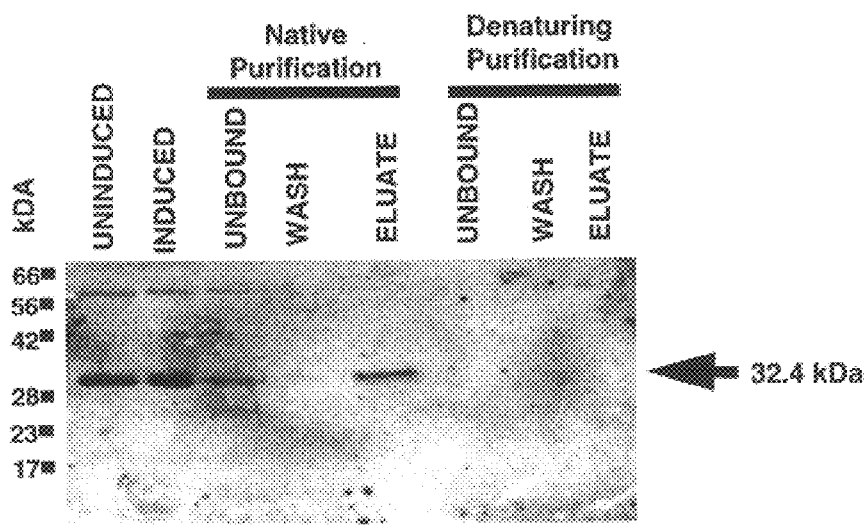

FIG 6(III)

```
1                                            GCCCGGGGAGAGGAGGCC
19   ATGGGCGCGCGGGGCGCTGCTGCTGCTGGCTCGGGCTGGACTCAGGAAG
     M  G  A  R  G  A  L  L  L  L  A  R  A  G  L  R  K      20

79   CCGGAGTCGCAGGAGGGCGCCGTTATCAGGACCATGCGGCCGACGGTCATCACGTCG
     P  E  S  Q  E  A  A  P  L  S  G  P  C  G  R  R  V  I  T  S     40

139  CGCATCGTGTGGGGTGGAGAGGACGCCGAACTCGGGCGTTGGCCGTGGCAGGGAGCCTGCGC
     R  I  V  G  G  E  D  A  E  L  G  R  W  P  W  Q  G  S  L  R     60

199  CTGTGGGATTCCCACGTATGCGGAGTGCGCTCAGCGAGCCTGCTCAGCCACCGGCG
     L  W  D  S  H  V  C  G  V  S  L  L  S  H  R  W  A  L  T  A     80

259  GCGCACTGCTTTGAAACCTATAGTGACCTTAGTGATCCCTCCGGGTGGATGGTCCAGTTT
     A  H  C  F  E  T  Y  S  D  L  S  D  P  S  G  W  M  V  Q  F    100

319  GGCCAGCTGACTTCCATGCCAAGCTTCTGGAGCCTGCAGGCCTACTACACCCGTTACTTC
     G  Q  L  T  S  M  P  S  F  W  S  L  Q  A  Y  Y  T  R  Y  F    120

379  GTATCGAATATCTATCTGAGCCCTCGCTACCTGGGGAATTCACCCTATGACATTGCCTTG
     V  S  N  I  Y  L  S  P  R  Y  L  G  N  S  P  Y  D  I  A  L    140
```

FIGURE 6 (II)

```
439 GTGAAGCTGTCTGCACCTGTCACCTACACTAAACACATCCAGCCCATCTGTCTCCAGGCC
      V  K  L  S  A  P  V  T  Y  T  K  H  I  Q  P  I  C  L  Q  A   160

499 TCCACATTTGAGTTTGAGAACCGGACAGACTGCTGGGTGACTGGCTGGGGGTACATCAAA
      S  T  F  E  F  E  N  R  T  D  C  W  V  T  G  W  G  Y  I  K   180

559 GAGGATGAGGCACTGCCATCTCCCCACACCCTCCAGGAAGTTCAGGTCGCCATCATAAAC
      E  D  E  A  L  P  S  P  H  T  L  Q  E  V  Q  V  A  I  I  N   200

619 AACTCTATGTGCAACCACTCTTCCTCAAGTACAGTTTCCGCAAGGACATCTTTGGAGAC
      N  S  M  C  N  H  L  F  L  K  Y  S  F  R  K  D  I  F  G  D   220

679 ATGGTTTGTGCTGGCAATGCCCAAGGCGGGAAGGATGCCTGCTTCGGTGACTCAGGTGGA
      M  V  C  A  G  N  A  Q  G  G  K  D  A  C  F  G  D  S  G  G   240

739 CCCTTGGCCCTGTAACAAGAATGGACTGTGGTATCAGATTGGAGTCGTGAGCTGGGGAGTG
      P  L  A  C  N  K  N  G  L  W  Y  Q  I  G  V  V  S  W  G  V   260

799 GGCTGTGGTCGGCCCAATCGGCCCGGTGTCTACACCAATATCAGCCACCACTTTGAGTGG
      G  C  G  R  P  N  R  P  G  V  Y  T  N  I  S  H  H  F  E  W   280
```

FIGURE 6 (III)

```
859  ATCCAGAAGCTGATGGCCCAGAGTGGCATGTCCCAGCCAGACCCCTCCTGGCCGCTACTC
      I  Q  K  L  M  A  Q  S  G  M  S  Q  P  D  P  S  W  P  L  L   300

919  TTTTTCCCTCTCTTCTCTGGGCTCTCCCACTCCTCCTGGGGCCGGTCTGAGCCTACCTGAGCCCA  314
      F  F  P  L  L  W  A  L  P  L  L  G  P  V  *

979  TGCAGCCTGGGCCACTGCCAAGTCAGGCCCTGTTCTCTTCTTGTCTTTGTTTGGTAATAA
1039 ACACATTCCAGTTGATGCCTTGCAGGGCATTCTTCAAAAAAAAAAAAAAAAAAAAAAA
1099 AAAAAAAAAAAAAAAAAA
```

FIG 8(iii)

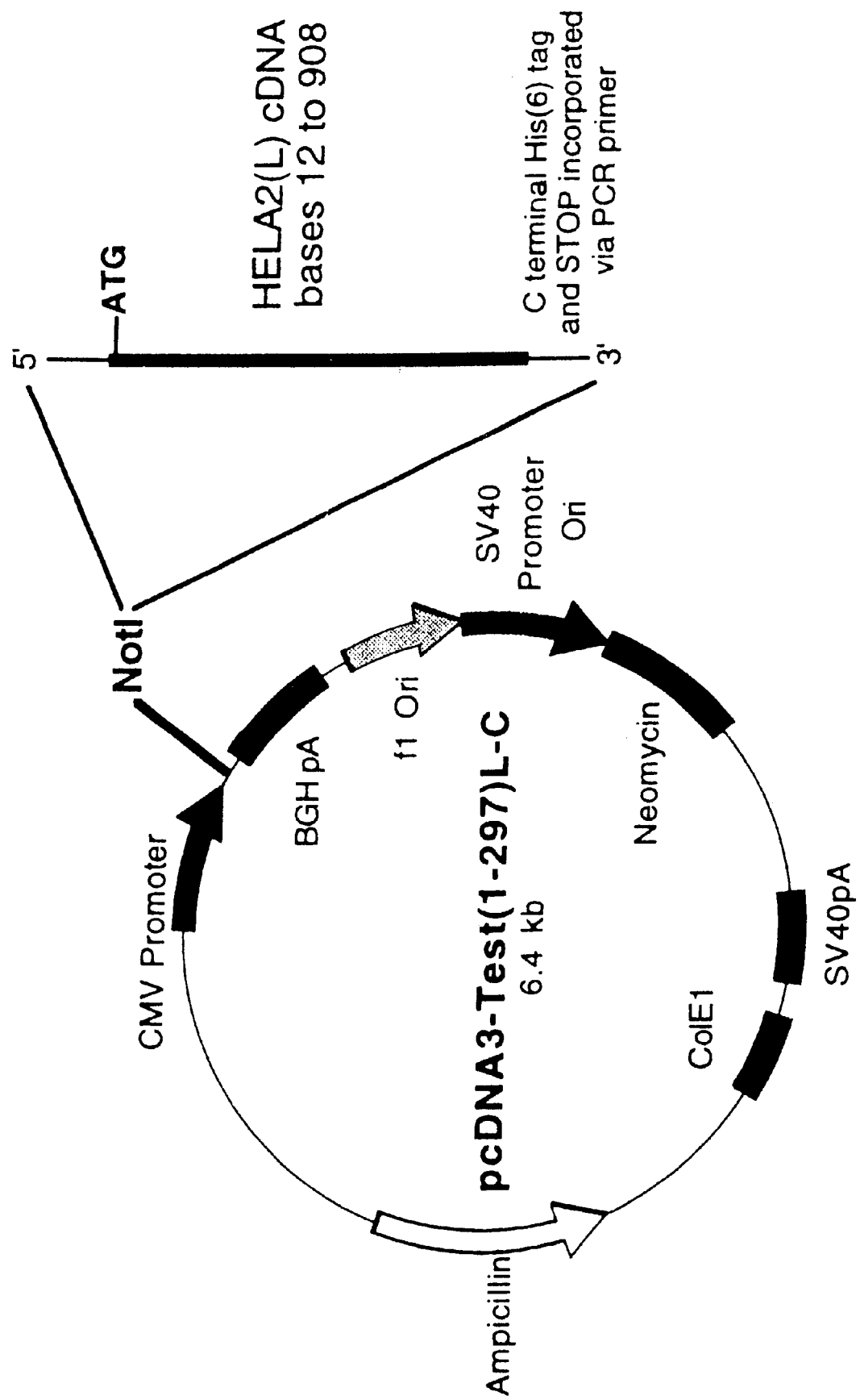
FIG 8(iii)

FIG 9

| FIG 9(i) | FIG 9(ii) |
|---|---|
| FIG 9(iii) | FIG 9(iv) |

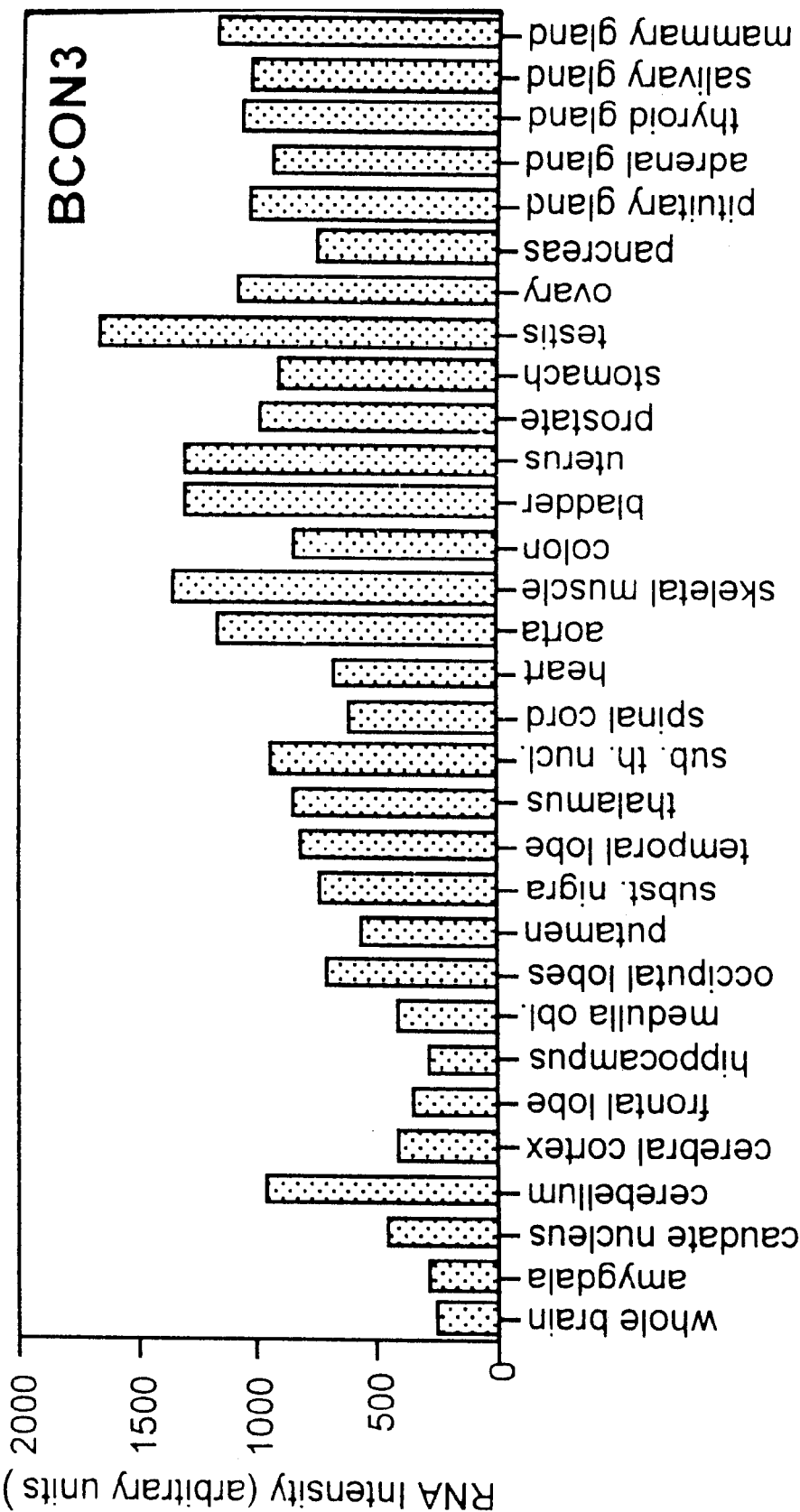
FIG 9(iii)

FIG 14
A. Northern Blot
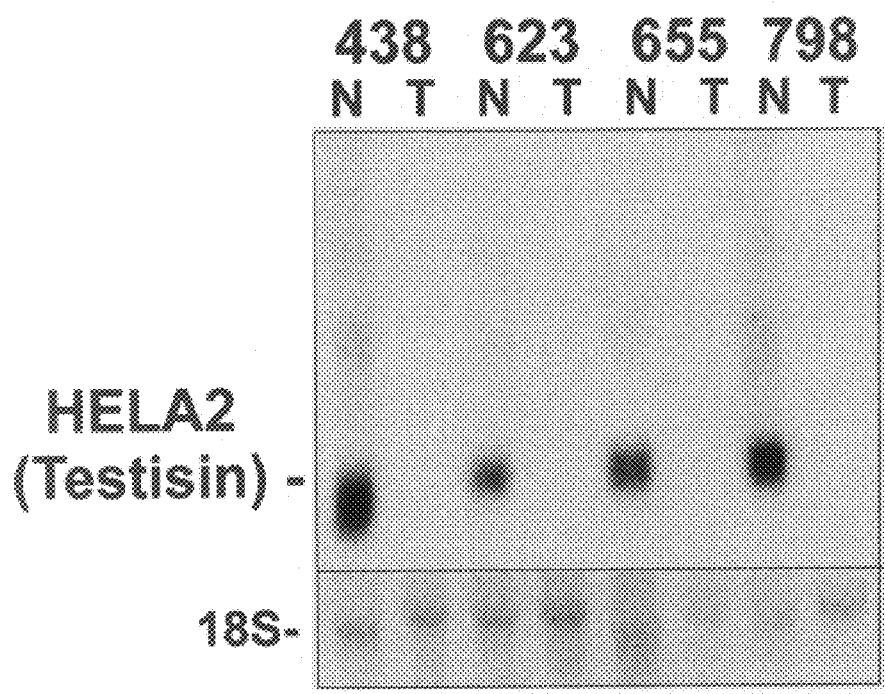
B. Immunohistochemistry
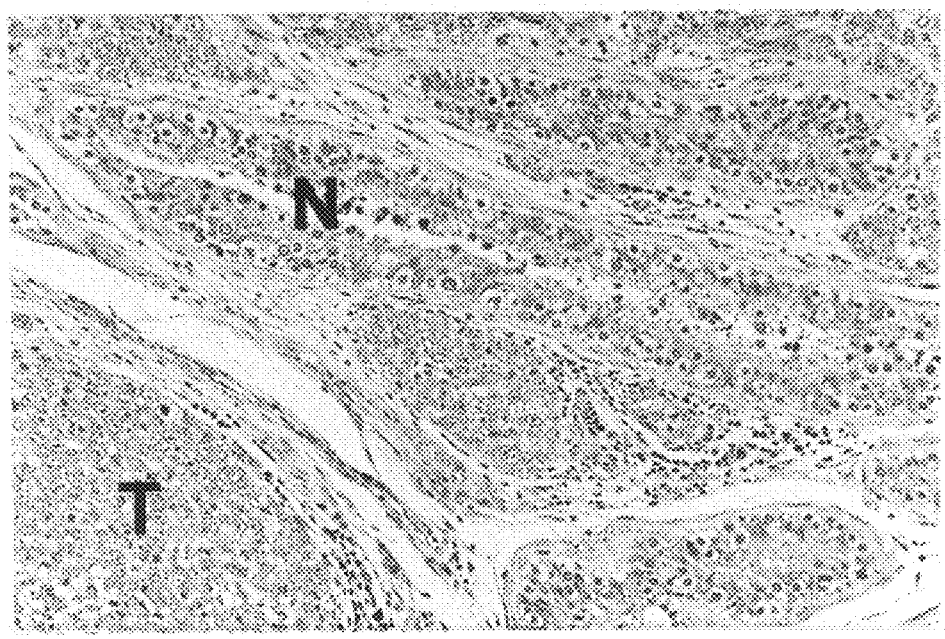

FIG 16(iii)

```
agtgagtctc ctgcctcagc ctcccaagta gctgggactt caggtgtgtg        50
ccaccatcct cagctaattt tttttttttt tttttttttg agaaggagtc       100
ttgctctgtc gcccaggctg gagtgcagtg gcgcgatctt ccaggcccca       150
ccgggccctc aggaaggcct tgcctacctg ctttaagggg actcctggct       200
cagggccagg cccctggtgc tggaggaggt ggtgggtgga gggcaggggg       250
caccaagcgg gcagccagga cccccgggct gcagacaaga aaaggactgt       300
                      /+1...EXON 1....
gggtccacc gggtctgggc CACATCAAGG AATGTGGTTG AAGACCCGCC        350
CTTAGGAGCT GAAAGCCAGG GCGCTACCAG GCCTGAGAGG CCCCAAACAG       400
CCCTTGGCC TGGTTTGGGA GGATTAAGCT GGAGCTCCCA ACCCGCCCTG       450
CCCCAGGGG GCGACCCCGG GCCCGGCGCG AGAGGAGGCA GAGGGGCGT        500
CAGGCCGCGG GAGAGGAGGC CATGGGCGCG CGCGGGGCGC TGCTGCTGGC       550
                                        /INTRON A....
GCTGCTGCTG GCTCGGGCTG GACTCAGGAA GCCGgtgag ctcggggcgc       600
tgctggcggg atggggaggc gggggagcgg tggggaggac gggaggtgga       650
```

FIG 16(i)

```
                                                                        /EXON 2...
ggccgcgggg  agtcacttct  tgtctcccgc  agAGTCGCCAG  GAGGCGGCGC    700
            /INTRON B...
CGTTATCAGg  tagggcgccc  aggacgcgcg  attcctgcca   gggccgttgg    750
gccgaggtgg  acgggggggcg gtgagggggt  agagggggggc  ctttactgct    800
ctctcgcccc  cgccccccggg atcgagaact  ctgttggcgt   ggaaagtaac    850
taacggacgc  tggagggga   tgggcggggcc ctgcagagca   cgtgggagga    900
tctccagtgt  cacctacttc  ctgctgcaca  cacgcgaggg   gaccctgggt    950
gggcaaaaac  gtgctttccc  ggacggggtt  gaaggggaga   aagggagagg    1000
tcgggcttgg  ggggctgcct  cccgcggctc  agcagttcct   ctgaccatcc    1050
    /EXON 3...
gagGACCATG  CGGCCGACGG  GTCATCACGT  CGCGCATCGT   GGGTGGAGAG    1100
GACGCCGAAC  TCGGGCCGTTG GCCGTGGCAG  GGGAGCCTGC   GCCTGTGGGA    1150
TTCCCACGTA  TGCGGAGTGA  GCCTGCTCAG  CCACCGCTGG   GCACTCACGG    1200
```

FIG 16(ii)

```
                                   /INTRON C...
CGGCGCACTG  CTTTGAAACg  tgagtggggg  tgcgaacgga  ggggtgcggg   1250
gacgggcagg  aacagggctg  gagggagtgc  caccgaactt  tacctctggt   1300
ctgatgccag  acttgggcgt  gaaagttgtg  cgtggatgcg  gcctggtgtt   1350
ctcctgagcc  ccaggctgtg  ctgcagccgg  ttacacccac  tccagttccc   1400
tttgggtctc  ctggagggaa  ccctgttcag  gttattccag  aatgttcttc   1450
cagaacattt  ccacacactt  ttgggtattc  tctcccttttt tctttcaacc   1500
caaagttcac  cactgaccat  cccaccctca  tcccccctcc  tggtggacgg   1550
tgcgggtacag tgtggggcac  tgagccaagg  ccagcacccc  cgggccgctg   1600
tgtggactcc  atcctgccaa  tcccacattg  gcgtggtgca  tctccccatt   1650
cctccttggg  ctgcatgggg  gtgccctgg   aggccttggc  tcaatgcaag   1700
gctccttggg  acagctctgg  gaggtgacaa  gaccccaccc  ttctgctgca   1750
ggagcaggtc  ctaggacttt  ggttgtggtc  tgtctgggct  ccttcatttc   1800
tgcagggac   cctgggtgtt  agcaagtagc  agcaacacca  cagtttcccc   1850
tcctgcactg  gacccagtt   gtgctcaggt  agccagcct   ccatccaggg   1900
```

FIG 16(iii)

```
                                                          /EXON 4....
ccctgactg   ctctcttctc   ttctgccagc   tatagTGACC   TTAGTGATCC    1950
CTCCGGGTGG  ATGGTCCAGT   TTGGCCAGCT   GACTTCCATG   CCATCCTTCT    2000
GGAGCCTGCA  GGCCTACTAC   ACCCGTTACT   TCGTATCGAA   TATCTATCTG    2050
AGCCCTCGCT  ACCTGGGGAA   TTCACCCTAT   GACATTGCCT   TGGTGAAGCT    2100
GTCTGCACCT  GTCACCTACA   CTAAACACAT   CCAGCCCCATC  TGTCTCCAGG    2150
CCTCCACATT  TGAGTTTGAG   AACCGGACAG   ACTGCTGGGT   GACTGGCTGG    2200
                                      /INTRON D....
GGGTACATCA  AAGAGGATGA   GGtgagggct   gggacaggc    gggtcaggga    2250
ggaactgtct  ttgttcacct   gttccctgc    ataggcacaa   tagcccctg     2300
cttggtctgg  gggtgcaggc   tatgccctc    ttgcttgcag   tctctcctca    2350
cctgccaggg  cagggaccaa   acacccagtt   ctctccttc    caggggctgt    2400
gggggccaga  aggagagtgt   gagagggagg   ccagttggc    gcaagcctgt    2450
gggtggtgcg  gtggtggagg   ggttctggag   ggcttggcga   cataaacctc    2500
atacttggat  ttattccctgc  atctttccac   ctcccccagt   gctcaccaat    2550
```

FIG 16(iv)

```
gccccaggca tca..........approx 1000 bp..........        3563
ccaggttgcc ccttccccca aggtctggct ttggatgctt atgtgaacac  ≈3613
cgttttaagt tgccttggcc ccttcctcgg ttcctttttg gctgaggaat  ≈3663
ctctccatgg ctgcaggcag ggccattgtt gccattctac agataggggaa ≈3713
agtgcggctg ggggagctct gacagctgtc cctccccggg gcctctgtg  ≈3763
atgctgctga gggcctctgt tgtgctgggg tctgggttgg agctgggggt  ≈3813
aatggagatg aacctgccag gcacagtggg tgccccaggg ccccacccc   ≈3863
cgcagcctat gccatccctc catagagggg cctcaggttg ctgtctctct  ≈3913
                          /EXON 5...
ccttcccact atcgtccgca cagCACTGCC ATCTCCCCAC ACCCTCCAGG  ≈3963
AAGTTCAGGT CGCCATCATA AACAACTCTA TGTGCAACCA CCTCTTCCTC  ≈4013
AAGTACAGTT TCCGCAAGGA CATCTTTTGGA GACATGGTTT GTGCTGGCAA ≈4063
                                       /INTRON E...
TGCCCAAGGC GGGAAGGATG CCTGCTTCgt gagtgtcctt gccaccactc  ≈4113
ccagcccagg aaagcatcct gtgccctgt gccttatttg accctcatgc   ≈4163
caaccccggg aggtggagac tgttgcccca ctctgcagat gcagaaacgg  ≈4213
```

FIG 16(v)

```
aggcttggct gctgccaggg ggaggaggag gatgtgcacc cagtctaccc        ≈4263
agcccatag  ccttcccac  tctcagcccc tcccctgccc cactcactct        ≈4313
                                 /EXON 6...
gccccaggct gacctcagcc ccgctgctcc ccagGGTGAC TCAGGTGGAC        ≈4363
CCTTGGCCTG TAACAAGAAT GGACTGTGGT ATCAGATTGG AGTCGTGAGC        ≈4413
TGGGGAGTGG GCTGTGGTCG GCCCAATCGG CCCGGTGTCT ACACCAATAT        ≈4463
CAGCCACCAC TTTGAGTGGA TCCAGAAGCT GATGGCCCAG AGTGGGCATGT       ≈4513
CCCAGCCAGA CCCCTCCTGG CCGCTACTCT TTTTCCCTCT TCTCTGGGCT        ≈4563
CTCCCACTCC TGGGGCCGGT CTGAGCCTAC CTGAGCCCAT GCAGCCTGGG        ≈4613
GCCACTGCCA AGTCAGGCCC TGGTTCTCTT CTGTCTTGTT TGGTAATAAA        ≈4663
CACATTCCAG TTGATGCCTT GCAGGGCATT CTTCAaaagc agtggcttca        ≈4713
tggacagtc  attctctctt gtgcagacag cctgtctgtg cccctggctc        ≈4763
acaccacat  ctgttctgca ccatagaacc atctggttat ttcgatcaga        ≈4813
aagagaattg tgtgttgccc aggctggtct tgaacgccta gggtgtctcg        ≈4863
atc                                                            ≈4866
```

FIG 16(vi)

EXON III CACTGCTTTGAAACgtgagtgggggtgcgaacggag
gggtgcggggacgggcaggaacagggctggagggagtgccaccga
actttacctctggtctgatgccagacttgggcgtgaaagttgtgc
gtggatgcggcctggtgttctcctgagccccaggctgtgctgcag
ccggttacacccactccagttccctttgggtctcctggagggaac
cctgttcaggttattccagaatgttcttccagaacatttccacac
acttttgggtattctctcctttttctttcaacccaaagttcacc
actgaccatcccaccctcatcccctcctggtggacggtgcggt
acagtgtggggcactgagccaaggccagcaccccgggccgctgt

............INTRON C (716 BP)............

gtggactccatcctgccaatcccacattggcgtggtgcatctccc
cattcctccttgggctgcatgggggtgccctggaggccttggct
caatgcaaggctccttgggacagctctggaggtgacaagacccc
acccttctgctgcaggagcaggtcctagactttggttgtggtctg
tctgggctccttcatttctgcaggggaccctgggtgttagcaagt
agcagcaacaccacagtttccctcctgcactggaccccagttgt
gctcaggtagccagccctccatcagggccctgactgctctctt
ctcttctgccagctatagTGACCTTAGTGATCCC EXON IV
         ==    ==
                    ↓
              ALTERNATIVE
              SPLICING EVENTS
             ↙            ↘
    SHORT ISOFORM          LONG ISOFORM
         ↓                      │
CACTGCTTTGAAACTGACCTTAGTGATCCC
  H C F E T D L S D P
                                ↓
                    CACTGCTTTGAAACCTATAGTGACCTTAGTGATCCC
                      H C F E T Y S D L S D P

FIG 18(AII)

```
1   CGACCTATTGTCAGGGCCCTGCGGTCACAGGACCATCCCTTCCCGTATAGTGGGTGGCGA        20
    D  L  L  S  G  P  C  G  H  R  T  I  P  S  R  I  V  G  G  D

61  TGATGCTGAGCTTGGCCGCTGGCCTGGCAAGGGAGCCTGCGTGTATGGGCAACCACTT         40
    D  A  E  L  G  R  W  P  W  Q  G  S  L  R  V  W  G  N  H  L

121 ATGTGGCGCAACCTTGCTCAACCGCGCTGGGTGCTGCTTACACAGTGCCCACTGCTTCCAAAA   60
    C  G  A  T  L  L  N  R  R  W  V  L  T  A  A  H  C  F  Q  K

181 GGATAACGATCCTTTTGACTGGACAGTCCAGTTTGGTGAGCTGACTTCCAGGCCATCTCT      80
    D  N  D  P  F  D  W  T  V  Q  F  G  E  L  T  S  R  P  S  L

241 CTGGAACCTACACAGGCCTATTCCAACCGTTACCAAATAGAAGATATTTTCCTGAGCCCAA    100
    W  N  L  Q  A  Y  S  N  R  Y  Q  I  E  D  I  F  L  S  P  K

301 GTACTCGGAGCAGTATCCCAATGACATAGCCCTGCTGAAGCTGTCATCTCCAGTCACCTA     120
    Y  S  E  Q  Y  P  N  D  I  A  L  L  K  L  S  S  P  V  T  Y

361 CAATAACTTCATCCAGCCCATCTGCCTCCTGAACTCCACGTACAAGTTTGAGAACCGAAC    140
    N  N  F  I  Q  P  I  C  L  L  N  S  T  Y  K  F  E  N  R  T

421 TGACTGCTGGGTGACCGGCTGGGGCTATTGGAGAAGATGAGAGTCTGCCATCTCCCAA      160
    D  C  W  V  T  G  W  G  A  I  G  E  D  E  S  L  P  S  P  N
```

FIGURE 18 (AII)

```
481 CACTCTCCAGGAAGTGCAGGTAGCTATTATCAACAACAGCATGTGTAACCATATGTACAA
      T  L  Q  E  V  Q  V  A  I  I  N  N  S  M  C  N  H  M  Y  K  180

541 AAAGCCAGACTTCCGCACGAACATCTGGGGAGACATGGTTTGCGCTGGCACTCCTGAAGG
      K  P  D  F  R  T  N  I  W  G  D  M  V  C  A  G  T  P  E  G  200

601 TGGCAAGGATGCCTGCTTTGGTGACTCGGGAGGACCCCTTGGCCTGCGACCAGGATACGGT
      G  K  D  A  C  F  G  D  S  G  G  P  L  A  C  D  Q  D  T  V  220

661 GTGGTATCAGGTTGGAGTTGTGAGCTGGGGAATAGGCTGTGGTCGCCGCCCCAATCGCCCCTGG
      W  Y  Q  V  G  V  V  S  W  G  I  G  C  G  R  P  N  R  P  G  240

721 AGTCTATACCAACATCAGTCATCACTACAACTGGATCCAGTCAACCATGATCCGCAATGG
      V  Y  T  N  I  S  H  H  Y  N  W  I  Q  S  T  M  I  R  N  G  260

781 GCTGCTCAGGCCCTGACCCCAGTCCCCCTTGCTACTCTGTTTCTTACTCTGGCTTCCTC
      L  L  R  P  D  P  V  P  L  L  F  L  T  L  A  W  A  S  S  280

841 TTTGCTGAGGCCCTGAGCCCTGTACGTCACACCTGTGAGGTCAGGGTGTGTC
      L  L  R  P  A                                    285

901 TCTTTGTATCTTGCTTGCTAATAAACCTGTTAATATTTAAAAAAAAAAAAAAAAA
```

FIG 20A(AI)

FIG 20A(AII)

FIG 20A(AIII)

```
     CTGAACCGGGTTGTGGGCGGCGAGGACAGCACTGACAGCGAGTGGCCCTGGATCGTGAGC    60
  1  L  N  R  V  V  G  G  E  D  S  T  D  S  E  W  P  W  I  V  S

ATCCAGAAGAATGGGACCCACCACTGCGCCAGTTCTCTGCTCACCAGCCGCTGGGTGATC   120
 21  I  Q  K  N  G  T  H  H  C  A  G  S  L  L  T  S  R  W  V  I

ACTGCTGCCCACTGTTTCAAGGACAACCTGAACAAACCATACCTGTTTTCTGTGCTGCTG   180
 41  T  A  A  H  C  F  K  D  N  L  N  K  P  Y  L  F  S  V  L  L

GGGGCCTGGCAGCTGGGAAACCCTGGCTCTCGGTCCCAGAAGGTGGGTGCCGTGGGTG    240
 61  G  A  W  Q  L  G  N  P  G  S  R  S  Q  K  V  G  V  A  W  V

GAGCCCCACCCTGTGTATTCCTGGAAGGAAGGTGCAGACATTGCCCTGGTGCGT       300
 81  E  P  H  P  V  Y  S  W  K  E  G  A  C  A  D  I  A  L  V  R

CTCGAGCGGTCCATACAGTTCTCAGAGCGGGTCCTGCCTATCCTGCCTGATGCCTCT    360
101  L  E  R  S  I  Q  F  S  E  R  V  L  P  I  L  P  D  A  S

ATCCACCTCCCTCCAAACACCCACTGCTGGATCTCAGGGGAGCATCCAAGATGGA     420
121  I  H  L  P  P  N  T  H  C  W  I  S  G  W  G  S  I  Q  D  G
```

FIGURE 20A (AII)

```
    GTTCCCTTGCCCCACCCTCAGACCCTGCAGAAGCTGAAGGTTCCTATCATCGACTCGGGAA  480
141  V  P  L  P  P  H  P  Q  T  L  Q  K  L  K  V  P  I  I  D  S  E
    GTCTGCAGCCATCTGTACTGGCGGGGAGCAGGAGACCATCACTGAGGACATGCTG        540
161  V  [C] S  H  L  Y  W  R  G  A  G  Q  G  P  I  T  E  D  M  L
    TGTGCCGGCTAACTTGGAGGGGGAGCGGGATGCTTGTCTGGGCGACTCCGGGGCCCCTC    600
181  [C] A  G  Y  L  E  G  E  R  D  A  [C] L  G  D  (S) G  G  P  L
    ATGTGCCAGGTGGACGGCGCCCTGGCTGCCCGGCATCATCAGCTGGGGCGAGGGCTGT     660
201  M  [C] Q  V  D  G  A  W  L  L  A  G  I  I  S  W  G  E  G  [C]
    GCCGAGCGCAACAGGCCCGGGGTGCAGCCCGTCTACAGCTCTCTGCGCACCGCTCTGGTGGAG  720
221  A  E  R  N  R  P  G  V  Y  I  S  L  S  A  [H] R  S  W  V  E
    AAGATCGTGCAAGGGGTGCAGGTGCAGCTGCGGGGTCGAGCCCAGGGTGGGGCCCTCAGGGCA  780
241  K  I  V  Q  G  V  Q  L  R  G  R  A  Q  G  G  A  L  R  A
    CCGAGCCAGGGCTCTGGGGCTCCTAGGGCCCCAGCGCCGACGCGGGGCTCGG           840
261  P  S  Q  G  S  G  A  A  A  R  S
    ATCTGAAAGGCCGCCAGATCCACATCTGGATCTCGGGCGGTTC                    900
    CCCGCCCGTAAATAGGCTCATCTCTACCTCTACCCTCTGGGGCCCGACGGCTGCTGCGGAA  960
```

FIGURE 20A (AIII)

```
AGGAAACCCCCTCCCCGACCCGCGCCCGACGGCCTCAGGCCCCGCTCCAAGGCATCAGGCC  1020
CCGCCCAACGCCTCATGTCCCCGACTTCCGGCCCCGGCCCCGGCCCCCGCCCCAGCG      1080
CTTTGTGTATATAAATGTTAATGATTTTTATAGGTATTTGTAACCCTGCCACATATCT     1140
TATTTATTCCTCCAATTTCAATAAA
```

FIG 20B(AI)

FIG 20B(AII)

```
    AATGCGGCCACTCCAAGGAGGCCGGGAGGATTGTGGGAGGCCAAGACACCCAGGAAGGAC  60
  1  N A A T P R R P G G I V G G Q D T Q E G
     [C] G H S K E A G R ▽ I V G G Q D T Q E G

GCTGGCCGTGGCCAGGTTGGCCTGTGGTTGACCTCTGTGGGCCATGTATGTGGGGCTCCC  120
 21  R W P W Q V G L W L T S V G H V [C] G G S

TCATCCACCACCGCTGCTCACAGCCGCTCTGCTAAGCCGCTCTTCCTGAGGTCTGAGGATCCCG  180
 41  L I H P R W V L T A A (H) [C] F L R S E D P

GGCTCTACCATGTTAAAGTCGGAGGGCTGACACCCTCACTTTCAGAGCCCCACTCGGCCT  240
 61  G L Y H V K V G G L T P S L S E P H S A

TGGTGGCTGTGTGAGGAGGCTGGAGCTGGTGTTCATACCAGGCCCTCCCAGTTCAGCCCCATCGCC  300
 81  L V A V R R L L V H S S Y H G T T T S G

ACATTGCCCTGATGGAGCTGGACTCCCCCTTGCAGGCCTCCCAGTTCAGCCCCATCGCC  360
101  I (D) I A L M E L D S P L Q A S Q F S P I [C]

TCCCAGGACCCCAGACCCCCACTCCGGCCCATTGGGACCGTGTGCTGGGTAAACGGGCTGGGGG  420
121  L P G P Q T P L A I G T V [C] W V N G L G

TCCACTCAGGAGGCCCTGGCGAGTGTCCTTCAGGAGGTGGCCGTGCCCCTCCTGGACT  480
141  V H S G E A L A S V L Q E V A V P L L D
```

FIGURE 20B (AII)

```
      CGAACATGTGTGAGCTGATGTACCACCTAGGAGAGCCCTGGCTGGCCAGCGCCTCA 540
161   S  N  M  C  E  L  M  Y  H  L  G  E  P  S  L  A  G  Q  R  L

TCCAGGACGACACATGCTCTGTGCTGGCTCTGTCCAGGCAAGAAGACTCCTGCCAGGGTG 600
181   I  Q  D  D  M  L  C  A  G  S  V  Q  G  K  K  D  S  C  Q  G

ACTCCGGGGGCCGCTGGTCTGCCCCATCAATGATACGTGGATCCAGGCCGGCATTGTGA 660
201   D  S  G  G  P  L  V  C  P  I  N  D  T  W  I  Q  A  G  I  V

GCTGGGGATTCGGCTGTGTGCCCGGCCCTTTCGGCCCGGGTGTCTACACCCAGGTGCTAAGCT 720
221   S  W  G  F  G  C  A  R  P  F  R  P  G  V  Y  T  Q  V  L  S

ACACAGACTGGATTCAGAGAACCCTGGCTGAATCTCACTCAGGCATGTCTGGGGCCCGCC 780
241   Y  T  D  W  I  Q  R  T  L  A  E  S  H  S  G  M  S  G  A  R

CAGGTGCCCCAGGATCCCACTCCAGGCACCTCCAGATCCCACCCAGTGCTGCTTGAGC 840
261   P  G  A  P  G  S  H  S  G  T  S  R  S  H  P  V  L  L  E

TGTTGACCGTATGCTTGCTTGGGTCCCTGTGAACCATGAGCCGGATCCCC 900
281   L  L  T  V  C  L  L  G  S  L

TTTCTGGTAGGATTGATGGAATCTAATAATAAA
```

FIG 20C(AI)

FIG 20C(AII)

```
  1  CCTGTGGTCGCCCCAGGATGCTGAACCGAATGGTGGGCGGGCAGGACACGGCAGGAGGCG    60
     P V V A P R M L N R ▽M V G G Q D T Q E G
     Ⓒ G R P R M L N R ▽M V G G Q D T Q E G

21  AGTGGCCCTGCAAGTCAGCATCCAGCGCAACGGAAGCCACTTCTGCGGGCAGCCTCA     120
     E W P W Q V S I Q R N G S H F Ⓒ G G S L

41  TCGCGGAGCAGTGGGTCCTGACGGCTGCCGCACTGCCTTCCCGCAACACCTCTGAGACGTCCC   180
     I A E Q W V L T A A Ⓗ Ⓒ F R N T S E T S

61  TGTACCAGGTCCTGCTGGGGCAAGGCAGTAGTGCAGCCCGGACCCACACGCTATGTATG    240
     L Y Q V L L G A R Q L V Q P G P H A M Y

81  CCCGGGTGAGGCAGGTGGAGAGCAACCCCCTGTACCAGGGCACCGCCTCCAGCGCTGACG    300
     A R V R Q V E S N P L Y Q G T A S S A Ⓓ

101  TGGCCCTGGTTGAGCTGGAGGCTGAGGCTCCCGTGCCCTTCACCAATTACATCCTCCCCGTGCC    360
     V A L V E L E A P V P F T N Y I L P V Ⓒ

121  TGCCTGACCCCTCGGTGATCTTTGAGACGGGCATGAACTGTGGGTCACTGGCTGGGGCA    420
     L P D P S V I F E T G M N Ⓒ W V T G W G

141  GCCCCAGTGAGGAGGAAGAGGATCTCCTGCCCGAACCGGAAACTGCTGTGCCCA     480
     S P S E E D L L P E P R I L Q K L A V P
```

FIGURE 20C (AII)

```
     TCATCGACACACCAAGTGCAACCCTGCTCTACAGCAAAGACACCGAGTTTGGCTACCAAC  540
161   I  I  D  T  P  K [C] N  L  L  Y  S  K  D  T  E  F  G  Y  Q

CCAAAACCATCAAGAATGACATGCTGTGCGCCGGCTTCGAGGAGGGCAAGAAGGATGCCT  600
181   P  K  T  I  K  N  D  M  L [C] A  G  F  E  E  G  K  K  D  A

GCAAGGGCGACTCGGGCGGTGTGCCTGGTGTGGGTCAGTCGTGGCTGCAGGCGG  660
201  [C] K  G  D (S) G  G  P  L  V [C] L  V  G  Q  S  W  L  Q  A

GGGTGATCAGCTGGGGTGAGGGCTGTGCCCCAGAACCGCCCAGTGTCTACATCCGTG  720
221   G  V  I  S  W  G  E  G [C] A  R  Q  N  R  P  G  V  Y  I  R

TCACCGCCCACCACAACTGGATCATCCATCGGATCATCCCCAAACTGCAGTTCCAGCCAGCGA  780
241   V  T  A  H  H  N  W  I  I  H  R  I  I  P  K  L  Q  F  Q  P  A

GGTTGGGGCGGCCAGAAGTGAGACACCCCCGGGCAGGAGCCCCTTGAGCAGAGCTCTGCAC  840
261   R  L  G  G  Q  K  *  D  P  R  G  Q  E  P  L  E  Q  S  S  A

CCAGCCTGCCCGCCCACACCATCCTGGTCCTGCCCAGCCTGGTCCTGTTGCACCTGTGAG  900
281   P  S  L  P  A  H  T  I  L  V  L  P  A  L  L  H  L

CCCCACCAGACTCATTTGTAAATAGCGCTCCTCCCCTCTCAAATACCCTTATTTTA  960
     TTTATGTTTCTCCCAATAAA
```

US 6,479,274 B1

DNA MOLECULES ENCODING HUMAN HELA2 OR TESTISIN SERINE PROTEINASES

FIELD OF THE INVENTION

The present invention related generally to novel molecules and more particularly novel proteinaceous molecules involved in or associated with regulation of cell activities and/or viability. The present invention is particularly directed to novel serene proteinases and a novel kinase and to derivatives, agonists and antagonists thereof. In one embodiment, the present invention provides a novel serine proteinase, referred to herein as "HELA2" or "testisin", which has roles in spermatogenesis, in suppressing testicular cancer and as a marker for cancers.

BACKGROUND OF THE INVENTION

The rapidly increasing sophistication of recombinant DNA technology is greatly facilitating research and development in the medical and allied health fields. This is particularly the case in the area of cell regulation leading to a greater understanding of the events leading to or involved in cancer, development of acquired immunodeficiency disease syndrome (AIDS), neurological disorders, heart disease, tissue graft rejection and infertility amongst many other conditions.

Two particularly important classes of molecules are the proteinases and kinases.

Proteinases play important roles in a number of physiological and pathological processes such as proteolytic cascades involved in blood coagulation, fibrinolysis and complement activation as well as cleavage of growth factors, hormones and receptors, the release of bioactive molecules and processes involving cell proliferation and development, inflammation, tumour growth and metastasis. Of particular significance are the cellular proteinases, or those proteinases synthesized in cells and tissues which serve to activate or deactivate proteins responsible for performing specific functions. These proteinases may be found outside the cell, within the cell or may be present on the cell surface.

Serine proteinases are particularly important. These proteinases are characterised by a mechanism involving serine, histidine and aspartate amino acids in the serine proteinase active site. Members of the serine proteinase family which play important roles in a range of cellular functions and which have demonstrated causative roles in human diseases include tissue-type plasminogen activator and thrombin (thrombosis and blood clotting), urokinase-type plasminogen activator (cancer and metastasis), trypsin and elastase (emphysema and liver disease) and angiotensin converting enzyme (hypertension).

A serine proteinase is also implicated in TNFα degradation and soluble TNF-receptor (p75) release by THP1 cells (Vey et al. *Eur. J. Imm.* 26, 2404–2409, 1996). Serine proteinases have been implicated in the activation of macrophages (Nakabo et al. *J. Leukocyte Biol.* 60, 328–336, 1996), in nuclear laminin degradation in apoptosis (McConkey et al. *J.Biol. Chem.,* 271, 22398–22406, 1996), in prostaglandin-E2 induced release of soluble TNF receptor shedding (Choi et al. *Cellular Immunology* 170, 178–184, 1996), in PAF synthesis (Bussolino et al. *Eur. J. Immunol.* 24, 3131–3139, 1994), and in the proteolysis of IkB, a regulatory molecule important in signal transduction and apoptosis. Release of serine proteinases known as granzymes is central to CTL killing and many of the substrates cleaved by granzymes are also cleaved by cellular proteinases (for example, IL-1β is a substrate for Granzyme B as well as the cysteine proteinase, interleukin 1β-converting enzyme (ICE)). Granzyme A, a serine proteinase with Arg-amidolytic activity, has been reported to induce the production of IL-6 and IL-8 in lung fibroblasts (Sower et al. *Cellular Immunology* 171, 159–163, 1996) and cleaves IL1β to a 17 kD mature form that is biologically active.

Kinases are a large group of molecules, many of which regulate the response of cells to external stimuli. These molecules regulate proliferation and differentiation in eukaryotic cells frequently via signal transduction pathways.

The identification of new serine proteinases and kinases permits the development of a range of derivatives, agonists and antagonists at the nucleic acid and protein levels which in turn have applications in the treatment and diagnosis of a range of conditions such as cancer, inflammation, neurological disorders amongst many other conditions including conditions which initiate or promote apoptosis such as viral infection, old age and drug abuse. One particularly useful serine proteinase HELA2 (testisin) identified in accordance with the present invention is involved in spermatogenesis, testicular cancer and as a marker for cancer.

SUMMARY OF THE INVENTION

Sequence Identity Numbers (SEQ ID NOs.) for the nucleotide and amino acid sequences referred to in the specification are defined at the end of the subject specification.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention provides a novel molecule in isolated form involved in or associated with regulation of cell activity and/or viability.

Another aspect of the present invention contemplates an isolated proteinaceous molecule involved in or associated with regulation of cell activity and/or viability comprising a sequence of amino acids encoded by a nucleotide sequence, at least a portion of which, is capable of being amplified by polymerase chain reaction (PCR) using the following primers:

5' ACAGAATTCTGGGTIGTIACIGCIGCICAYTG3' [SEQ ID NO:1]; and

5' ACAGAATTCAXIGGICCICCIC/GT/AXTCICC3' [SEQ ID NO:2];

or a complementary form of said primers.

The proteinaceous molecule of the present invention may be a serine proteinase or a kinase.

Yet another aspect of the present invention is directed to an isolated serine proteinase comprising the amino acid sequence substantially set forth in SEQ ID NO:4 or an amino acid sequence having at least about 50% similarity to all or part thereof. This serine proteinase is referred to herein as a short isoform (S) of "HELA2" or "testisin".

Still another aspect of the present invention relates to an isolated serine proteinase comprising the amino acid sequence substantially as set forth in SEQ ID NO:6 or an amino acid sequence having at least about 50% similarity to all or part thereof. This serine proteinase is referred to herein as a long isoform (L) of HELA2 (testisin).

Still yet another aspect of the present invention provides an isolated serine proteinase comprising an amino acid sequence substantially as set forth in SEQ ID NO:8 or an amino acid sequence having at least about 50% similarity to all or part thereof. This serine proteinase is referred to herein as "ATC2".

Even yet another aspect of the present invention is directed to a serine proteinase in isolated form comprising a sequence of amino acids encoded by a nucleotide sequence substantially as set forth in SEQ ID NO:3 or a nucleotide sequence having at least 50% similarity to all or part thereof or a nucleotide sequence capable of hybridising to the sequence set forth in SEQ ID NO:3 under low stringency conditions at 42° C.

Another aspect of the present invention relates to a serine proteinase in isolated form comprising a sequence of amino acids encoded by a nucleotide sequence substantially as set forth in SEQ ID NO:5 or a nucleotide sequence having at least 50% similarity to all or part thereof or a nucleotide sequence capable of hybridising to the sequence set forth in SEQ ID NO:5 under low stringency conditions at 42° C.

Still another aspect of the present invention provides a serine proteinase in isolated form comprising a sequence of amino acids encoded by a nucleotide sequence substantially as set forth in SEQ ID NO:7 or a nucleotide sequence having at least 50% similarity to all or part thereof or a nucleotide sequence capable of hybridising to the sequence set forth in SEQ ID NO:7 under low stringency conditions at 42° C.

Another embodiment of the present invention is directed to a kinase in isolated form comprising an amino acid sequence substantially as set forth in SEQ ID NO:10 or having 50% amino acid similarity to all or part thereof. This kinase is referred to herein as "BCON3".

In a related embodiment, the kinase comprises an amino acid sequence encoded by a nucleotide sequence substantially as set forth in SEQ ID NO:9 or a nucleotide sequence having at least 50% similarity to all or part of the nucleotide sequence set forth in SEQ ID NO:9 or a nucleotide sequence capable of hybridising to the nucleotide sequence set forth in SEQ ID NO:9 under low stringency conditions at 42° C.

The present invention further provides an isolated nucleic acid molecule encoding a polypeptide wherein at least a portion of said nucleic acid molecule is capable of being amplified by polymerase chain reaction (PCR) using the following primers:

5' ACAGAATTCTGGGTIGTIACIGCIGCICAYTG3' [SEQ ID NO:1]; and

5'ACAGAATTCAXIGGICCICCIC/GT/AXTCICC3' [SEQ ID NO:2];

or a complementary form of said primers.

The present invention also provides an isolated nucleic acid molecule comprising a sequence of nucleotides substantially as set forth in SEQ ID NO:3 or having 50% similarity to all or part thereof or a nucleic acid molecule capable of hybridising to SEQ ID NO:3 under low stringency conditions at 42° C.

Another aspect of the present invention provides an isolated nucleic acid molecule comprising a sequence of nucleotides substantially as set forth in SEQ ID NO:5 or having 50% similarity to all or part thereof or a nucleic acid molecule capable of hybridising to SEQ ID NO:5 under low stringency conditions at 42° C.

Still another aspect of the present invention is directed to an isolated nucleic acid molecule comprising a sequence of nucleotides substantially as set forth in SEQ ID NO:7 or having 50% similarity to all or part thereof or a nucleic acid molecule capable of hybridising to SEQ ID NO:7 under low stringency conditions at 42° C.

Even still another aspect of the present invention provides an isolated nucleic acid molecule comprising a sequence of nucleotides substantially as set forth in SEQ ID NO:9 or having 50% similarity to all or part thereof or a nucleic acid molecule capable of hybridising to SEQ ID NO:9 under low stringency conditions at 42° C.

Another aspect of the present invention provides an isolated serine proteinase encoded by a gene proximal to a cluster of genes on a mammalian chromosome.

More particularly, this aspect of the present invention is directed to a serine proteinase encoded by a gene proximal to a cluster of genes or human chromosome 16p13.3 or its equivalent in a non-human species.

Still more particularly, the serine proteinase is encoded by a gene comprising a nucleotide sequence substantially as set forth in SEQ ID NO:3 or 5 or 28 or 29 or 30 or a nucleotide sequence having at least 50% similarity to any one thereof or a nucleotide sequence capable of hybridizing to any one of SEQ ID NO:3 or 5 or 28 or 29 or 30 under low stringency conditions at 42° C. or a nucleotide sequence encoding a serine proteinase having an amino acid sequence substantially as set forth in SEQ ID NO:4 or 6 or an amino acid sequence having at least about 50% similarity to SEQ ID NO:4 or 6.

BRIEF DESCRIPTION OF THE DRAWINGS

FIGS. 1A–1B are representations showing (A) schematic and (B) hydrophobicity plot of the HELA2 amino acid sequence.

FIG. 5 is a photographic representation of: (A) silver stained gel showing purification of recombinant HELA2 (testisin) from E. coli. The purified HELA2 (testisin) is indicated by the arrow in the eluate fractions. Some HELA2 (testisin) is also found in the wash tractions as the affinity matrix was not used in excess. His-N21 is one clone containing the amino-terminal His tag, and clones His-C21, His-C22 and His-C23 are three different clones with the carboxy-terminal His tag. (B) Western blot of native and denatured recombinant HELA2 (testisin) probed with Clontech anti-His tag-antibody. The 32 kD band shown by the arrow is HELA2 (testisin). HELA2 (testisin) is not detected in the denatured samples as it appears that denaturation with urea destroys the His epitope recognised by the monoclonal antibody.

FIGS. 6(I)–(III) are representations of the amino acid sequence of HELA2 (testisin) showing the regions of the molecule selected for generation of peptide antigens.

FIGS. 14A–14B: (A) photographic representations of northern blot analysis of HELA2 (testisin) mRNA showing signals in normal testis of 4 patients and absence of signal in the tumours of these patients; (B) a photographic representation of the localisation of HELA2 (testisin) protein in a human germ cell tumour section assessed by immunohistochemical staining using anti-HELA2 (testisin) peptide antibodies. Staining is only detected in the normal (N) tissue and not present in the tumour (T) tissue.

FIGS. 16(I–II) are representations of HELA2 (testisin). Nucleotides in introns are in lowercase and exons in uppercase. The putative transcription start site is marked by +1.

FIG. 17 is a representation of the DNA sequence of Intron C and flanking exons showing where alternative mRNA splicing occurs to generate the two isoforms of HELA2 (testisin).

FIGS. 18A–18B are representations of: (AI–II) the cDNA sequence of the mouse homologue of HELA2 (testisin). Catalytic residues are indicated by circles and cysteines likely involved in disulfide bonding are indicated by squares; (B) Hydrophobicity plot of HELA2 (testisin) amino acid sequence.

Figure 2B:
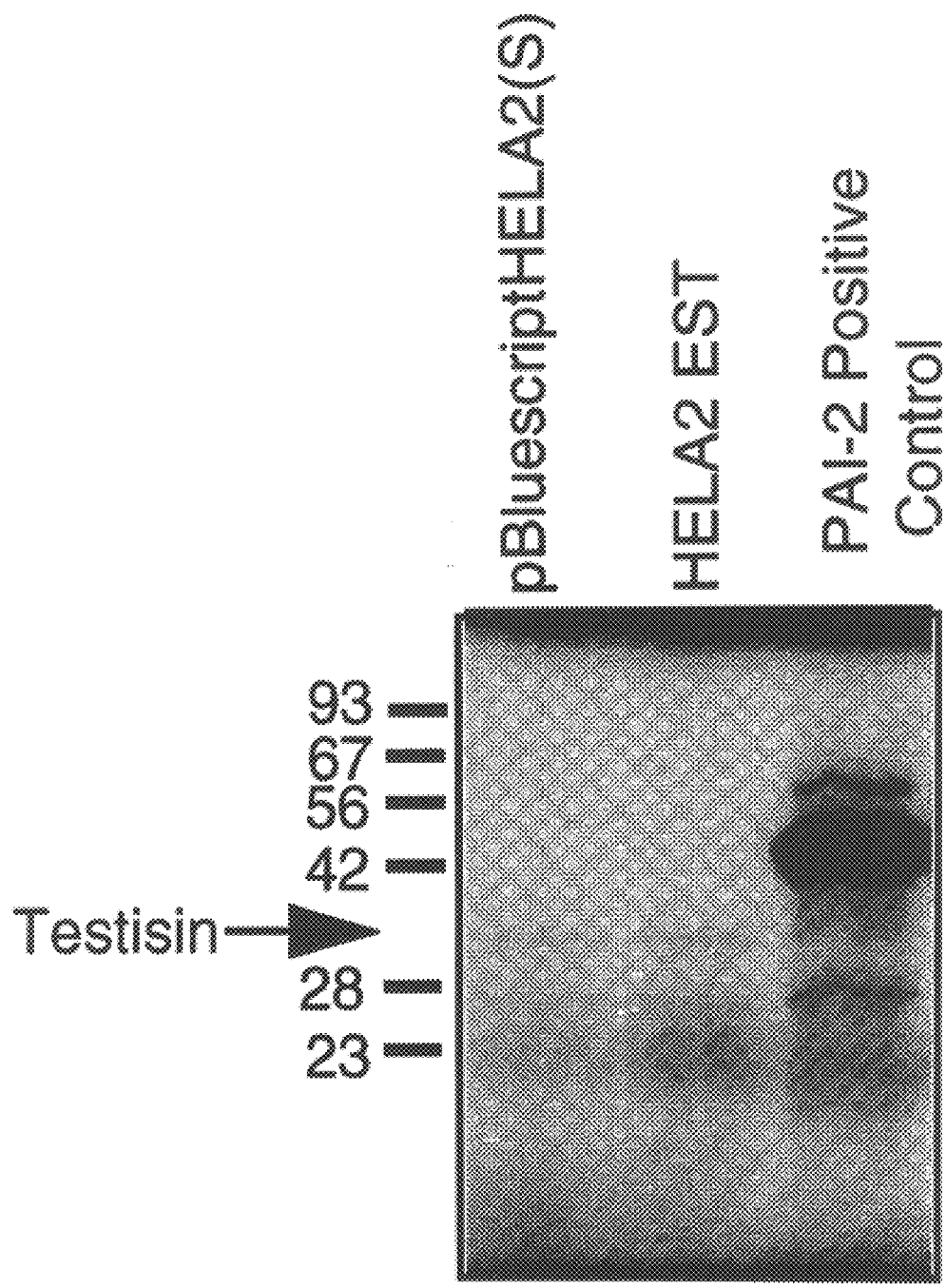
FIGS. 2A(I)–2A(II) are diagrammatic representations showing: (AI–AII) the amino acid sequence of HELA2 (testisin). The putative signal sequence, light chain, heavy chain and transmembrane domains are as indicated, the catalytic amino acids, His, Asp and Ser are as designated; insertion of Tyr-Ser (YS) 4 amino acids after the catalytic His is found in the long isoform of testisin and is due to alternative mRNA splicing; (B) in vitro transcription/translation of HELA2 (testisin) showing the protein product.

A summary of the SEQ ID NOs used throughout the specification is presented in Table 1.

TABLE 1

| SEQ ID NO | DESCRIPTION |
| --- | --- |
| 1 | *PCR primer sequence |
| 2 | *PCR primer sequence |
| 3 | Nucleotide sequence of short form of HELA2 |
| 4 | Amino acid sequence of short form of HELA2 |
| 5 | Nucleotide sequence of long form of HELA2 |
| 6 | Amino acid sequence of long form of HELA2 |
| 7 | Nucleotide acid sequence of ATC2 |
| 8 | Amino acid sequence of ATC2 |
| 9 | Nucleotide acid sequence of BCOM3 |
| 10 | Amino acid sequence of BCOM3 |
| 11 | Primers used to generate amino terminal tagged protein |
| 12 | Primers used to generate amino terminal tagged protein |
| 13 | Primers used to generated carboxy-linked terminal protein |
| 14 | Primers used to generated carboxy-linked terminal protein |
| 15 | Peptide antigen T20-33 |
| 16 | Peptide antigen T46-63 |
| 17 | Peptide antigen T175-190 |
| 18 | Forward primer |
| 19 | Reverse primer |
| 20 | Forward primer |
| 21 | Reverse primer |
| 22 | Forward primer |
| 23 | Reverse primer |
| 24 | Serine proteinase activation motif |
| 25 & 26 | Mouse HELA2 cDNA sequence |
| 27 | Human genomic DNA sequence |
| 28 | Clustered serine proteinase gene SP001LA |
| 29 | Clustered serine proteinase gene SP002LA |
| 30 | Clustered serine proteinase gene SP003LA |

*Abbreviations:
X = A or G
Y = C or T
I = Inosine.

A list of single and three letter abbreviations for amino acid residues is presented in Table 2.

TABLE 2

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |

TABLE 2-continued

| Amino Acid | Three-letter Abbreviation | One-letter Symbol |
|---|---|---|
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

DETAILED DESCRIPTION OF PREFERRED EMBODIMENTS

The present invention is predicated in part on a genetic engineering approach to identify nucleotide sequences encoding serine proteinases or kinases. The genetic engineering approach is based on the use of degenerate primers corresponding to conserved regions of serine proteinases (amino acids flanking His- and Ser-residues) to amplify gene fragments spanning these regions for cDNA, using low stringency reverse transcriptase-polymerase chain reaction (RT-PCR).

This technique has been successfully used, in accordance with the present invention, to identify serine proteinases and kinases useful in modulating cell activity and viability including modulating spermatogenesis, acting as tumour suppressors and acting as a marker for non-testicular cancers.

Accordingly, one aspect of the present invention provides a novel molecule in isolated form involved in or associated with regulation of cell activity and/or viability.

More particularly, the present invention contemplates a novel serine proteinase in isolated form comprising a sequence of amino acids encoded by a nucleotide sequence, at least a portion of which, is capable of being amplified by polymerase chain reaction (PCR) using the following primers.

5' ACAGAATTCTGGGTIGTIACIGCIGCICAYTG3' [SEQ ID NO:1]; and

5'ACAGAATTCAXIGGICCICCIC/GT/AXTCICC3' [SEQ ID NO:2];

or a complementary form of said primers.

Preferably, X is A or G, Y is C or T and I is inosine.

In a particularly preferred embodiment, the isolated serine proteinase comprises the amino acid sequence substantially set forth in SEQ ID NO:4 or an amino acid sequence having at least about 50% similarity to all or part thereof. This serine proteinase is referred to herein as a short isoform of "HELA2" or "HELA2 (testisin)". The terms "HELA2" and "testisin" are used interchangeably throughout the subject specification to refer to the same molecule.

In another preferred embodiment, the amino acid sequence of the serine proteinase is substantially as set forth in SEQ ID NO:6 or an amino acid sequence having at least about 50% similarity to all or part thereof. This serine proteinase is the long isoform of HELA2 or HELA2 (testisin).

Yet another preferred embodiment of the present invention provides an amino acid sequence substantially as set forth in SEQ ID NO:8 or an amino acid sequence having at least about 50% similarity to all or part thereof. This serine proteinase is referred to herein as "ATC2".

Another aspect of the present invention relates to a serine proteinase in isolated form comprising a sequence of amino acids encoded by a nucleotide sequence substantially as set forth in SEQ ID NO:3 or a nucleotide sequence having at least 50% similarity to all or part thereof or a nucleotide sequence capable of hybridising to the sequence set forth in SEQ ID NO:3 under low stringency conditions at 42° C.

Still another aspect of the present invention is directed to a serine proteinase in isolated form comprising a sequence of amino acids encoded by a nucleotide sequence substantially as set forth in SEQ ID NO:5 or a nucleotide sequence having at least 50% similarity to all or part thereof or a nucleotide sequence capable of hybridising to the sequence set forth in SEQ ID NO:5 under low stringency conditions at 42° C.

In another aspect of the present invention, there is provided a serine proteinase in isolated form comprising a sequence of amino acids encoded by a nucleotide sequence substantially as set forth in SEQ ID NO:7 or a nucleotide sequence having at least 50% similarity to all or part thereof or a nucleotide sequence capable of hybridising to the sequence set forth in SEQ ID NO:7 under low stringency conditions at 42° C.

Another embodiment of the present invention is directed to a kinase in isolated form comprising an amino acid sequence substantially as set forth in SEQ ID NO:10 or having 50% amino acid similarity to all or part thereof. This kinase is referred to herein as "BCON3".

In a related embodiment, the kinase comprises an amino acid sequence encoded by a nucleotide sequence substantially as set forth in SEQ ID NO:9 or a nucleotide sequence having at least 50% similarity to all or part of the nucleotide sequence set forth in SEQ ID NO:9 or a nucleotide sequence capable of hybridising to the nucleotide sequence set forth in SEQ ID NO:9 under low stringency conditions at 42° C.

The present invention further provides an isolated nucleic acid molecule comprising a sequence of nucleotides encoding or complementary to a sequence encoding a novel molecule involved in or associated with regulation of cell activity and/or viability. Preferably, the nucleic acid molecule is capable of being amplified by PCR using the primers set forth in SEQ ID NO:1 and/or SEQ ID NO:2.

More particularly, the present invention further provides an isolated nucleic acid molecule comprising a sequence of nucleotides substantially as set forth in SEQ ID NO:3 or having 50% similarity to all or part thereof or a nucleic acid molecule capable of hybridising to SEQ ID NO:3 under low stringency conditions at 42° C.

Another aspect of the present invention provides an isolated nucleic acid molecule comprising a sequence of nucleotides substantially as set forth in SEQ ID NO:5 or having 50% similarity to all or part thereof or a nucleic acid molecule capable of hybridising to SEQ ID NO:5 under low stringency conditions at 42° C.

Another aspect of the present invention is directed to an isolated nucleic acid molecule comprising a sequence of nucleotides substantially as set forth in SEQ ID NO:7 or having 50% similarity to all or part thereof or a nucleic acid molecule capable of hybridising to SEQ ID NO:7 under low stringency conditions at 42° C.

Still another aspect of the present invention provides an isolated nucleic acid molecule comprising a sequence of nucleotides substantially as set forth in SEQ ID NO:9 or having 50% similarity to all or part thereof or a nucleic acid molecule capable of hybridising to SEQ ID NO:9 under low stringency conditions at 42° C.

Reference herein to a low stringency includes low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

Reference herein to similarity to "part" of a sequence means similarity to at least about 4 contiguous amino acids or at least about 12 contiguous nucleotide bases and more preferably at least about 7 contiguous amino acids or at least about 21 contiguous nucleotide bases.

The term "similarity" includes exact identity between sequences or, where the sequence differs, different amino acids may be related to each other at the structural, functional, biochemical and/or conformational levels.

The term "isolated" includes biological purification and biological separation and encompasses molecules having undergone at least one purification, concentration or separation step relative to its natural environment. For example, a preparation may comprise at least about 10%, preferably at least about 20%, more preferably at least about 30%, still more preferably at least about 50% or greater of the molecule relative to at least one other component in a composition as determined by activity, mass, amino acid content, nucleotide content or other convenient means.

Hereinafter, the molecules of the present invention are referred to as a "proteinase/kinase". The term "proteinase/kinase" includes the serine proteinases HELA2 (testisin) and ATC2 and the kinase BCON3. The proteinase/kinase of the present invention may be in isolated, naturally occurring form or recombinant or synthetic form or chemical analogues thereof.

The proteinase/kinase of the present invention is preferably of human origin but from non-human origins are also encompassed by the present invention. Non-human animals contemplated by the present invention include primates, livestock animals (e.g. sheep, cows, pigs, goats, horses, donkeys), laboratory test animals (e.g,. mice, rats, guinea pigs, hamsters, rabbits), domestic companion animals (e.g. dogs, cats), birds (e.g. chickens, geese, ducks and other poultry birds, game birds, emus, ostriches) and captive wild or tamed animals (e.g. foxes, kangaroos, dingoes). The present invention also encompasses a proteinase/kinase homologue from Xenopus and plants.

The nucleic acid molecules encoding a proteinase/kinase may be genomic DNA, cDNA or RNA such as mRNA.

Yet another aspect of the present invention provides an isolated serine proteinase encoded by a gene proximal to a cluster of genes on a mammalian chromosome. The cluster of genes is preferably on human chromosome 16p13.3 or its equivalent in a non-human species. The cluster is made up of genes all encoding or having the potential to encode a serine proteinase or homologue, derivative or functional or evolutionary equivalent thereof. Preferably, the gene cluster comprises two or more of genes comprising a nucleotide sequence selected from SEQ ID NO:3 and 5 (HELA2, short and long forms, respectively) and SEQ ID NO:28 (SP001LA), SEQ ID NO:29 (SP002LA), SEQ ID NO:30 (SP003LA) and SP004LA (see FIG. 19) or a nucleotide sequence having at least 50% similarity to any one of those sequences or capable of hybridizing to any one of those sequences under low stringency conditions at 42° C.

The term "proximal" is used in its broadest sense to mean a gene cluster and includes a gene within proximity to another gene.

Another aspect of the present invention contemplates a method for cloning a nucleotide sequence encoding a novel serine proteinase, said method comprising screening a nucleic acid library with said one or more oligonucleotides defined by SEQ ID NO:1 and/or SEQ ID NO:2 and obtaining a clone therefrom which encodes said novel serine proteinase or part thereof.

Preferably, the nucleic acid library is genomic DNA, cDNA, genomic or mRNA library.

Preferably, the nucleic acid library is a cDNA expression library.

Preferably, the nucleic acid library is of human origin such as from brain, liver, kidney, neo-natal tissue, embryonic tissue, tumour or cancer tissue.

With respect to HELA2 (HELA2 (testisin)), significant expression is generally only found in normal testis. Accordingly, the present invention extends to nucleic acid molecules capable of tissue-specific or substantially tissue-specific expression.

Still another embodiment contemplates the promoter or a functional part thereof of the genomic gene encoding the subject proteinase/kinase of the present invention. The promoter may readily be obtained by, for example, "chromosome walking". A particularly useful promoter is from HELA2 (testisin) which can be regarded as a testis specific promoter. This promoter can be used, for example, to direct testis specific expression of genetic sequences operably linked to the promoter and may be used inter alia gene therapy or modulation of fertility.

The present invention further contemplates a range of derivatives of the subject proteinase/kinase. Derivatives include fragments, parts, portions, mutants, homologues and analogues of the subject polypeptides and corresponding genetic sequences. Derivatives also include single or multiple amino acid substitutions, deletions and/or additions to the subject molecules or single or multiple nucleotide substitutions, deletions and/or additions to the genetic sequence encoding the molecules. "Additions" to amino acid sequences or nucleotide sequences include fusions with other peptides, polypeptides or proteins or fusions to nucleotide sequences. Reference herein to the serine proteinase and kinase includes reference to all derivatives thereof including functional derivatives or immunologically interactive derivatives.

Analogues of the subject serine proteinase and kinase contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |

TABLE 3-continued

| Non-conventional amino acid | Code | Non-conventional amino acid | Code |
|---|---|---|---|
| D-ornithine | Dorn | L-N-methyltyrosine | Nmtyr |
| D-phenylalanine | Dphe | L-N-methlylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |

TABLE 3-continued

| Non-conventional amino acid | Code | Non-conventional amino acid | Code |
|---|---|---|---|
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenyl-alanine | Mhphe |
| L-α-methylisoleucine | Mile | N-(2-methylthioethyl)-glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenyl-alanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenyl-alanine | Nmhphe |
| N-(N-(2,2-diphenyl-ethyl)carbamyl-methyl)glycine | Nnbhm | N-(N-(3,3-diphenyl-propyl)carbamylmethyl)-glycine | Nnbhe |
| 1-carboxy-1-(2,2-diphenyl-ethylamino)-cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilise the proteinase/kinase if administered to an individual or for use as a diagnostic reagent.

The present invention further contemplates chemical analogues of the proteinase/kinase capable of acting as antagonists or agonists of the native molecules or which can act as functional analogues of the native molecules. For example, an antagonist may be a proteinase inhibitor. Chemical analogues may not necessarily be derived from the subject enzymes but may share certain conformational similarities. Alternatively, chemical analogues may be specifically designed to mimic certain physiochemical properties of the serine proteinases or kinases. Chemical analogues may be chemically synthesised or may be detected following, for example, natural product screening.

The identification of the novel molecules of the present invention permits the generation of a range of therapeutic molecules capable of modulating expression of their native counterparts or modulating their activity. Modulators contemplated by the present invention includes agonists and antagonists of proteinase/kinase expression. Antagonists of proteinase/kinase expression include antisense molecules, ribozymes and co-suppression molecules. Agonists include molecules which increase promoter ability or interfere with negative regulatory mechanisms. Agonists of proteinase/kinase include molecules which overcome any negative regulatory mechanics. Antagonists of the proteinase/kinase include antibodies and inhibitor peptide fragments.

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of proteinase/kinase in a human, said method comprising contacting the proteinase/kinase gene encoding proteinase/kinase with an effective amount of a modulator of proteinase/kinase expression for a time and under conditions sufficient to up-regulate or down-regulate or otherwise modulate expression of proteinase/kinase. For example, a nucleic acid molecule encoding proteinase/kinase or a derivative thereof may be introduced into a cell conversely, proteinase/kinase antisense sequences such as oligonucleotides may be introduced.

Another aspect of the present invention contemplates a method of modulating activity of proteinase/kinase in a human, said method comprising administering to said mammal a modulating effective amount of a molecule for a time and under conditions sufficient to increase or decrease proteinase/kinase activity. The molecule may be a proteinaceous molecule or a chemical entity and may also be a derivative of proteinase/kinase or its receptor or a chemical analogue or truncation mutant of proteinase/kinase or its receptor.

One particularly useful serine proteinase, HELA2 (testisin), is implicated in spermatogenesis and in testicular tumour development. It is proposed, in accordance with the present invention, that HELA2 (testisin) is involved in fertility and infertility.

Northern blot analysis of Poly A+RNA from normal tissue specimens showed a unique tissue distribution for HELA2 (testisin) with significant expression only in the testis. No signals are detected in any other tissue, with the exception of a minor signal in salivary gland. By RT-PCR, HELA2 (testisin) is detected in the ejaculate of normal males but not in the ejaculate of vasectomised males indicating that it is of germ cell origin. Hybridization data in situ indicated that HELA2 (testisin) is produced by immature germ cells in the testis, located near the basal epithelium and, hence, is an important factor for normal sperm maturation; defective expression or mutations would contribute to primary male infertility. Further, it is from the precursors of spermatocytes that 95% of testicular germ cell tumours, such as seminomas, embryonal carcinomas and teratocarcinomas arise. In the normal testis, germ cells undergo meiosis to become spermatocytes, but in individuals at risk, the germ cells continue to proliferate giving rise to germ cell tumours. Although not wishing to limit the present invention to any one theory or mode of action, it is proposed, in accordance with present invention, that HELA2 (testisin) functions at this critical juncture—cell growth versus maturation.

Familial forms of testicular cancer are rare, but linkage analysis of a large family with familial seminoma has demonstrated linkage to chromosome 16p, within a region adjacent to the HPKD1 (human polycystic kidney disease) gene at 16p13.3. The HELA2 (testisin) gene localises to chromosome 16p13.3 which is near the telomere of chromosome 16 and is associated with high genetic instability.

The HELA2 (testisin) gene is sandwiched between four genes which underlie other human genetic disorders; HPKD1 and tuberous sclerosis (TSC2) on the one side, and familial Mediterranean fever (MEF) and Rubenstein-Taybi syndrome (RSTS) on the other side. The question of whether HELA2 (testisin) may be a tumour suppressor for seminoma was determined by comparing HELA2 (testisin) mRNA expression in normal testes with corresponding germ cell tumours from patients with seminoma. HELA2 (testisin) was not detectable in the tumours of these patients, but was present in the corresponding normal testis specimens, indicative of a tumour suppressor role of HELA2 (testisin) in testicular germ cell cancers.

Although restricted in normal tissues to the testes, HELA2 (testisin) is expressed in tumours of the colon, pancreas, prostate and ovary. This indicates that HELA2 (testisin) contributed to tumourigenesis and, therefore, has an application as a marker and also as a therapeutic anti-tumour target in these types of cancers.

These data point to a potentially very significant role for HELA2 (testisin) in testicular germ cell maturation (spermatogenesis) as well as in the genesis of testicular germ cell tumours. In accordance with the present invention, it is proposed that expression of HELA2 (testisin) by immature germ cells may be essential for sperm cell development, such that loss of HELA2 (testisin) expression leads to continued and uncontrolled proliferation of immature germ cells leading to subsequent tumourigenesis. Germ cells wherein HELA2 (testisin) is mutated or absent may thus be prone to malignant transformation because of an inability to progress along the differentiation pathway.

HELA2 (testisin) is well-positioned to anchor on the surface of the germ cell where it would participate in a range of proteolytic activities, including cell migration, differentiation and/or activation of growth factors, receptors, or cytokines as well as initiate additional proteolytic cascades. Although not intending to limit the present invention to any one theory or mode of action, it is proposed, in accordance with the present invention, that the proteolytic target of HELA2 (testisin) is a cytokine, receptor or growth factor essential for either germ cell proliferation or differentiation—ie. HELA2 (testisin) may either inactivate a factor important for proliferation, or activate a factor which promotes differentiation. Thus, HELA2 (testisin) may be critical in the regulation of specific cytokines, cytokine receptors or growth factors by means of post-translational proteolytic processing. That HELA2 (testisin) is not present in other normal tissues of the male urogenital tract, such as the prostate and kidney, also argues for such a role specific to the testis.

Diagnostic and therapeutic applications for HELA2 (testisin) have the potential to be wide-ranging both in the cancer and fertility/infertility markets. In tumours, other than the testis, it is desirable to block or inhibit HELA2 (testisin) activity. As HELA2 (testisin) is a member of the serine proteinase family, for which prototype crystal structures are known and the catalytic mechanism reasonably well characterised, the design of drugs that target HELA2 (testisin) proteolytic activity as an anti-tumour therapy should be relatively straightforward. As HELA2 (testisin) is predicted to be anchored on the cell surface, there would not be difficulties associated with delivery of drugs to intracellular compartments. Further, it is very possible that some tumour-associated HELA2 (testisin) may be proteolytically cleaved from the surface of tumour cells, and the extracellular domain detectable in patient serum as a potential tumour associated marker.

Testicular cancer is the commonest malignancy in men aged 20–44 years. Early diagnosis correlates which an improved chance of cure and in a reduction in the seventy of treatment. If the cancer is not treated early, it becomes very aggressive. The incidence of testicular cancer is significant (9/100,000) and has been rising over the last 10 years. In testicular germ cell tumours, such as seminoma, delivery of recombinant HELA2 (testisin) using gene therapy techniques could lead to arrest of tumour growth and potentially allow commencement of normal sperm cell maturation and differentiation, thereby reducing the need for surgical removal of the testis (orchidectomy). This may be particularly effective for patients who have already had one testicle removed because of testicular cancer. The risk of contralateral testicular cancer is increased in these patients and tumour development could be arrested through early treatment with HELA2 (testisin) to arrest growth and assist maturation of germ cells. The finding of mutant forms of HELA2 (testisin) may also lead to new markers for seminoma. Unlike other testicular non-seminoma cancers where α-fetoprotein and β-HCG are frequently elevated and can be used as tumour markers, the lack of an adequate marker for seminoma creates difficulties with staging and patient follow-up.

A demonstrated role for HELA2 (testisin) in sperm maturation and development would likely lead to improved diagnosis and new directed therapeutics for male primary infertility. Primary male infertility is responsible for conception problems in 5–10% of couples and the world market for a therapeutic in this area would be very substantial. Delivery of recombinant HELA2 (testisin) could assist sperm maturation and potentially trigger normal sperm development in some of these cases. The identification of mutant forms of HELA2 (testisin) could aid in diagnosis of infertility. If HELA2 (testisin) does not prove to be a tumour suppressor, but is important for sperm maturation, it could provide a new target for the development of a male contraceptive. If hormonal regulation of HELA2 (testisin) can be demonstrated, HELA2 (testisin) may prove effective for the treatment of conditions arising from dysfunctional hormal responses, such as cryptorchidism, which is associated with both infertility and seminoma development.

Accordingly, the present invention contemplates a pharmaceutical composition comprising proteinase/kinase or a derivative thereof or a modulator of proteinase/kinase expression or proteinase/kinase activity and one or more pharmaceutically acceptable carriers and/or diluents. These components are referred to as the "active ingredients" and include, for example, HELA2 (testisin).

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimersal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 $\mu$g and 2000 mg of active compound.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Parental compositions are generally suitable for administration by the intravenous, subcutaneous or intramuscular routes amongst other routes of administration. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail. Other forms of administration include but are not limited to intranasal, buccal, rectal, suppository, inhalation, intracerebral and intraperitoneal.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients. The effective amounts include amounts calculated or predicted to have the desired effect and range from at least about 0.01 ng/kg body weight to about 10,000 mg/kg body weight. Alternative amounts include 0.1 ng/kg body weight to about 1000 ng/kg body weight.

The pharmaceutical composition may also comprise genetic molecules such as a vector capable of transfecting target cells where the vector carries a nucleic acid molecule capable of modulating proteinase/kinase expression or proteinase/kinase activity. The vector may, for example, be a viral vector. This form of therapy is proposed to be particularly useful for gene replacement or enhancement therapy for HELA2 (testisin) especially for the modulation of fertility and/or treatment of testicular cancer.

Still another aspect of the present invention is directed to antibodies to proteinase/kinase and its derivatives. Such antibodies may be monoclonal or polyclonal and may be selected from naturally occurring antibodies to proteinase/kinase or may be specifically raised to proteinase/kinase or derivatives thereof. In the case of the latter, proteinase/kinase or its derivatives may first need to be associated with a carrier molecule. The antibodies and/or recombinant proteinase/kinase or its derivatives of the present invention are particularly useful as therapeutic or diagnostic agents. For example, monitoring non-testicular cancer by measuring HELA2 (testisin) or screening for the presence of testicular cancer by an absence of HELA2 (testisin).

Proteinase/kinase and its derivatives may also be used to screen for naturally occurring antibodies to proteinase/kinase. These may occur, for example in some autoimmune diseases. Alternatively, specific antibodies can be used to screen for proteinase/kinase. Techniques for such assays are well known in the art and include, for example, sandwich assays and ELISA. Knowledge of proteinase/kinase levels may be important for diagnosis of certain cancers or a predisposition to cancers or for monitoring certain therapeutic protocols.

Antibodies the proteinase/kinase of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimen.

For example, specific antibodies can be used to screen for proteinase/kinase proteins. The latter would be important, for example, as a means for screening for levels of proteinase/kinase in a cell extract or other biological fluid or purifying proteinase/kinase made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immnunoglobulin antibody. An antibody as contemplated herein includes any antibody specific to any region of proteinase/kinase.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of proteinase/kinase, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting proteinase/kinase in a biological sample from a subject said method comprising contacting said biological sample with an antibody specific for proteinase/kinase or its derivatives or homologues for a time and under conditions sufficient for an antibody-proteinase/kinase complex to form, and then detecting said complex.

The presence of proteinase/kinase may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain proteinase/kinase including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the proteinase/kinase or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from about room temperature to about 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionucleotide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect proteinase/kinase gene or its derivatives. Alternative methods or methods used in conjunction include direct nucleotide sequencing or mutation scanning such as single stranded conformation polymorphoms analysis (SSCP), specific oligonucleotide hybridisation, and methods such as direct protein truncation tests.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli,* Bacillus sp and Pseudomonas sp. Preferred eukaryotic cells include yeast, fungal, mammalian and insect cells.

Accordingly, another aspect of the present invention contemplates a genetic construct comprising a vector portion and a mammals and more particularly a human proteinase/kinase gene portion, which proteinase/kinase gene portion is capable of encoding an proteinase/kinase polypeptide or a functional or immunologically interactive derivative thereof.

Preferably, the proteinase/kinase gene portion of the genetic construct is operably linked to a promoter on the vector such that said promoter is capable of directing expression of said proteinase/kinase gene portion in an appropriate cell.

In addition, the proteinase/kinase gene portion of the genetic construct may comprise all or part of the gene fused to another genetic sequence such as a nucleotide sequence encoding glutathione-S-transferase or part thereof.

The present invention extends to such genetic constructs and to prokaryotic or eukaryotic cells comprising same.

The present invention also extends to any or all derivatives of proteinase/kinase including mutants, part, fragments, portions, homologues and analogues or their encoding genetic sequence including single or multiple nucleotide or amino acid substitutions, additions and/or deletions to the naturally occurring nucleotide or amino acid sequence. The present invention further encompasses hybrids between the proteinase/kinases such as to broaden the spectrum of activity and to ligands and substrates of the proteinase/kinase.

The proteinase/kinase and its genetic sequence of the present invention will be useful in the generation of a range of therapeutic and diagnostic reagents.

Soluble proteinase/kinase polypeptides or other derivatives, agonists or antagonists are also contemplated to be useful in the treatment of disease, injury or abnormality in the nervous system, e.g. in relation to central or peripheral nervous system to treat Cerebral Palsy, trauma induced paralysis, vascular ischaemia associated with stroke, neuronal tumours, motoneurone disease, Parkinson's disease, Huntington's disease, Alzheimer's disease, Multiple Sclerosis, peripheral neuropathies associated with diabetes, heavy metal or alcohol toxicity, renal failure and infectious diseases such as herpes, rubella, measles, chicken pox, HIV or HTLV-1. Other conditions for which the proteinase/kinase are useful include cancer, metastasis and autoimmune disease amongst many others. Particular applications for HELA2 (testisin) include as a marker for non-testicular cancers, in the treatment of testicular cancer and in the treatment of infertility or in inducing infertility such for contraception.

A further aspect of the present invention contemplates the use of proteinase/kinase or its functional derivatives in the manufacture of a medicament for the treatment of proteinase/kinase mediated conditions defective or deficient.

The present invention is further described by the following non-limiting Examples.

EXAMPLE 1

Cloning Procedures

In order to identify serine proteinases that may be involved in regulatory cellular functions, a genetic screening approach was applied using degenerate primers corresponding to conserved regions of serine proteinases (amino acids flanking His- and Ser-residues) to amplify gene fragments spanning these regions from cDNA, using a low stringency RT-PCR (Reverse Transcriptase-Polymerase Chain Reaction) approach.

By this technique, the aim was to isolate low abundance genes as well as those present in moderate to high abundance. The cDNA used for these experiments was isolated from a HeLa cell cytotoxicity model wherein PAI-2 expression inhibits TNF(-induced apoptosis (Dickinson et al *J. Biol. Chem.* 270: 27894–27904, 1995). These PAI-2 expressing cells provide a unique and viable system for investigating TNF(signalling pathways as they are protected from the cytotoxic effects of TNF).

cDNA was generated from RNA isolated from HeLa cells and PAI-2 expressing HeLa cells, both untreated and following treatment with TNF and cycloheximide. Amplification of each cDNA population using PCR and the following serine proteinase degenerate primers, His Primer: 5'ACAGAATTCTGGGTIGTI-ACIGCIGCICAYTG3' [SEQ ID NO:1], Ser Primer: 5'ACAGAATTCAXIGGICCICCIC/GT/AXTCICC3' [SEQ ID NO:2]

(where X=A or G; Y=C or T; I=Inosine) produced DNA fragments in the range of 480 bp, the approximate predicted size of the serine proteinase intergenic region. These amplified DNA fragments were cloned into *E. coli* generating a library containing approximately 150 independent clones. The inventors analysed 36 of these clones and found that 9 encoded previously identified serine proteinases or tissue-type or urokinase-type plasminogen activators, thereby demonstrating the efficacy of this approach. Of the other 36, two were found to encode novel open reading frames with high homology to serine proteinases and are referred to herein as "HELA2" (or "testisin") and "ATC2". One additional clone designated herein, "BCON3", showed homology to a kinase. Extension of the DNA fragments by RACE in both 5' and 3' directions using internally derived primers has verified the homology of HELA2 and ATC2 to the serine proteinase family. Each of the three DNA sequences are unique in that they are markedly different from any known DNA or protein sequence in the Genbank and NBRF databases.

EXAMPLE 2

HELA2 Serine Proteinase (Testisin)

The HELA2 mRNA transcript is approximately 1.5 kb as determined from Northern blot analysis. Nucleic acid sequence was obtained for about 1.1 kb of HELA2 which spans the entire coding region, the 3' noncoding region and part of the 5' noncoding region. The coding region starts with an ATG codon which is present in a motif analogous to the Kozak eukaryotic translation initiation consensus sequence. Alignment of the deduced amino acid sequence of HELA2 with homologous serine proteinases shows that the cDNA encodes a 314 amino acid (aa) polypeptide with a calculated molecular weight of 34.8 kD (called Testisin), which is synthesized as a zymogen containing pre-, pro- and catalytic regions (FIG. 1). The pro-region (or light chain) and the catalytic region (heavy chain) are delineated by a classic serine proteinase activation motif Arg-Ile-Val-Gly-Gly (SEQ ID NO:24) with cleavage likely occurring between Arg and Ile. The catalytic region includes the catalytic triad of His, Asp and Ser in positions and motifs which are highly conserved among the serine proteinases. Ten Cys residues occur in conserved positions: by analogy to other serine proteinases, eight of these function to form disulfide bridges within the catalytic region and the remaining two link the pro- and catalytic regions.

Structural features conserved in the binding pockets of serine proteinases are present in HELA2 (testisin). An Asp residue at the bottom of the serine proteinase binding pocket six residues before the active site Ser in HELA2 (testisin) indicates that HELA2 (testisin) has trypsin-like specificity, with proteolytic cleavage after Arg or Lys in target substrates. HELA2 (testisin) also contains a conserved Ser-Trp-Gly motif at the top of the binding pocket which is likely involved in hydrogen bonding with target substrates in other serine proteinases.

A hydrophobicity plot of the HELA2 (testisin) amino acid sequence (FIG. 1) identifies two hydrophobic regions, one located at the amino terminus and the other at the carboxy terminus. The 20 aa amino terminal hydrophobic region is likely to be a signal peptide, which would direct newly synthesized HELA2 to enter the endoplasmic reticulum. The 16 aa hydrophobic carboxy terminus of HELA2 (testisin) shows high homology to the transmembrane domain of prostasin (FIG. 2), suggesting that HELA2 (testisin) is likely to be a membrane-anchored serine proteinase. Thus HELA2 (testisin) may anchor on the germ cell surface where it could participate in a range of proteolytic activities, including participation in cell migration, differentiation and/or activation of growth factors and proteolytic cascades. In prostasin, this protruding carboxy terminus may be cleaved, thus releasing the serine proteinase from the membrane. A similar cleavage event may also occur with Testasin.

Two isoforms of HELA2 were identified in a HeLa cell cDNA library (Stratagene UniZap HeLa Library) which differ by an insertion of 6 nucleotides which generates a Sfi1 restriction enzyme site. At the protein level, there is a corresponding insertion of 2 aa's (Tyr-Ser) within the catalytic binding pocket (FIG. 2A). The two isoforms of HELA2 cDNA are referred to as the short (S) and long (L) isoforms, respectively. The nucleotide and corresponding amino acid sequence for the short isoform of HELA2 is shown in SEQ ID NOs. 3 and 4, respectively. The long isoform is shown in SEQ ID NOs:5 and 6, respectively.

EXAMPLE 3

Generation of Full Length cDNA Encoding HELA2 (Testisin)

Figure 3I:
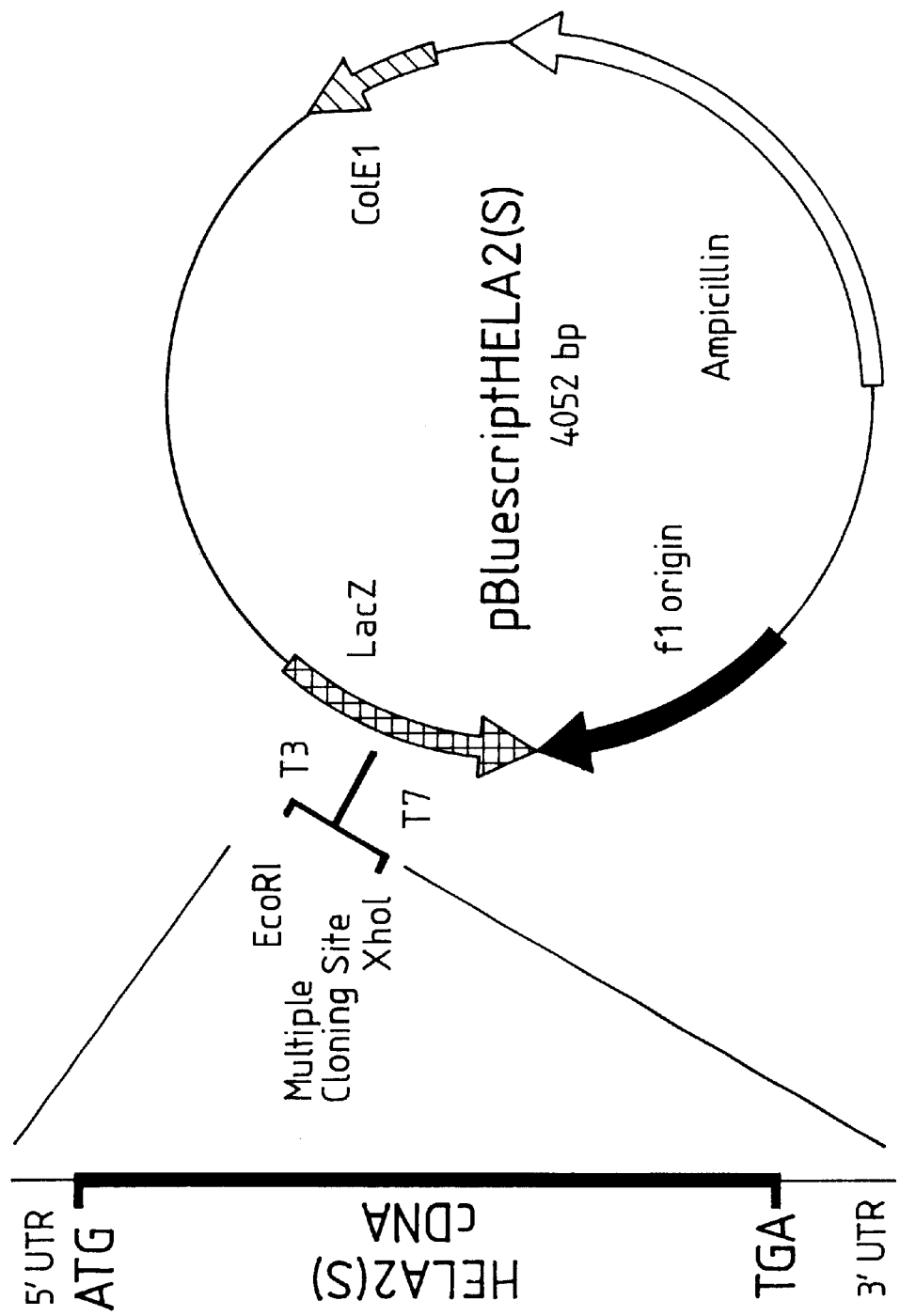
FIGS. 3(I)–III are a diagrammatic representations of plasmid constructs pBluescriptHELA2(S) and pBluescriptHELA2(L) containing full length cDNAs for testsin (short isoform (S)) and testisin (long isoform (L)), respectively.
Figure 3:
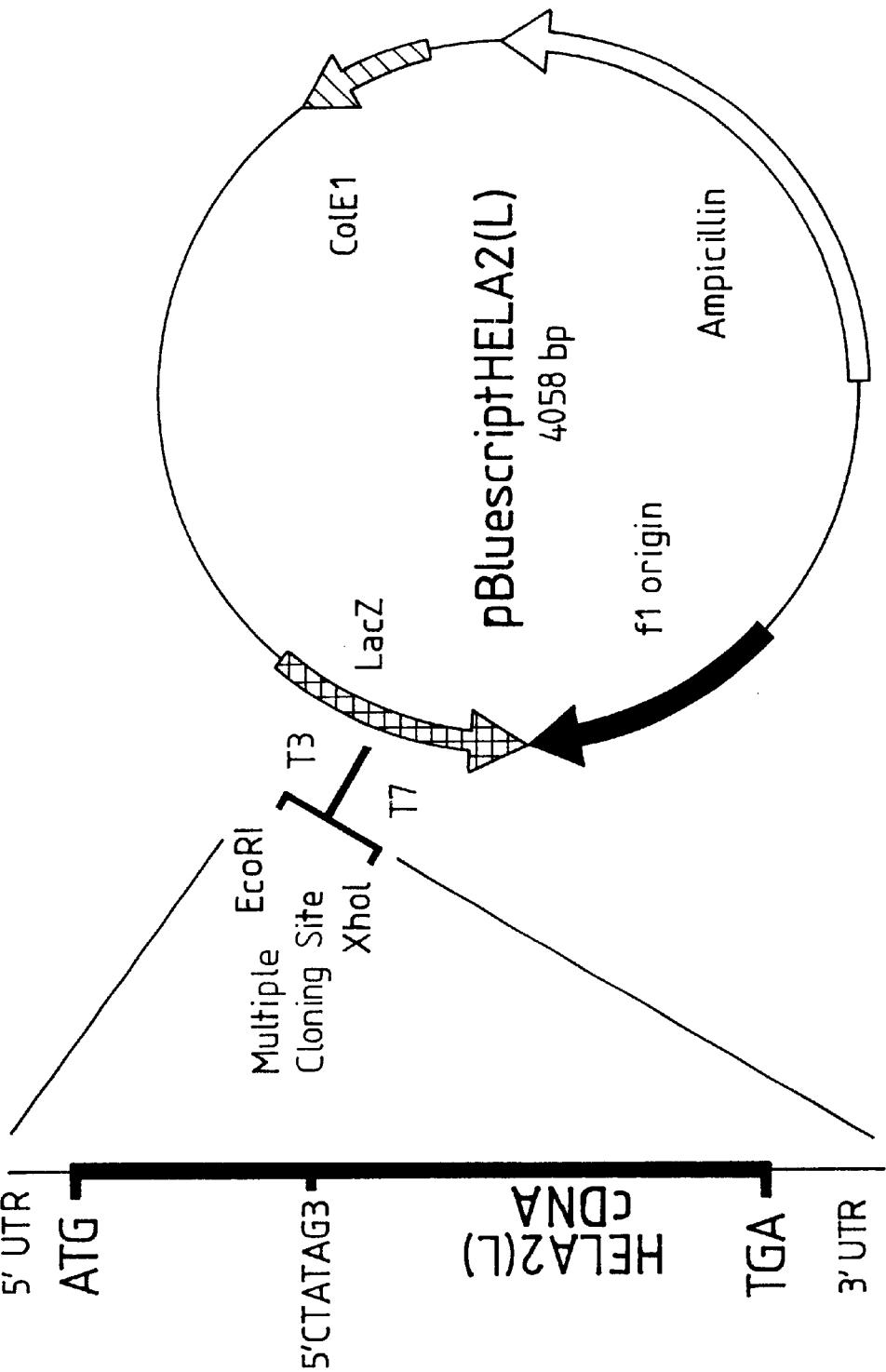

Partial cDNA fragments of the short and long isoforms of HELA2 were obtained using a combination of library screening techniques. Plasmids containing the full length cDNA of the two isoforms were then generated in pBluescriptSK(−) by ligating restriction enzyme-digested fragments of the partial cDNAs. A plasmid map of the two generated constructs, pBluescriptHELA2(S) and pBluescriptHELA2(L), and a restriction enzyme map of the long isoform cDNA are diagrammed in FIG. 3.

In vitro transcription/translation using HELA2 cDNA shows a major specific product of approximately 35 kD (FIG. 2B), which is the same as size predicted from the open reading frame, demonstrating that HELA2 cDNA encodes a protein. The translation/transcription coupled rabbit reticulocyte lysate system (Promega) was used as per the manufacturer's instructions for 35S-methionine labelling. Clones of HELA2 in pBluescript a PAI-2 positive control were used with T3-RNA polymerase (sense direction).

EXAMPLE 4

Expression of Recombinant HELA2 (Testisin) in *E.coli*

(A) Generation of Expression Constructs (i) His(6)-tagged Recombinant HELA2 (Testisin)

To reduce potential toxic effects on host cells, and therefore optimise expression, a strategy was employed to eliminate the hydrophobic residues of the secretary and membrane anchoring domains of HELA2 (testisin) (Testisin (20–295)). Testisin (20–295) fragments which were His6 tagged at either the amino or carboxy terminal were obtained by PCR and expression constructs were generated by inserting these into pQE vectors (Qiagen).

The primers used to generate the amino-terminal tagged protein were:

forward: 5' GCACAGTCGACCAAGCCGGAGTCGCAGAG 3' [SEQ ID NO:11] and reverse: 5' GCACAAAGCTTGCCAGGAGGGGTCTGGCTG 3' [SEQ ID NO:12]

Figure 4I:
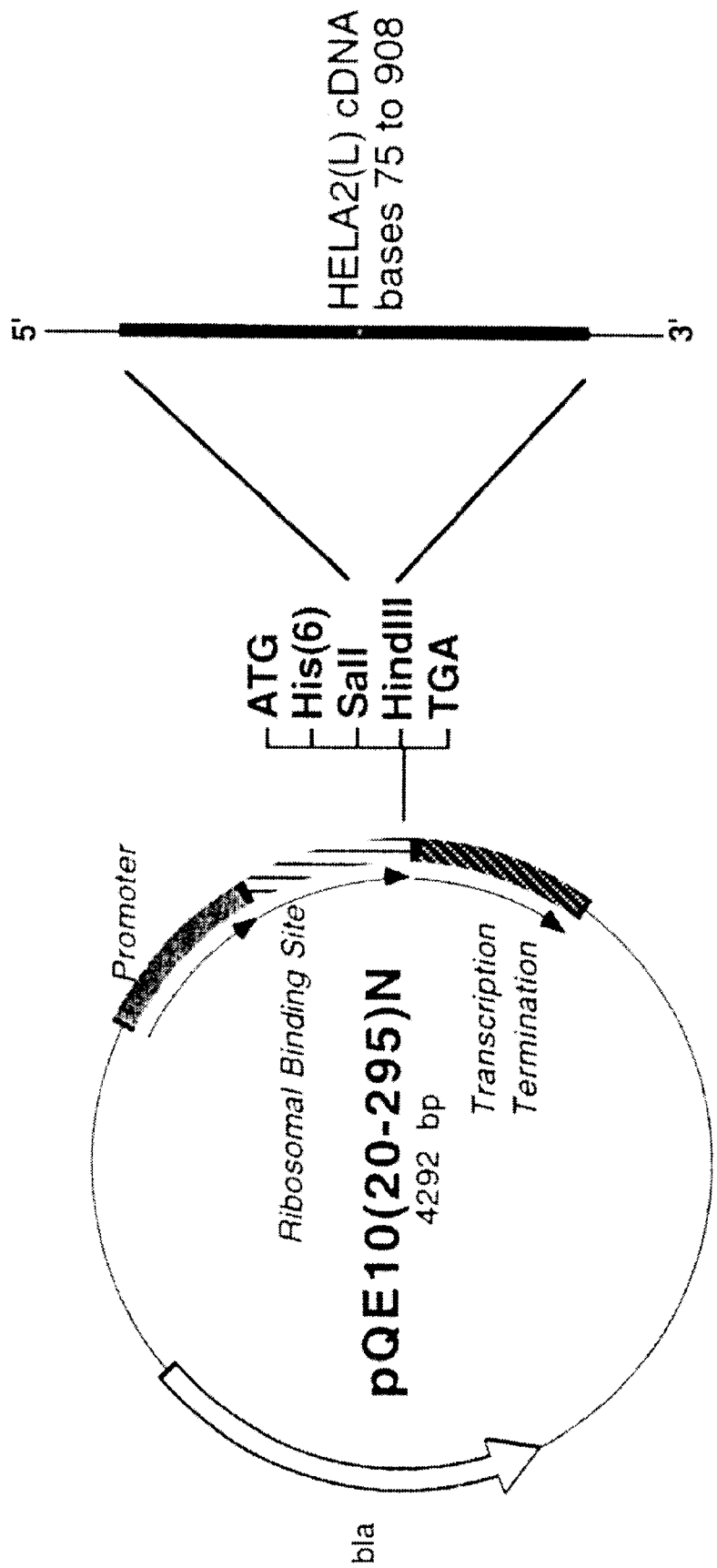
FIGS. 4(I)–(III) are a diagrammatic representation of plasmid constructs pQET(20–295)N and pQET(20–295)C, wherein the hydrophobic residues of testisin were removed and the remaining sequences cloned into pQE prokaryotic expression plasmids; plasmids pGEX-1 (90–279) comprising a carboxy terminal part of testisin fused to glutathione-S-transferase.
Figure 4:
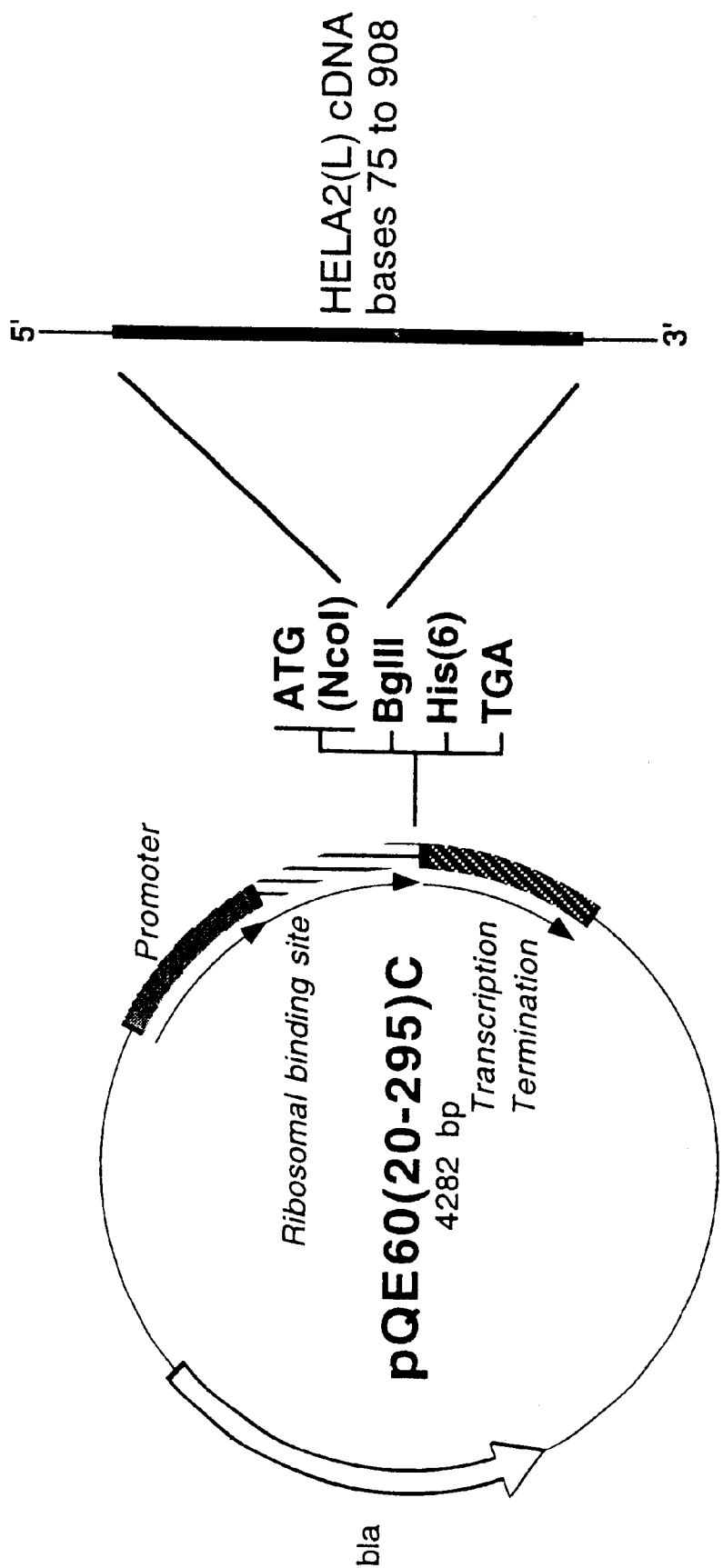

The amplification product of 858 bp was digested with SalI and HindIII and ligated into pQE-10 to give pQE-10 (20–295)N (FIG. 4).

The primers used to generate the carboxy-terminal tagged protein were:

forward: 5' GCACAACCATGGCCAAGCCGGAGTCGCAGGAG 3' [SEQ ID NO:13] and reverse 5' GCACAAGATCTCCAGGAGGGGTCTGGCTG 3' [SEQ ID NO:14].

The amplification product of 859 bp was digested with NcoI and BglII and ligated into PQE-60 to give pQE-60 (20–295)C (FIG. 4).

(ii) GST-tagged Recombinant HELA2 (Testisin)

In order to generate a fusion of glutathione-S-transferase (GST) and HELA2 (testisin), pBluescriptHELA2(S) was digested with Sau3A1, releasing a 570 bp DNA fragment encoding the 190 amino acids at the carboxy terminal end of HELA2 (testisin). This DNA fragment was cloned into the BamH1 site of pGEX-1 generating pGEX-1(90–279) (FIG. 4) and subjected to DNA sequence analysis to confirm that the fusion was in frame.

(b) Expression of His-tagged HELA2 (Testisin) in *E. coli* pQE10(20–295)N and pQE60(20–295)C plasmids were electro-transformed into *E. coli* DH5( cells. Four different clones were selected for further analysis: His-N21 expressing amino terminal His6-tagged Testisin (20–295); and His-C21, His-C22, and His-C23 expressing carboxy terminal His6-tagged Testisin (20–295). To express recombinant HELA2 (testisin) protein, transformed cells were grown to log phase then induced for 4 hours in the presence of 2 mM IPTG. Cells were lysed in a denaturing lysis buffer containing 8M urea, 0.1M NaH2PO4 and 0.01M Tris/HCl pH8. Alternatively the cells were lysed in a non-denaturing lysis buffer containing 0.1M NaH2PO4, 0.1M NaCl and 0.01 M Tris/HCl pH8. The His6 tagged protein was recovered by mixing the lysate with a metal affinity resin (Qiagen or Clontech). Purified testisin(L) was eluted with 100 mM EDTA in lysis buffer (pH 6.3). A major band of approximately 32 kDa was obtained in the eluate as shown by the arrows in FIG. 5A. Western blot analysis of a purification of the His-C23 clone using an anti-His6 antibody showed that the band at 32 kDa was His6 tagged HELA2 (testisin) (FIG. 5B).

EXAMPLE 5

Figures 6, 6I, 6II, 6III:
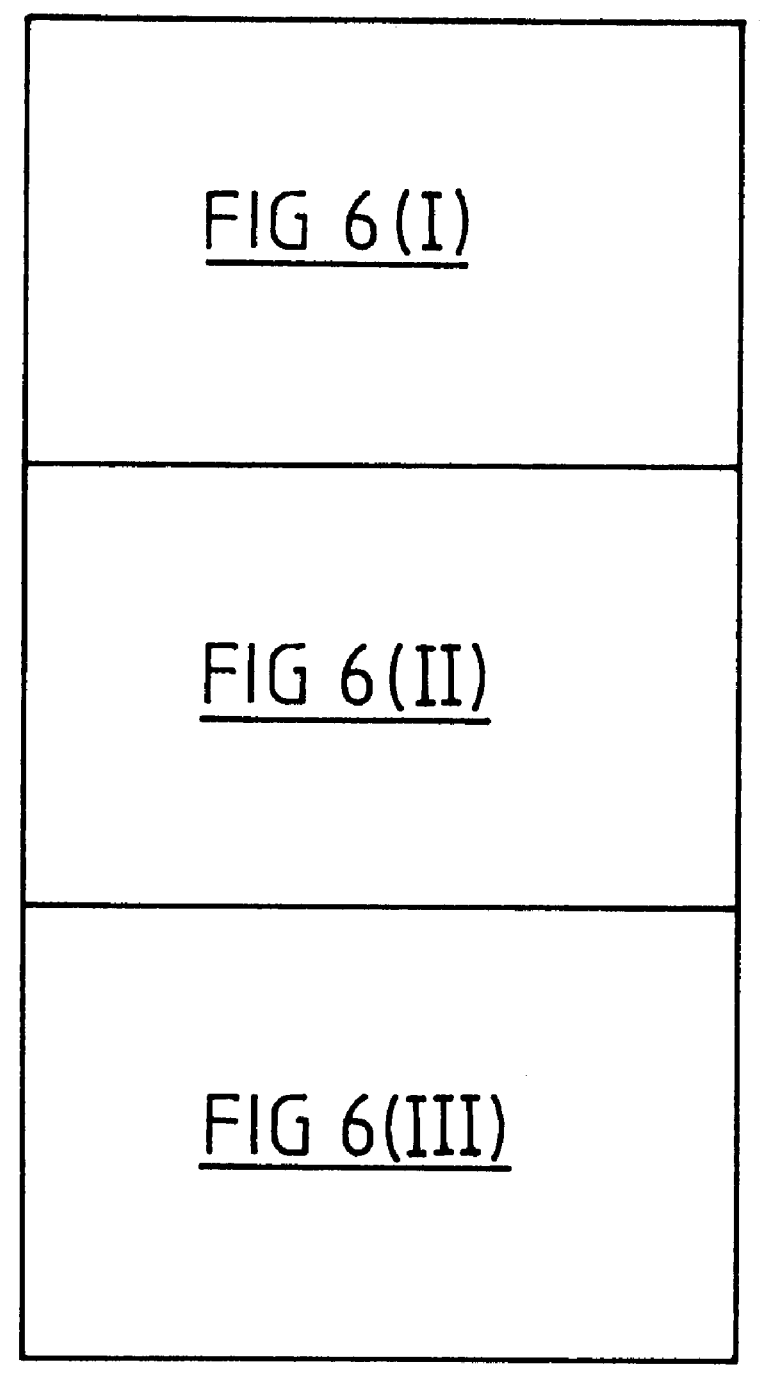

Immunology (A) Rabbit Polyclonal Antibodies Directed Against HELA2 (Testisin) Peptide Antigens Three peptides were selected from the HELA2 (testisin) amino acid sequence on the basis of predicted antigenicity, hydrophilicity and lack of identity with known proteins (FIG. 6).

Peptide antigen T20–33 KPESQEAAPLSGPC [SEQ ID NO:15]

Peptide antigen T46–63 EDAELGRWPWQGSLRLWDC [SEQ ID NO:16]

Peptide antigen T175–190 GYIKEDEALPSPHTLQC [SEQ ID NO:17]

These peptides were synthesized (Auspep) and coupled to keyhole limpet hemocyanin. The coupled peptide (500 Fg) in PBS (0.5 ml) was emulsified in an equal volume of Freund's complete adjuvant before injection into a rabbit. Booster injections of coupled peptide in Freund's incomplete adjuvant were made at intervals of 2 to 3 weeks. Each rabbit was bled (approximately 1 ml) before the initial injection and about 7 days after the second and subsequent boosters and the antibody titre assessed by direct ELISA assay. Immunoreactive antisera against the peptide antigens was demonstrated and when a sufficiently high titre was achieved (after 3 to 5 boosters), between 12 and 25 ml of blood was removed from each animal.

Figure 7:
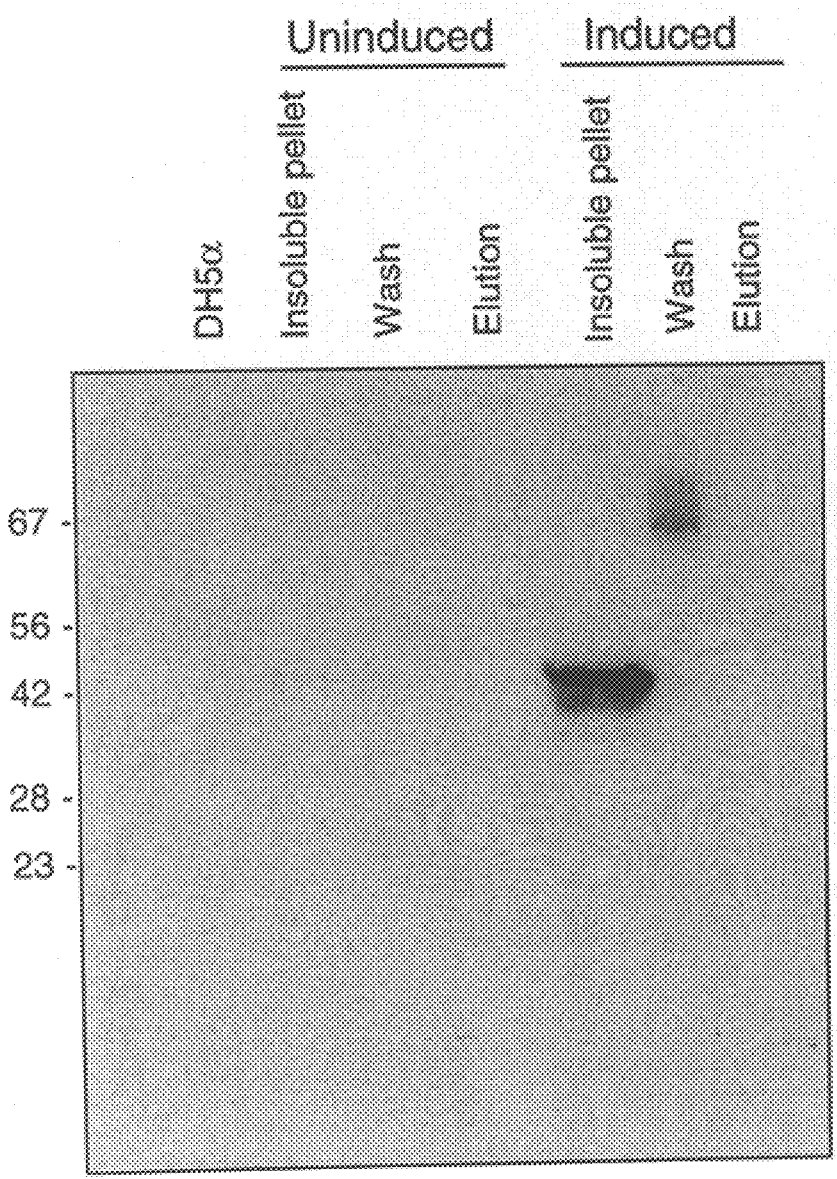
FIG. 7 is a photographic representation of a Western blot of GST-HELA2 (testisin) fusion protein purified by affinity chromatography.

Rabbit antisera was affinity purified against the respective immunising peptides by chromatography using peptide-coupled affinity columns. Immunoreactivity of the affinity purified antibodies against HELA2 (testisin) was demonstrated by Western blot analysis of GST-tagged recombinant HELA2 (testisin). pGEX-1(90–279) plasmid DNA (described in Example 4) was electro-transformed into *E. coli* DH5(cells and induced for 3 hours in the presence of 0.5 mM IPTG. Cells were lysed in 1.5% sarcosyl, 2% Triton X100 and then sonicated. After removal of the insoluble fraction by centrifugation, the cell lysate was mixed with a 50% slurry of Glutathione Sepharose 4B, washed, and the purified GST-Testisin(90–279) was eluted by boiling with SDS-Sample buffer. FIG. 7 shows an example of Western blot analysis of the eluate using anti-Peptide T175–190 antibody demonstrating a purified, immunoreactive band representative of GST-linked HELA2(testisin) of approximately 47 kDa.

(B) Rabbit Polyclonal Antibodies Directed Against Purified Bacterially Expressed HELA2 (Testisin)

An SDS-PAGE gel slice containing purified His6 tagged HELA2 (testisin) (as described in Example 4, part (b)) is to be combined with adjuvant and rabbits immunized as described above. Rabbit antisera are tested by Western blot analysis for immunoreactivity against purified recombinant HELA2 (testisin) and HELA2 (testisin) in cell extracts, as well as use in immunohistochemical analyses.

EXAMPLE 6

Expression of HELA2 (Testisin) in Eukaryotic Cells (A) Generation of Expression Constructs Eukaryotic expression constructs encoding testisin(s) and testisin(L) His6 tagged at the carboxy terminal were generated in the eukaryotic expression vector pcDNA3 (Invitrogen). DNA fragments encoding HELA2 (testisin) were generated by PCR from both pBluescriptHELA2(S) and pBluescriptHELA2(L) using the primers:

forward: 5' GCACAGGTACCGAGGCCATGGGCGCGCGC 3' [SEQ ID NO:18] and reverse 5' GCACATCTAGATCAGTGGTGGTGGTGGTGGTGGACCGGCCCCAGGA GTGG 3' [SEQ ID NO:19]

Figure 8I:
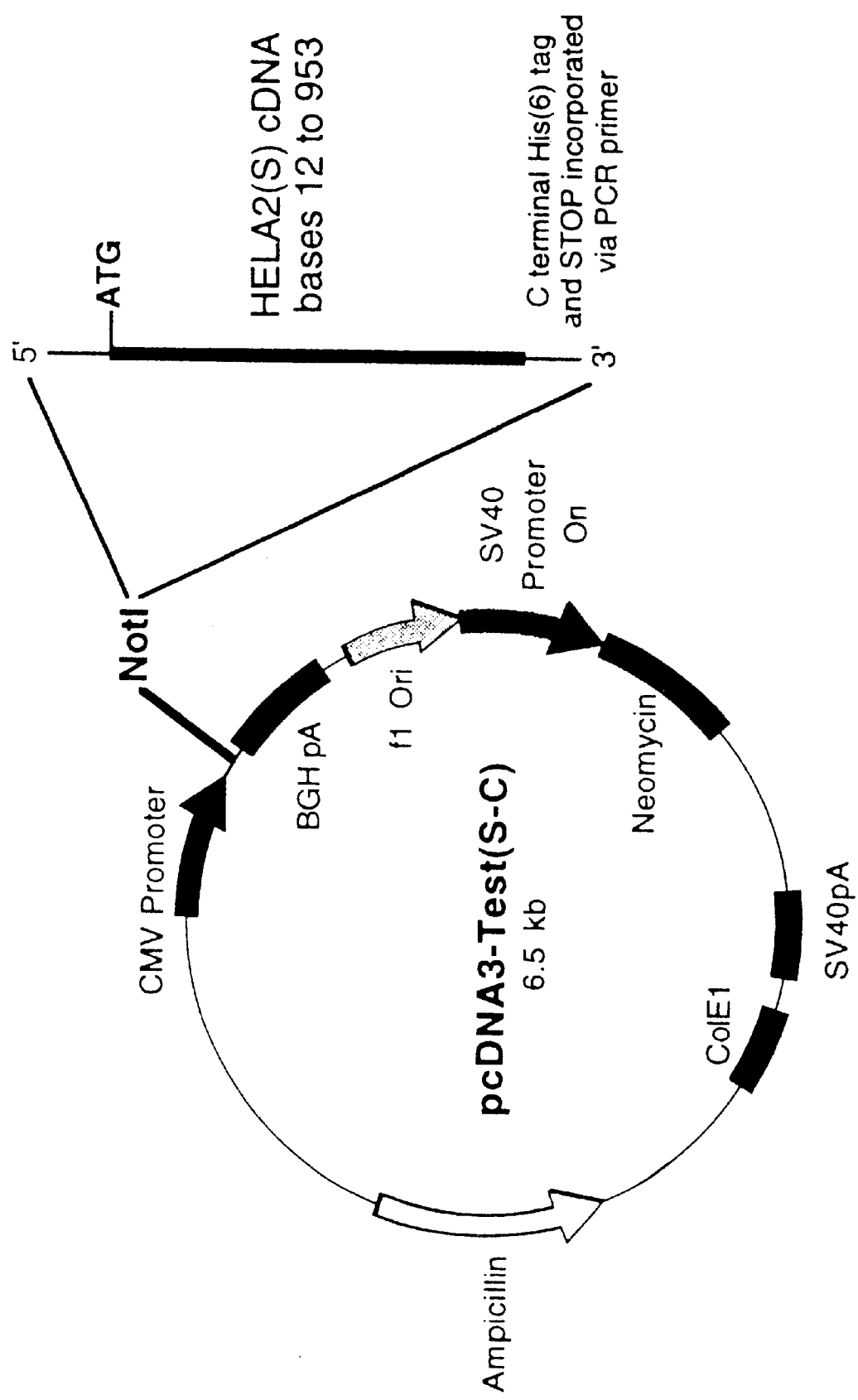
FIGS. 8(I)–(III) are diagrammatic representations of eukaryotic expression constructs, pcDNA3-Test(S-C), pcDNA3-Test(L-C) and pcDNA3-Test(1–297)L-C.
Figure 8:
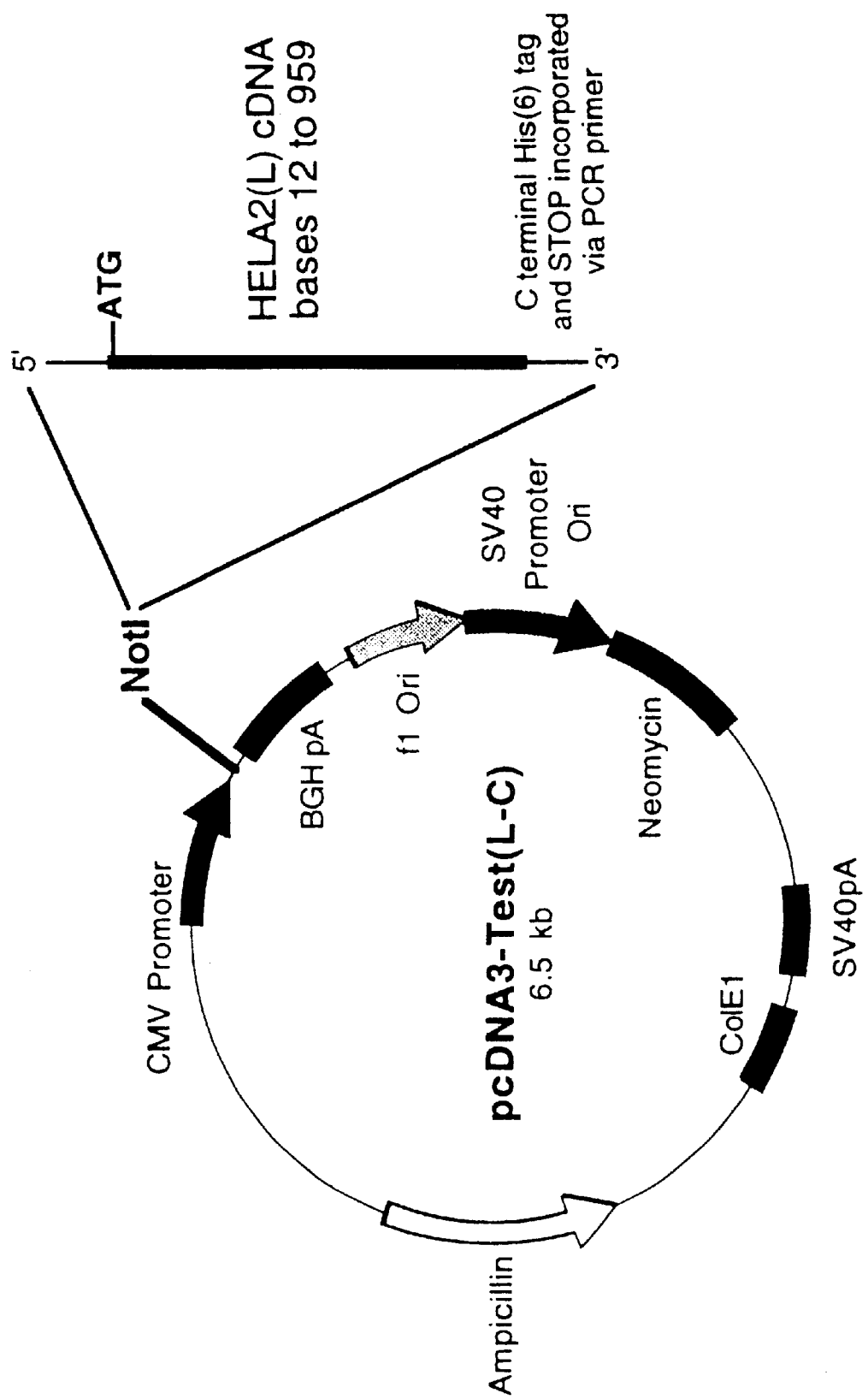

The PCR product of 985 bp obtained from amplification of HELA2 (testisin) from pBluescriptHELA2(S) as template was ligated into pGEM-T (Easy) vector (Promega). Digestion of this shuttle construct with NotI released a 1025 bp fragment which was ligated into pcDNA3 generating the short isoform expression construct pcDNA3-Test(S-C) (FIG. 8). PCR amplification of the long isoform template gave a 991 bp product which was ligated into pGEM-T (easy) vector. NotI digestion of the shuttle construct released a 1031 bp fragment which was ligated into pcDNA3 giving pcDNA3-Test(L-C) (FIG. 8).

Soluble testisin (1–295)-His6 in which the membrane anchoring sequence is deleted and the protein is carboxy-His6 tagged is to be obtained by PCR amplification of HELA2 (testisin) from pBluescriptHELA2(L) using the primers:

forward: 5' GCACAGCGGCCGCGAGGC-CATGGGCGCGCGC 3' [SEQ ID NO:20] and reverse: 5' GCACAGCGGCCGCTCAGTGGTGGTG-GTGGTGGTGCCAGGAGGGGTC TGGCTG 3' [SEQ ID NO:21].

The PCR product will be digested with NotI and ligated into pcDNA3 generating the long isoform expression construct pcDNA3-Test(1–295)L-C (FIG. 8).

(B) Expression and Cellular Localisation of HELA2 (Testisin)

Each of the expression constructs is transiently transfected into a eukaryotic cell line (eg. HeLa, CHO or COS cells) by electroporation. Expression is confirmed by Northern blot and immunoblot. The His6 tag is a small, uncharged tag which reportedly does not interfere with cellular membrane interactions and is able to be detected with anti-His6 antibodies. HELA2 (testisin) cellular localisation is analysed by immunofluorescence using antibodies directed against the His6 tag and stained cells examined by confocal microscopy. Mock transfected cells is monitored as one of the controls in these experiments. Cells are examined under non-permeablised and permeabilised conditions to investigate intracellular and cell surface expression of HELA2 (testisin) tagged proteins. Possible release of HELA2 (testisin) into the supernatant is monitored by immunoblotting of conditioned media. Association of HELA2 (testisin) with a particular cellular compartment is confirmed by cellular fractionation studies. Stable transfectants of the full length and truncated tagged HELA2 (testisin) is generated by selection in G418. Recombinant HELA2 (testisin) is purified from these stable transfectants using a metal affinity resin (eg. Qiagen or Clontech) for assay of its bioactivity and efficacy as a therapeutic reagent.

EXAMPLE 7

Figure 9I:
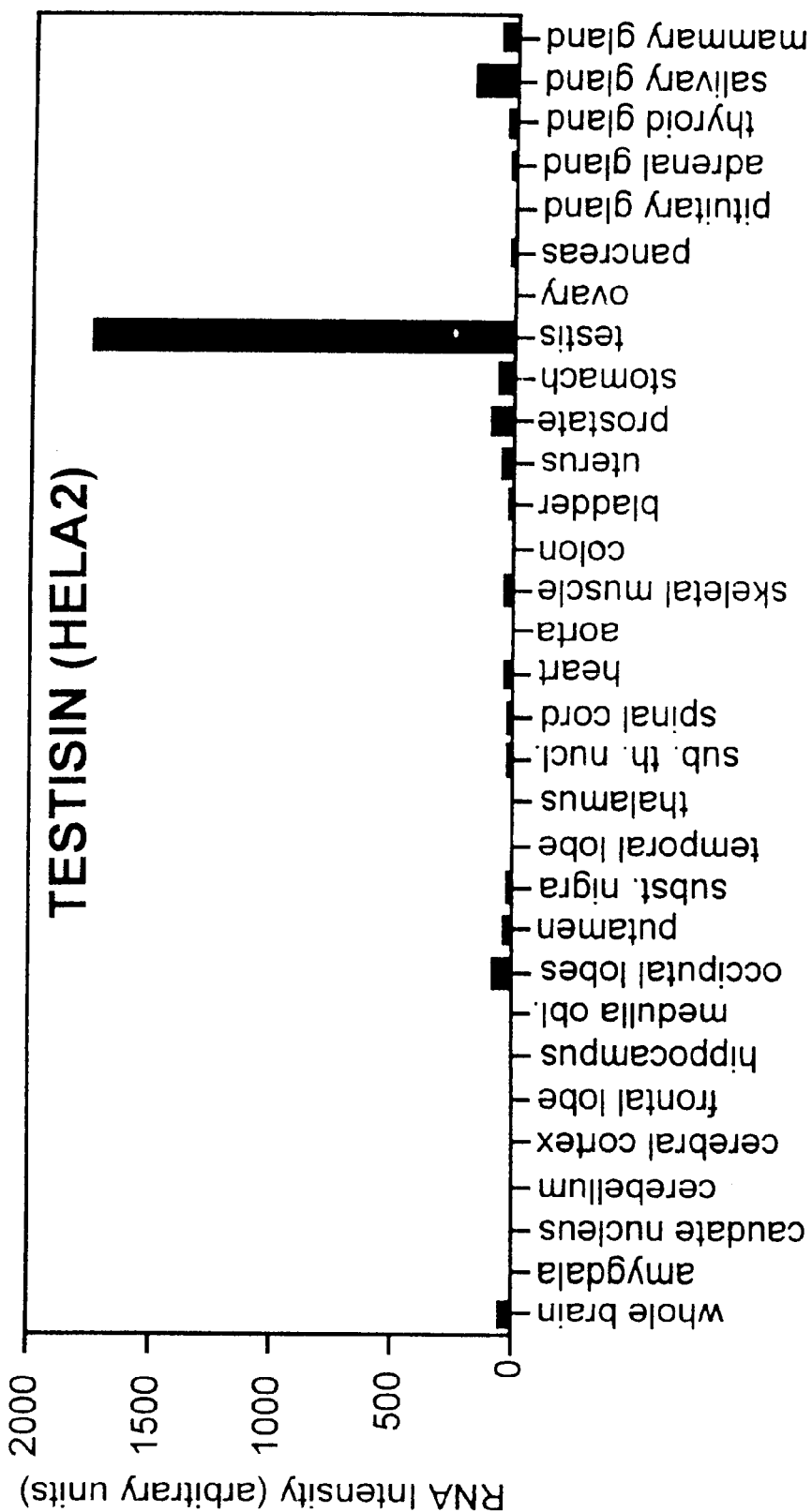
FIGS. 9(I)–9(III) are a diagrammatic representations showing a histogram of the signal intensity from a Clontech Master RNA blot of the tissue distribution of HELA2 (testisin) in RNA from 50 different normal tissues. (I–II) Probed with HELA2 (testisin) specific probe; (III–IV) Probed with BCON3 specific prove which is ubiquitously expressed. The 8 tissues on the right hand side of the diagram are the control (negative) samples.
Figure 9:
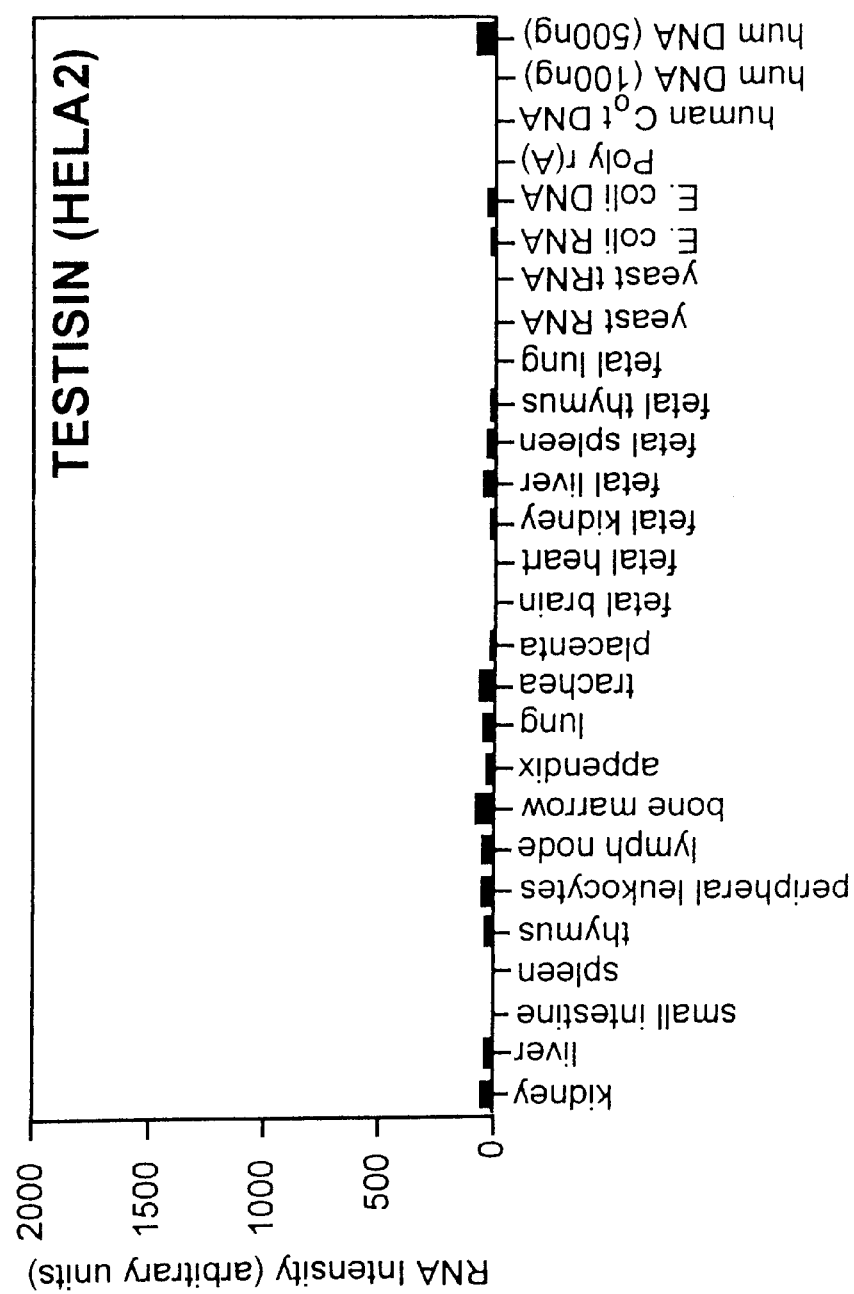
Figure 9:
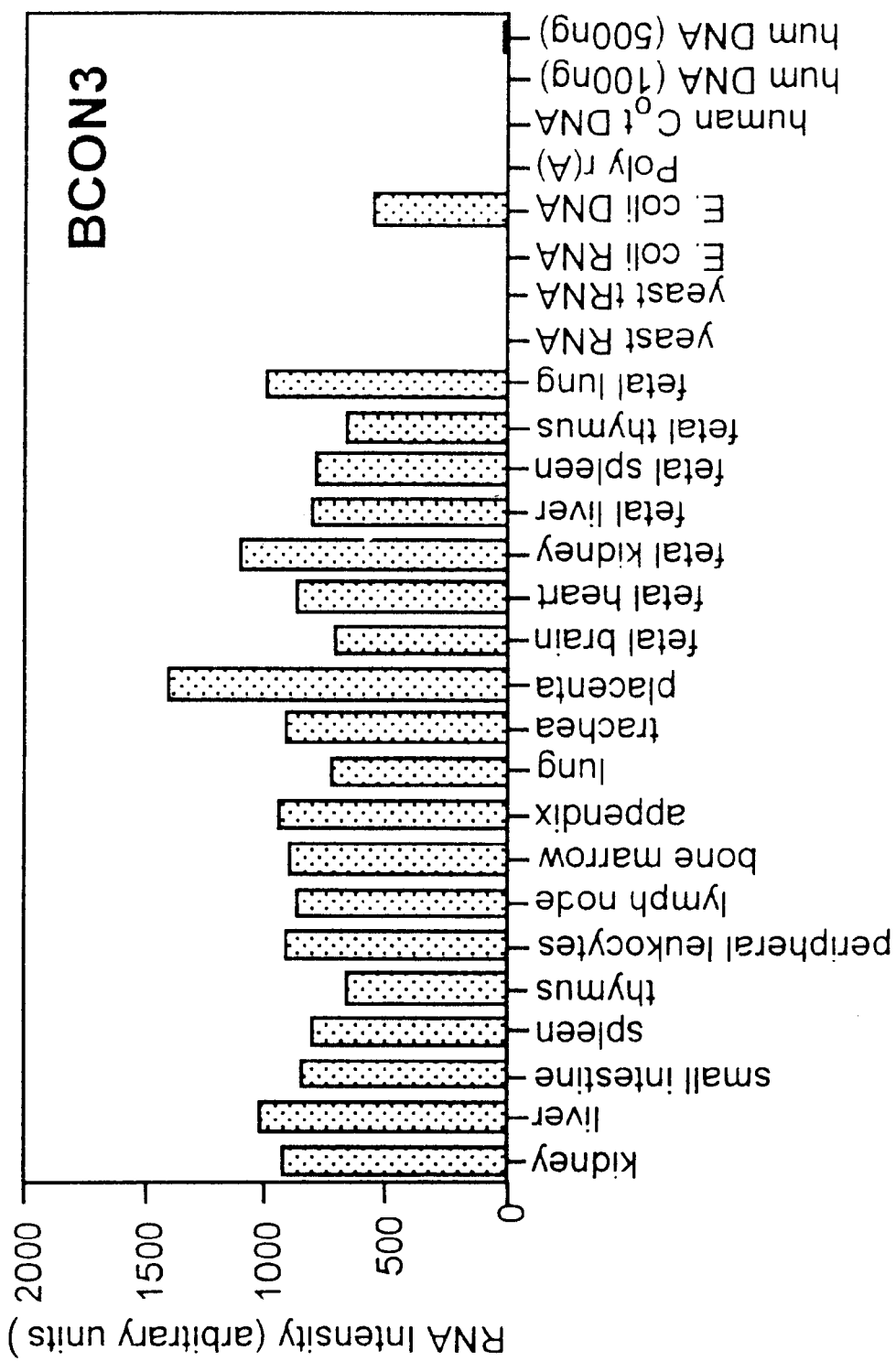

HELA2 (Testisin) is Specifically Expressed in the Normal Testis, and is Associated with Sperm Development (A) Normal Tissue Blot Dot blot analysis of PolyA+RNA from 50 normal tissue specimens (strandardised to 8 different housekeeping genes) (Clontech) was performed using a 32P-labelled HELA2 (testisin) probe. Hybridization of the radiolabelled probe was in ExpressHyb solution (Clontech) at 65°. The blots were washed to a final stringency of 0.1×SSC/0.5% w/v SDS. High level expression of HELA2 (testisin) was found only in the testis as shown by the histogram plot of the Signal Intensity in FIG. 9. In contrast, probing of the same blot with BCON3 showed ubiquitous expression of BCON3 mRNA in a variety of tissues (FIG. 9).

(B) Multiple Tissue Northern Blot

Figure 10:
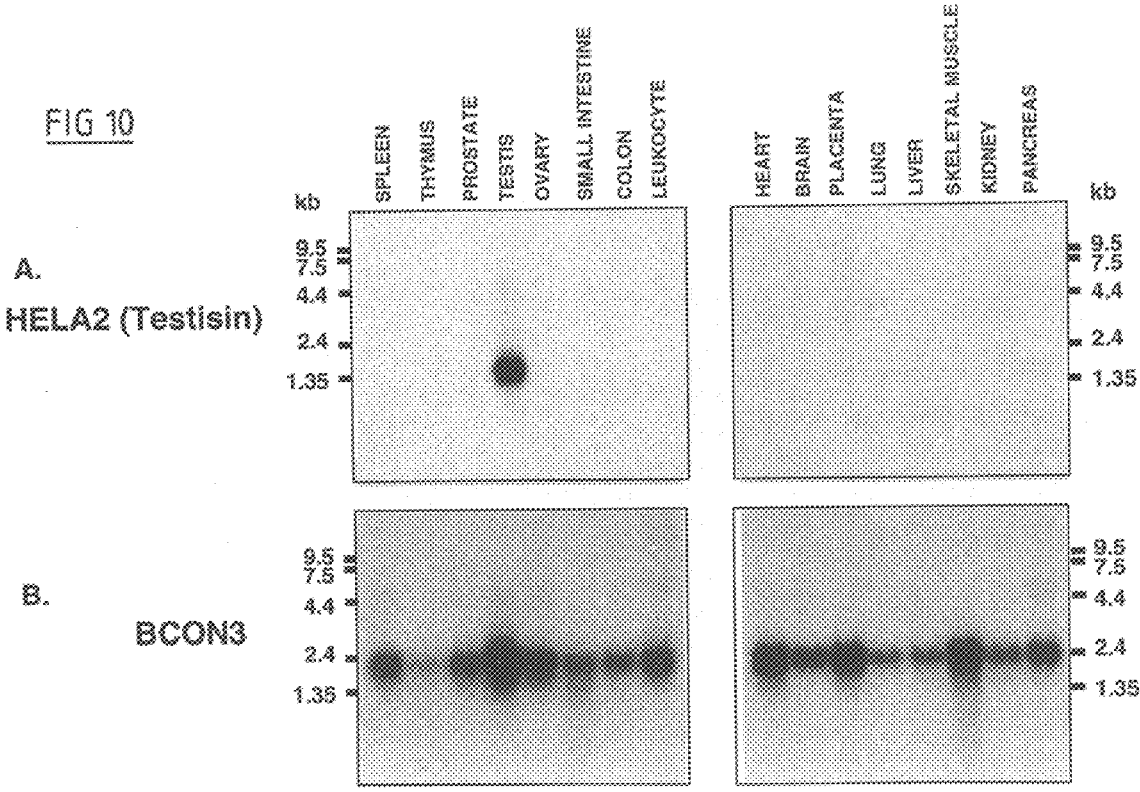
FIGS. 10A–10B is a photographic representation of a multiple normal tissue Northern blot (Clonetech) probed with: (A) HELA2 (testisin) specific probe and (B) BCON3 specific probe.

Northern blots displaying PolyA+ mRNA from 16 different normal tissues (Clontech) were hybridised at 65° C. in ExpressHyb solution using a 400 bp SacII/EcoRI 32P-labelled HELA2 probe for 3 h and then washed to a final stringency of 0.1×SSC0.1%SDS at 60° C. After a 5 h exposure, a strong band was observed only in the lane containing testis mRNA, demonstrating the specificity of HELA2 (testisin) expression for the testis (FIG. 10A). Prolonged exposure (4.5 days) of the blot revealed a very low level of HELA2 (testisin) mRNA expression in the prostate, lung and pancreas only. In contrast to HELA2, BCON3 is expressed in mRNA from most tissues present on the blot (FIG. 10B).

(C) HELA2 (Testisin) is Expressed in Sperm Cells, Demonstrating its Germ Cell Origin To determine whether HELA2 (testisin) expression is associated with germ cells of the testis, ejaculate specimens from normal fertile males were compared with those of post-vasectomy males by RT-PCR analysis using HELA2 (testisin) specific primers. Sperm is the primary product from the testis that is found in ejaculate; other components of the ejaculate are derived from the prostate.

First strand cDNA was reverse transcribed from total RNA which has been isolated from frozen or fresh ejaculate specimens. PCR was performed on the cDNA templates using the primers:

forward: 5' CTGACTTCCATGCCATCCTT 3' [SEQ ID NO:22] and reverse: 5' GCTCACGACTCCAATCTGAT 3' [SEQ ID NO:23].

Figure 11:
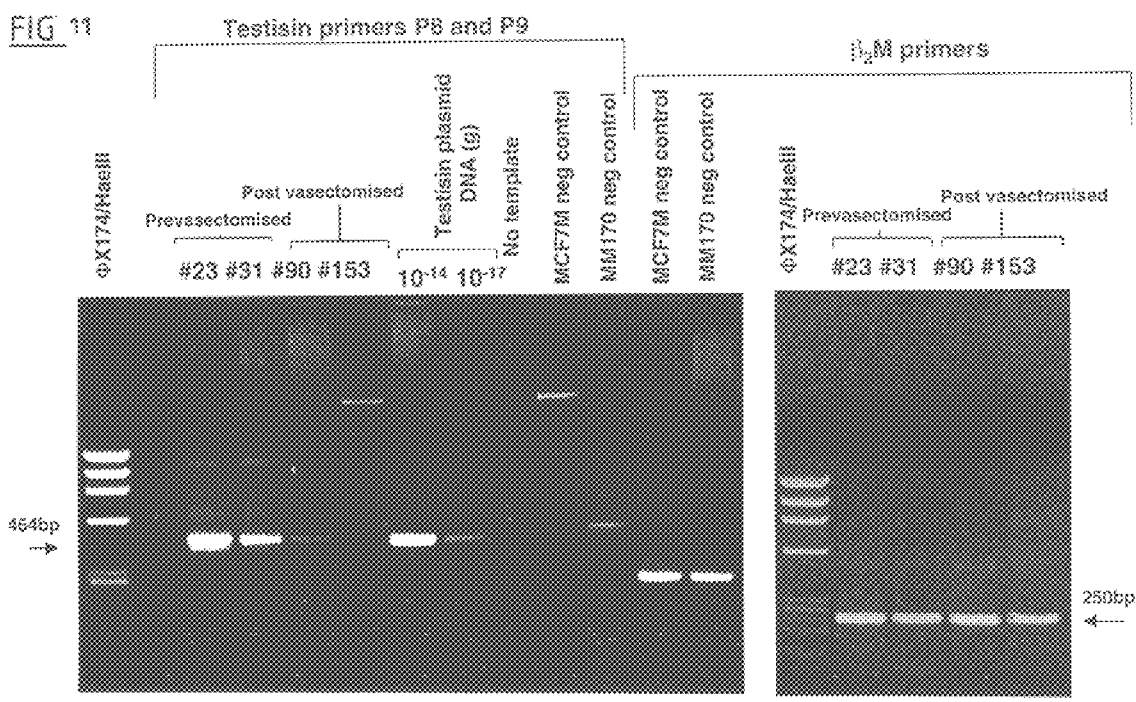
FIG. 11 is a photographic representation of agarose gel of PCR products generated by amplification of HELA2 (testisin) cDNA in prevasectomised and post-vasectomised ejaculate specimens. The HELA2 (testisin) PCR product is 464 bp and the β2-macroglobulin product is 250 bp.

As shown in FIG. 11, strong signals of the expected size of 464 bp were detected in ejaculate from normal males (Patients #23 and #31), while no HELA2 (testisin) was detected in Patient #153 (post-vasectomy). Patent #90 (post-vasectomy) showed a low level of amplification product which may reflect a small amount of residual sperm in the seminiferous tubules. PCR using primers specific for (2-macroglobulin was performed on the same samples as a control for the presence of approximately equal amounts of cDNA in each sample.

(D) HELA2 (Testisin) is Expressed in Immature Germ Cells of the Testis

Figure 12:
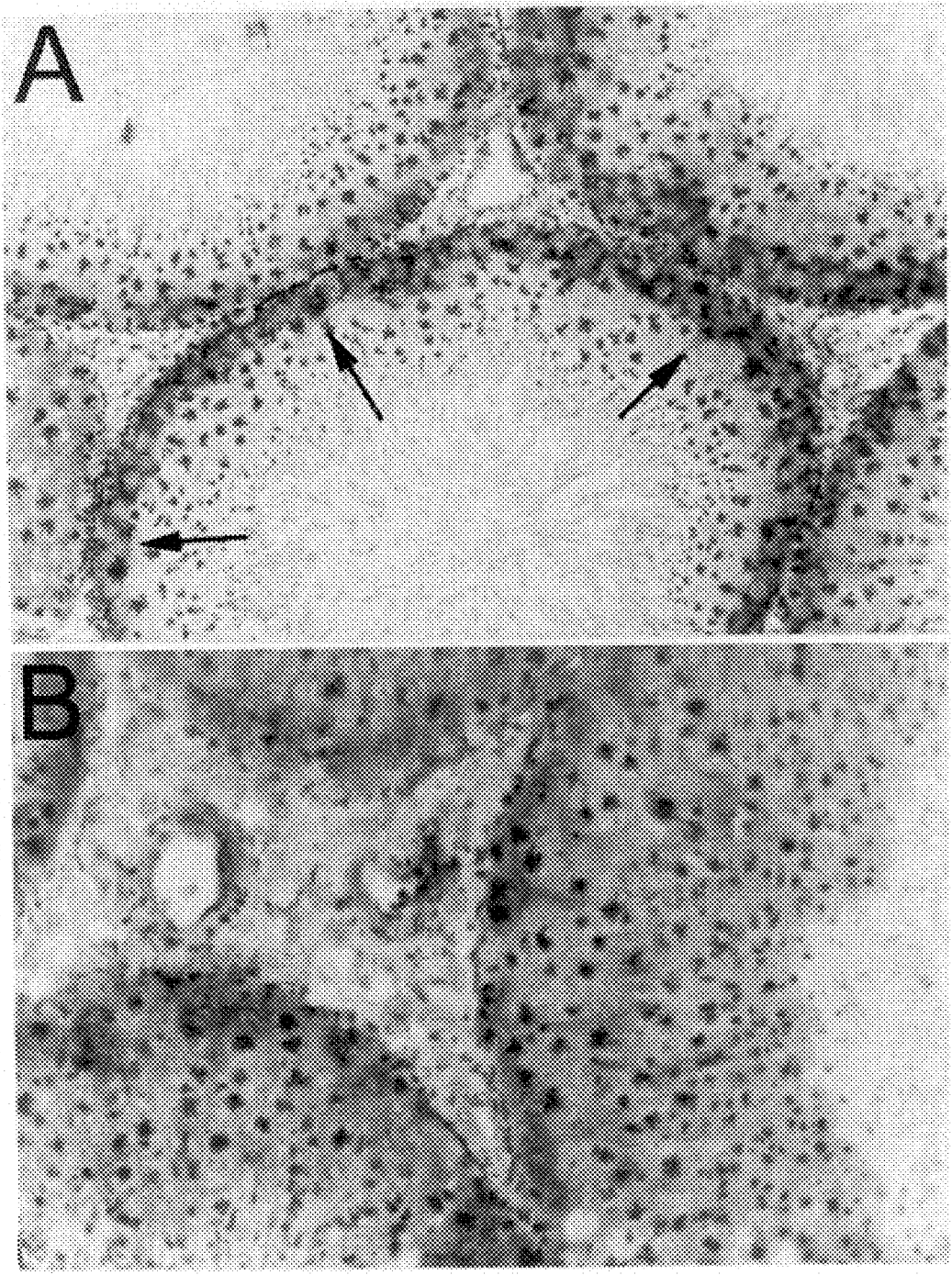
FIG. 12A–B are photographic representations of in situ hybridization of rat testis showing the localisation of HELA2 (testisin) mRNA to the germ cells of the testis.

In situ hybridization was performed on paraffin-embedded specimens of rat testis tissue using DIG-labelled HELA2 (testisin) RNA probes (T3 and T7 generated transcripts containing nucleotides 1–423 of HELA2 cDNA). The results using the antisense RNA probe showed strong positive staining near the basal lamina of the seminiferous tubules in the region associated with spermatocytes and spermatogonia (FIG. 12, see arrows). HELA2 (testisin) mRNA expression did not appear to be associated with Leydig cells and the pattern was not typical for Sertoli cell staining. The presence of HELA2 (testisin) mRNA in these cells indicates a role for HELA2 (testisin) in germ cell maturation and sperm development.

EXAMPLE 8

HELA2 (Testisin) Expression is Associated with Tumours in Non-Testis Cell-Types

The tissue and cell-type distribution of testisin mRNA transcripts in tumours were determined by Northern hybridization analyses of RNA extracted from in vitro cultured tumour cells lines derived from different cancerous tissues. HELA2 (testisin) was detected in the HeLa ovarian carcinoma the U937 lymphoma, and the melanoma cell line 253-3D. HELA2 (testisin) is also associated with cDNA libraries derived from tumours of the colon, pancreas, prostate and ovary (NCBI-EST Database). The presence of HELA2 (testisin) in tumours where it is not expressed normally indicates that it likely plays a role in tumourigenesis in several cell-types.

EXAMPLE 9

The HELA2 (Testisin) Gene is Located on Human Chromosome 16p13.3

Figure 13A:
FIGS. 13A–13B are representations showing: (A) spread of normal metaphase chromosomes showing bright dots where HELA2 (testisin) is expressed at 16p13.3; (B) Diagrammatic representation of chromosome 16p13.3 showing location of HELA (testisin) and relationship to other disease causing genes.
Figure 13:
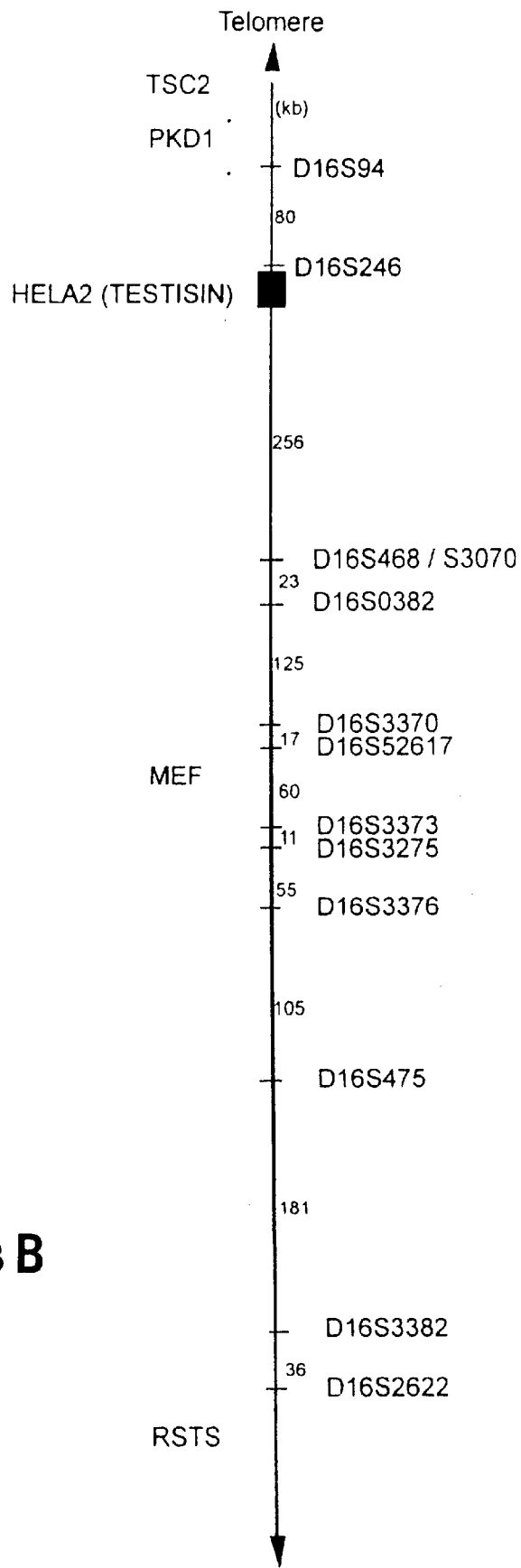

The genetic location of testisin was mapped to the short aim of chromosome 16 at 16p13.3 by fluorescence in-situ hybridization to normal metaphase chromosomes (FIG. 13A). Screening, of a chromosome 16 hybrid panel then sub-localised HELA2 (testisin) to the cosmid 406D6 which has been mapped to this region (Sood, R. et al (1997) Genomics 42: 83–95; Doggett, N. A. et al. (1995) Nature 377 (Suppl.):335–365. The cosmid lies between the markers D16S246 and D16S468 and the gene is located just centromeric to D16S246 (FIG. 13B). This region of the human genome is associated with high genetic instability and telomeric rearrangements underlie a variety of common human genetic disorders. Testisin is sandwiched between the human disease genes PKD1 (polycystic kidney disease) and tuberous sclerosis (TSC2) on the on side, and MEF (familial mediterranean fever) and Rubenstein-Taybi syndrome (RSTS) on the other side as diagrammed in FIG. 13B.

EXAMPLE 10

HELA2 (Testisin) mRNA and Protein Expression is Absent in Testicular Germ Cell Tumours To determine whether HELA2 (testisin) may play a role in testicular tumourigenesis, HELA2 (testisin) mRNA expression in normal testes and testicular tumour tissue obtained from 4 patients diagnosed with seminoma were compared by Northern blot analysis. HELA2 (testisin) mRNA was detected in normal testes from all four patients but was not detectable in the corresponding tumours (FIG. 14A). This data indicates a tumour suppressor role for HELA2 (testisin) in testicular germ cell tumours.

Expression of HELA2 (testisin) protein in testicular tissue was examined by immunohistochemistry. Paraffin-embedded tissue sections were fixed, treated, blocked, incubated with anti-peptide antibodies (1:10 dilution) and bound antibody detected with the Vectastain Universal Elite ABC kit (Vector Laboratories). Negative controls were performed in the absence of antibody. Strong staining of HELA2 (testisin) was detected in the germ cells of normal testis (N) but was absent in the adjacent tumour tissue (T) (for example, see FIG. 14B), providing further evidence of a tumour suppressor role for HELA2 (testisin) in testicular germ cell tumours.

EXAMPLE 11

Genomic Organisation of the HELA2 (Testisin) Gene

Figure 15:
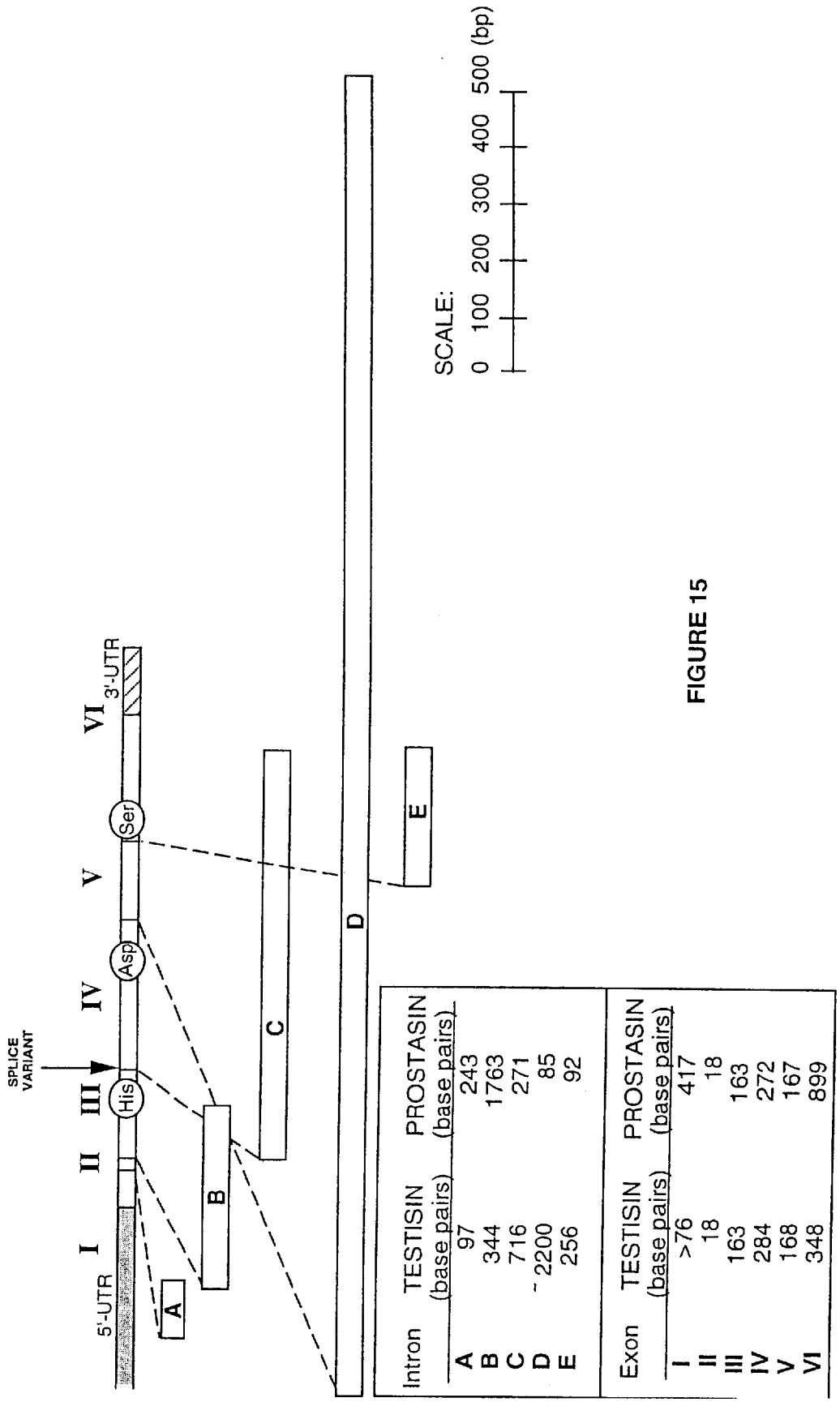
FIG. 15 is a diagrammatic representation of the genomic map of HELA2 (testisin) showing experimentally determined intron/exon boundaries and relative sizes of the introns (marked with a letter) and exons (marked with a roman numeral).
Figures 16, 16I, 16II, 16III, 16IV, 16V, 16VI:
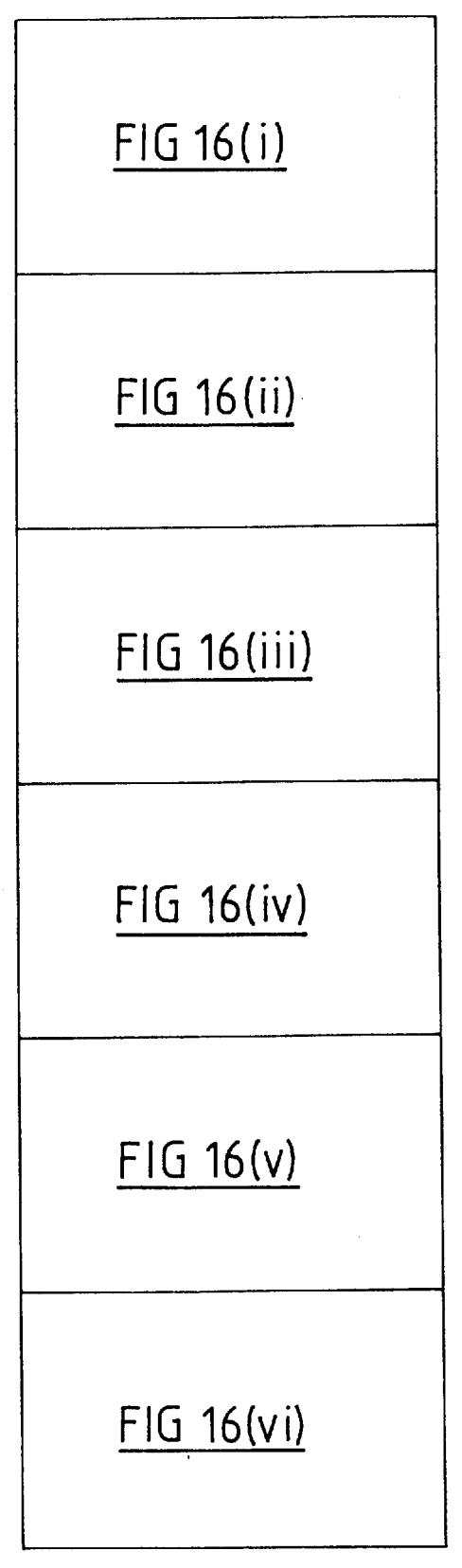

The HELA2 (testisin) gene is further characterised by determination of its genomic organisation. Intron-extron boundaries and most of the DNA sequence of the HELA2 (testisin) gene was determined from cosmid DNA by DNA sequencing. A genomic map of HELA2 (testisin) is given in FIG. 15. The intron/exon boundaries are highly conserved relative to prostasin, although the sizes of the introns show considerable variation. The genomic DNA sequence with introns in lower case and exons in upper case is shown in FIG. 16 and in SEQ ID NO 25. DNA sequence analysis is being performed on RNA from tumour tissues to ascertain the predicted function of HELA2 (testisin) as a tumour suppressor.

EXAMPLE 12

The HELA2 (Testisin) Short and Long Isoforms are Generated by Alternative mRNA Splicing Two isoforms of HELA2 (testisin) were identified which differ by an insertion of 2 amino acids (Tyr-Ser) between the catalytic His and Asp residues. These constitute the long (L) and short (S) isoforms. At the DNA level there is a corresponding insertion of 6 nucleotides which generates a Sfc1 restriction enzyme site. PCR amplification from single strand cDNA generated from HeLa cell total RNA followed by DNA sequence analysis of the amplified product demonstrated that the two isoforms are generated through the use of two alternative mRNA splice sites. The DNA sequence for the intron and the flanking exons are shown in FIG. 17. The resulting insertion of amino acids YS occurs 4 amino acids after the catalytic His residue of HELA2 (testisin). Preliminary molecular modelling shows the presence of this insertion is likely to alter the catalytic activity and/or specificity of HELA2 (testisin) for its substrates.

EXAMPLE 13

Mutation Analysis-HELA2 (Testisin) as a Tumour Suppressor

Intronic DNA sequence information generated above (see Example 11) is used to generate primers to amplify HELA2 (testisin) exons for SSCP analyses. Genomic DNA isolated from seminomas and corresponding normal testis as well as genomic DNA from wild-type and affected seminoma family members are analysed by SSCP for altered expression patterns indicative of genetic mutations. Evidence of genetic mutations are also being determined by DNA sequence analysis.

EXAMPLE 14

Homologues of Human HELA2 (Testisin) are Present in Other Species

Figures 18A, 18AI, 18AII:
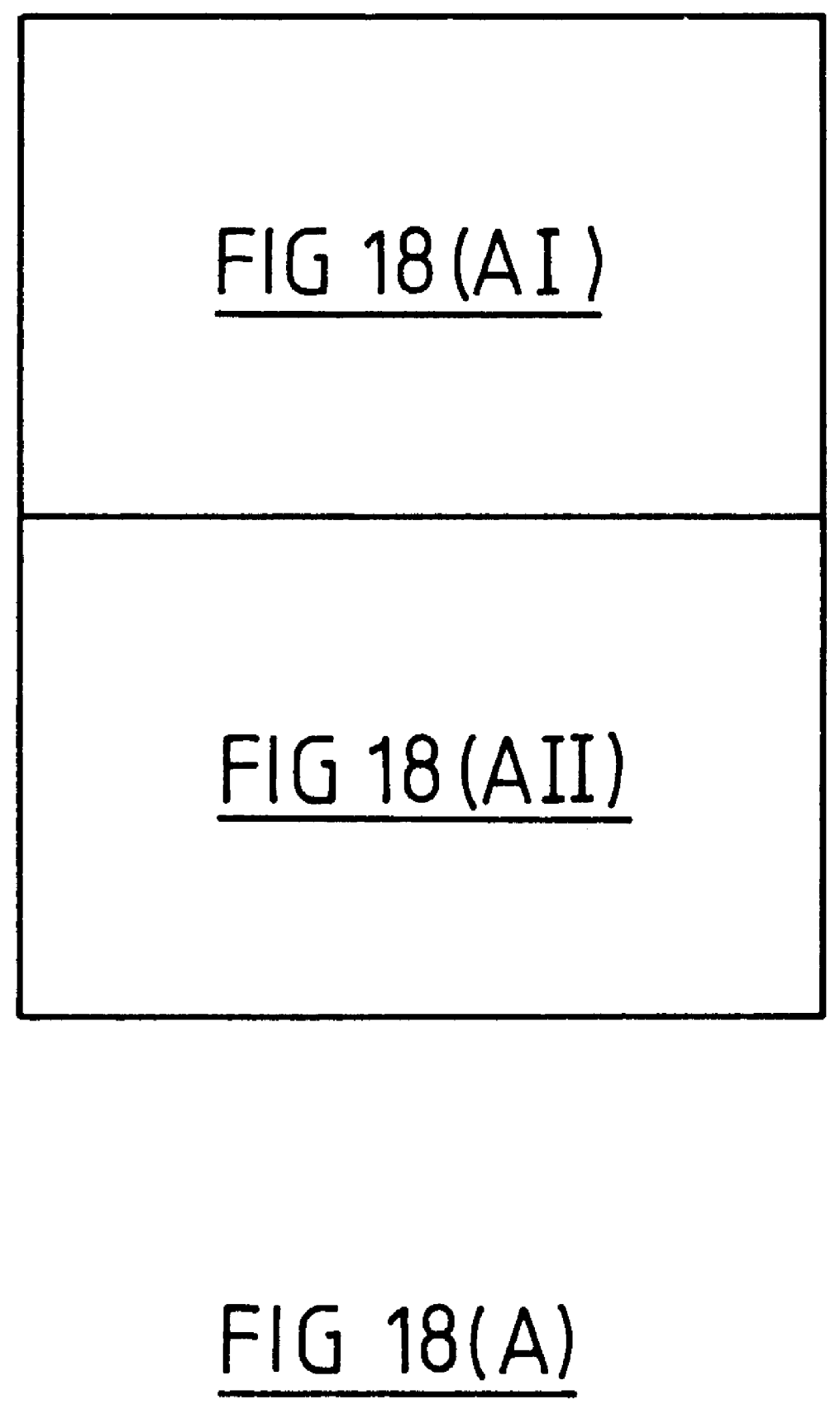
Figure 18B:
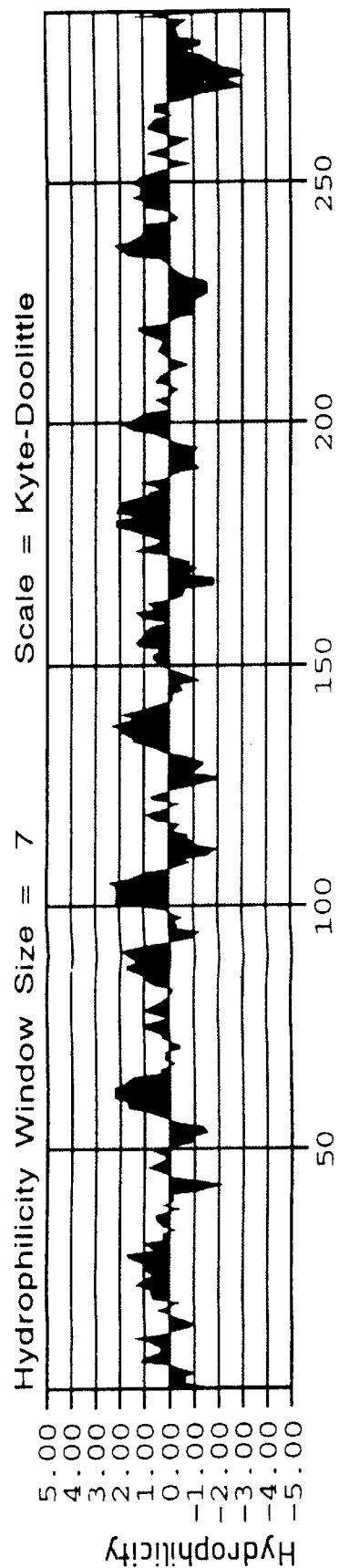

Southern blot analysis of genomic DNA isolated from a range of species using a HELA2 (testisin) cDNA probe shows that homologues of HELA2 (testisin) are present in hamster, mouse, marmoset and monkey. The mouse homologue of HELA2 (testisin) was identified and obtained as an EST clone. The cDNA sequence and corresponding amino acid sequence of mouse HELA2 (testisin) was determined (FIG. 18) and is given in SEQ ID NO 27. The mouse cDNA encodes a protein which contains the catalytic triad of His, Asp and Ser (circles) and 10 cysteine residues (small boxes), and an activation site (triangle) as found in HELA2 (testisin). The hydrophilicity plot shows the presence of a hydrophobic sequence at the carboxy terminus suggesting the presence of a putative membrane anchor. Comparison of the mouse and human sequences show 68.1% homology at the cDNA level and 69.1% homology at the amino acid level.

EXAMPLE 15

HELA2 (Testisin) is Part of a Cluster of Homologous Genes on Chromosome 16p13.3

Figure 19:
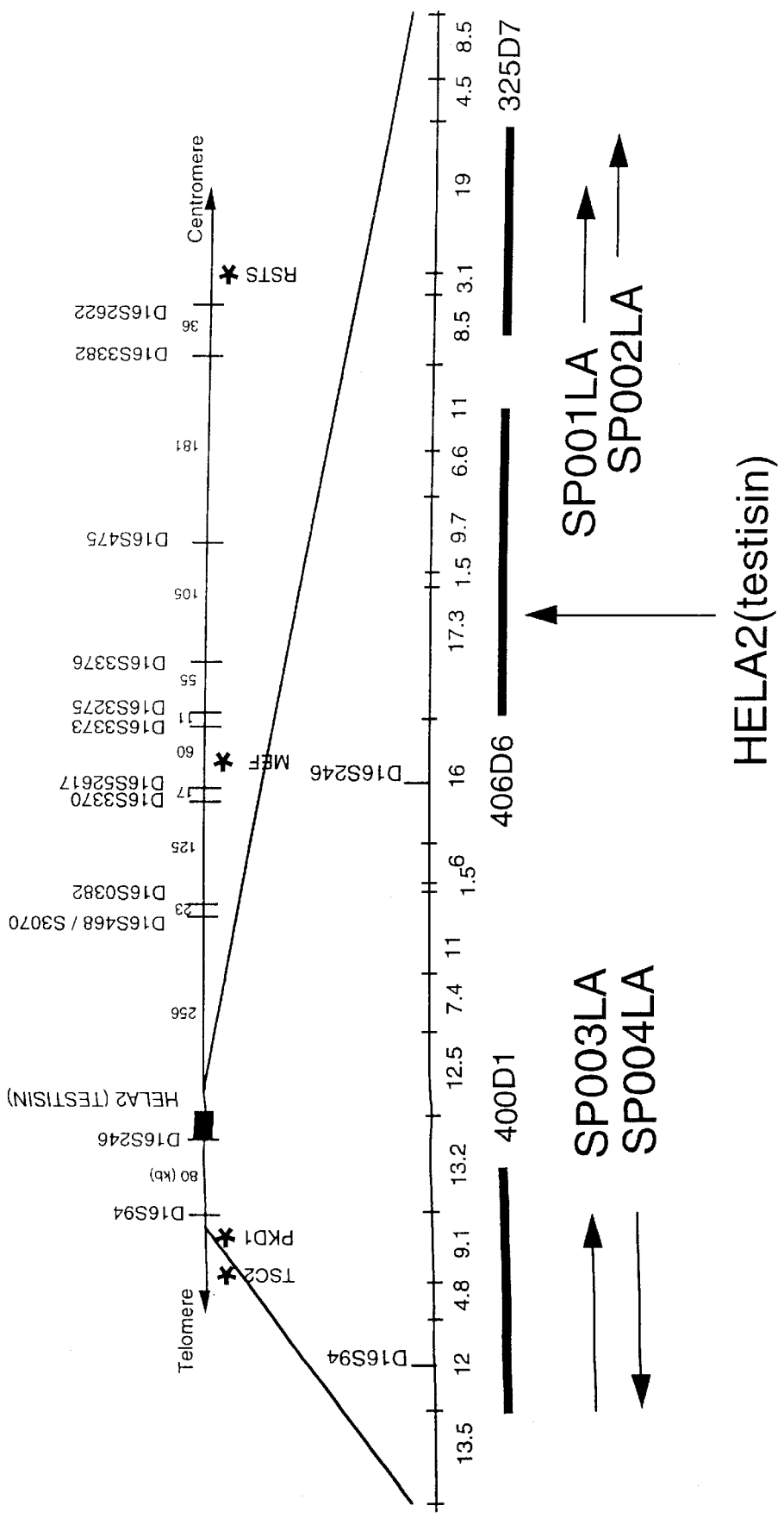
FIG. 19 is a diagrammatic representation of chromosome 16p13.3 showing the serine proteinase gene cluster which includes HELA2 (testisin). Lines represent cosmids containing the respective serine proteinase genes.
Figure 20A:
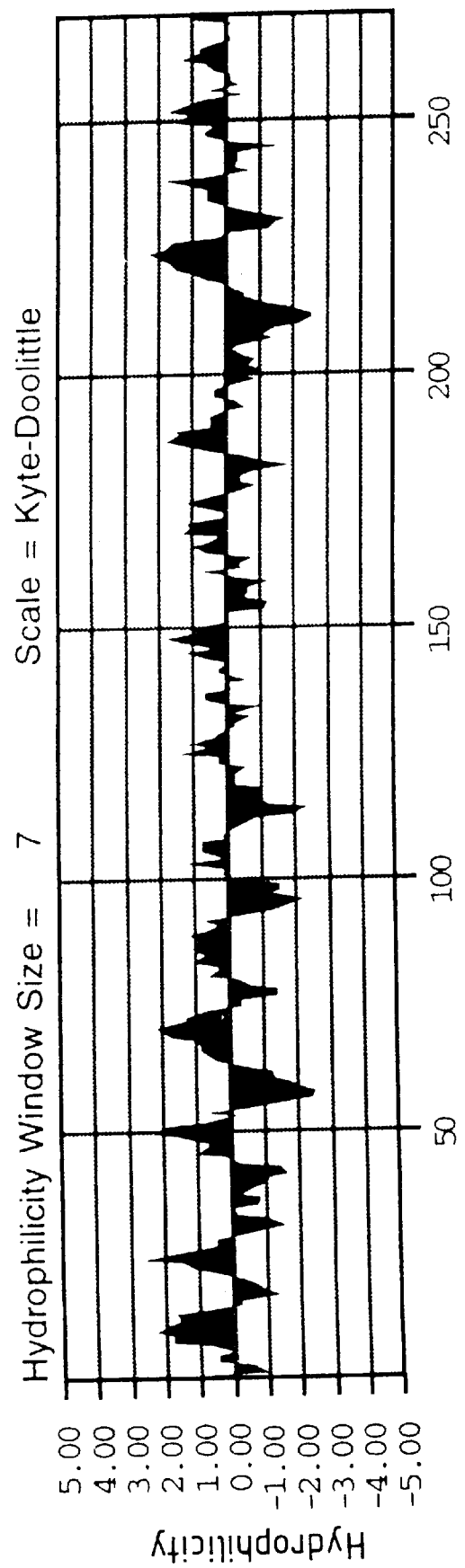
FIGS. 20A(A)–20A(B) are representations of: (AI–III) the cDNA sequence of SP001LA (SEQ ID NO:28). Catalytic residues are indicated by circles and cysteins likely involved in disulfide bonding are indicated by squares; (B) hydrophobicity plots of SP001LA amino acid sequence.
Figure 20B:
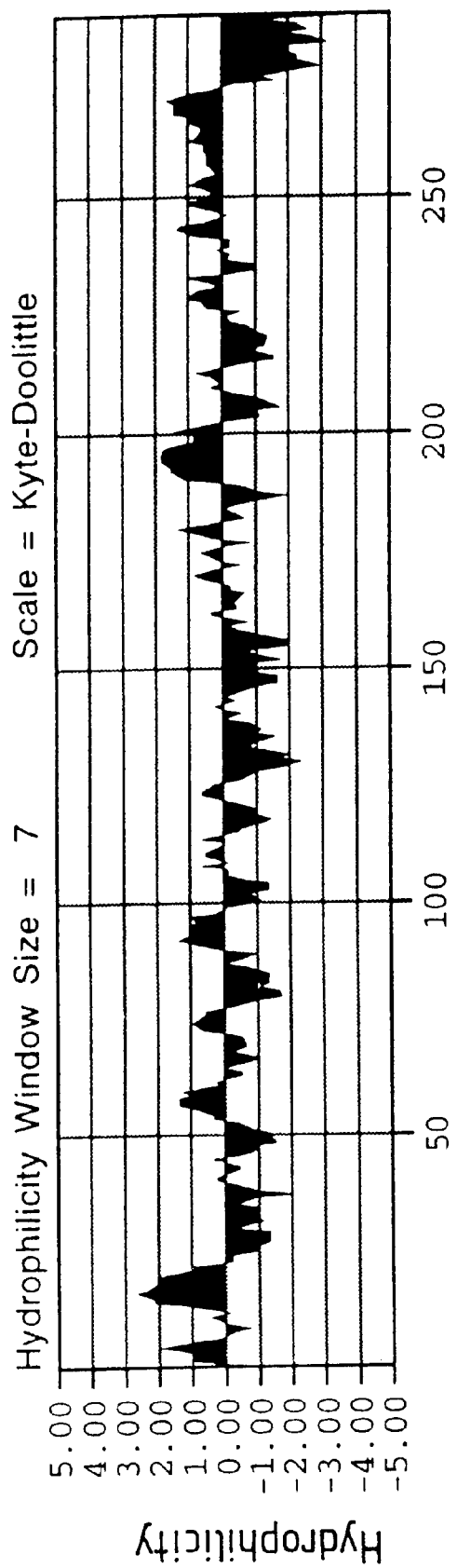
FIGS. 20B(A)–20B(B) are representations of: (AI–II) the cDNA sequence of SP002LA (SEQ ID NO:29). Catalytic residues are indicated by circles and cysteines likely involved in disulfide bonding are indicated by squares. (B) Hydrophobicity plot of SP002LA amino acid sequence.
Figure 20C:
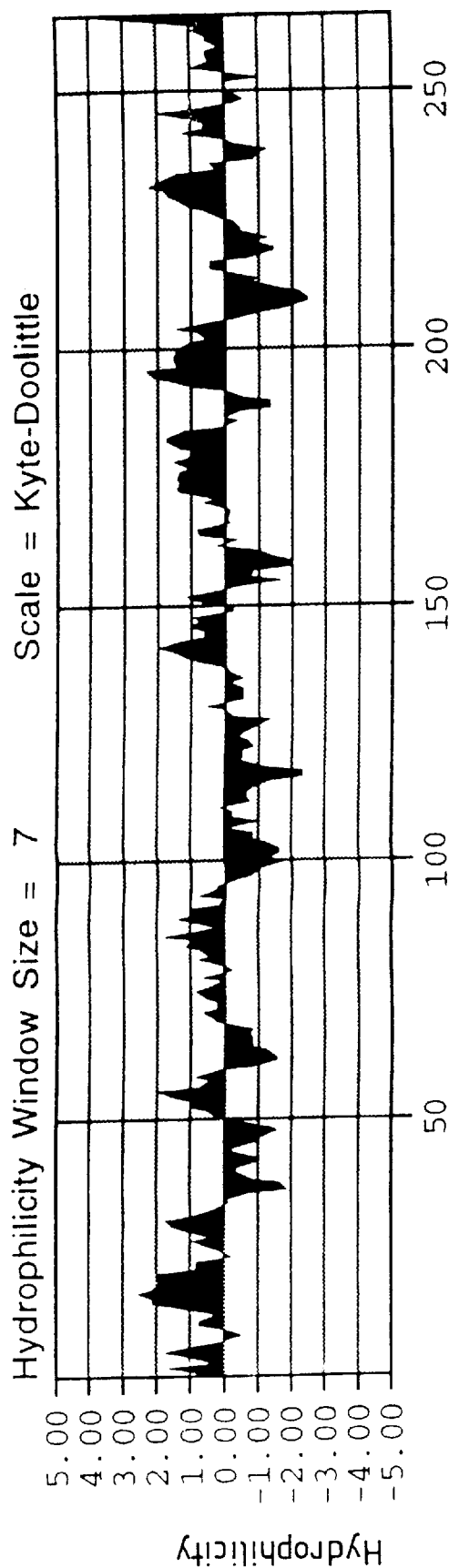
FIGS. 20C(A)–20C(B) representation of: (AI–II) the cDNA sequence of SP003LA (SEQ ID NO:30). Catalytic residues are indicated by circles and cysteines likely involved in disulfide bonding are indicated by squares. (B) Hydrophobicity plot of SP003LA amino acid sequence.

Analysis of DNA sequences released to NCBI databases reveals the presence of homologues of HELA2 (testisin) in a cluster on Chromosome 16p13.3. FIG. 19 shows the positions of these genes, designated SP001LA, SP002LA, SP003LA, and SP004LA, relative to HELA2 (testisin) and the respective cosmids (Sood, R. et al (1997) Genomics 42: 83–95) in which they are located. FIGS. 20A, 20B and 20C show the partial cDNA and deduced amino acid sequences of SP001LA, SP002LA, and SP003LA respectively. Each cDNA encodes a protein which contains the catalytic triad of His, Asp and Ser (circles) and 10 cysteine residues (small boxes), and an activation site (triangle) as found in HELA2 (testisin). Comparisons of the cDNA and amino acid sequences from the heavy chain region through to the poly A tail gives the % identity with HELA2 (testisin) as follows:

|  | cDNA | Protein |
|---|---|---|
| SP001LA | 34.8% | 47.3% |
| SP002LA | 41.0% | 47.1% |
| SP003LA | 40.3% | 51.3% |

Each of the serine proteinases encoded by these genes show that they have carboxy terminal extensions, and SP002LA is the only one with a hydrophobic carboxy terminal tail indicative of a membrane anchored protein. Identification of an expressed sequence tag (EST) from a human testis cDNA library demonstrates that this gene is expressed in the testis, like HELA2 (testisin). The location of this serine proteinase cluster on chromosome 16p13.3 flanking HELA2 (testisin) suggests that these serine proteinases are also involved, like HELA2 (testisin), in sperm maturation and development. Thus they may constitute a proteolytic cascade which is essential for these processes. Loss or mutation of these genes may lead to testicular germ cell tumours and to other testicular abnormalities, such as infertility.

EXAMPLE 16

ATC2 Serine Proteinase

ATC2 was isolated from the cDNA of PAI-2 expressing HeLa cells following treatment with TNF and cycloheximide. A partial DNA sequence for ATC2 cDNA has been obtained which encompasses the sequence encoding the serine proteinase catalytic region. Additional clones extending to both 5' and 3' directions have been obtained. The available nucleic acid sequence of ATC2 cDNA and its deduced amino acid sequence shows that it is a member of the serine proteinase family with homology to hepsin, prostasin, and acrosin. It thus belongs to the same family as HELA2. The catalytic region includes the His, Asp and Ser conserved motifs. Preliminary Northern blot experiments have failed to detect ATC2 mRNA in total RNA isolated from resting HeLa cells, indicating it is not expressed in abundance in these cells, which may therefore be tightly regulated. As ATC2 was isolated from cells following treatment with TNF and cycloheximide, its expression may be induced by these agents in HeLa cells. These data have potential significance for a role for ATC2 in apoptosis and cell death. ATC2 may be intracellular, extracellular or found on the cell surface and is likely to be involved in regulating cell functions. Thus ATC2 may have potential significance in the treatment of cancer and diseases involving dysregulation of cell growth and survival. The nucleotide and corresponding amino acid sequence of ATC2 is shown in SEQ ID NOs: 7 and 8, respectively.

EXAMPLE 17

BCON3

Figure 21:
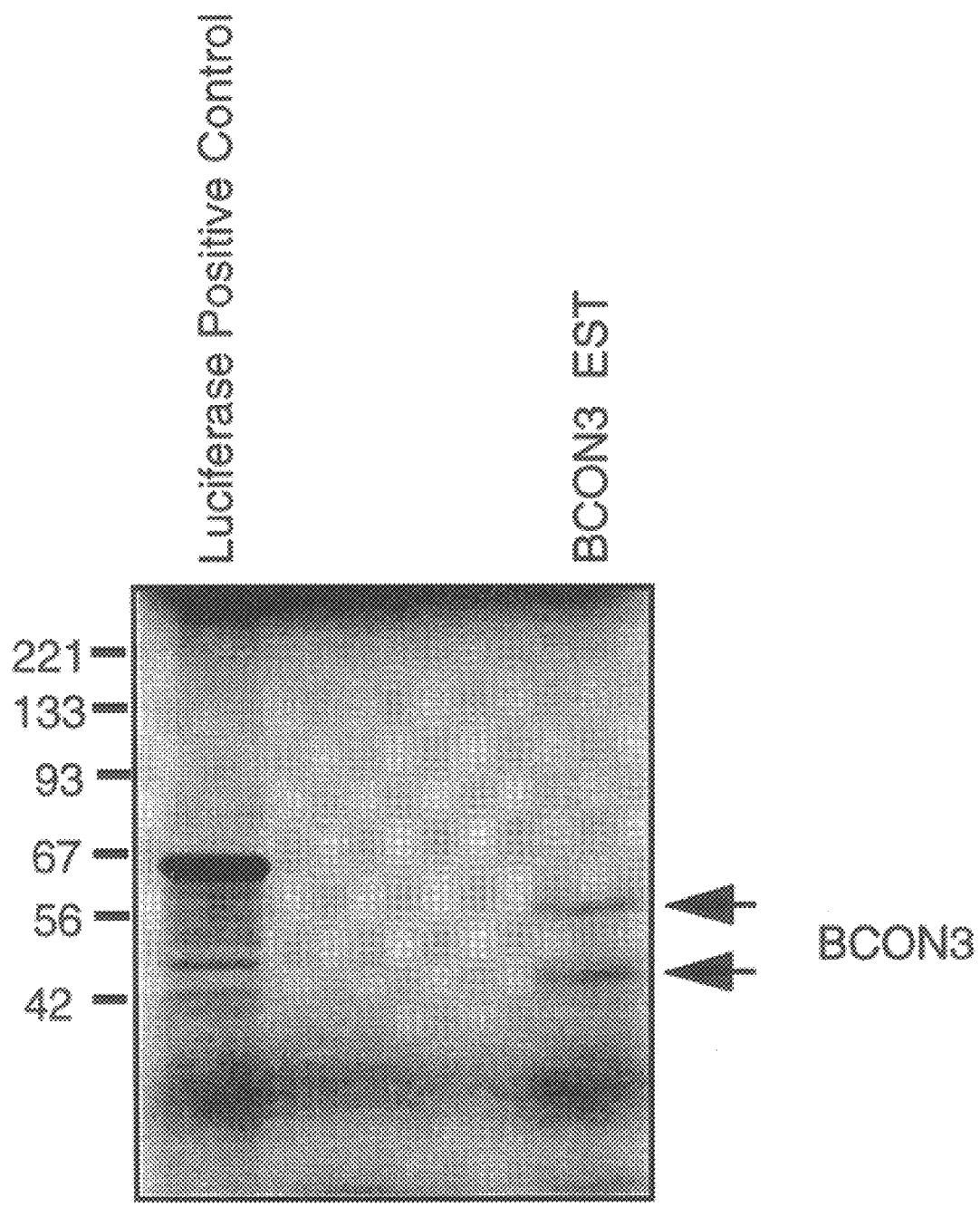
FIG. 21 is a photographic representation of in vitro transcription/translation of BCON3 showing the protein products.

The deduced amino acid sequence of BCON3 (SEQ ID NO:10) reveals that it is novel. At both the DNA and protein level, BCON3 shows homology to members of the kinase family of proteins. Although it cannot be classified as a member of any particular sub-family of kinases, alignments of the BCON3 protein with the conserved domains of thymidine kinases and tyrosine and serine/threonine protein kinases indicates possible ATP/GTP binding and phosphate transfer regions. Thus, it may be the first member of a new family of kinases. Analysis of the translation product using hydrophobicity plots and the Prosite protein analysis algorithms indicates BCON3 may lack an N-terminal signal sequence (that is, it is likely to encode an intracellular protein) and it possesses a nuclear localization signal. BCON3 mRNA is approximately 2300 nucleotides in lengths cDNA sequence (SEQ ID NO:9) has been obtained covering about 95% of the transcript and including the 3' poly A tail. BCON3 mRNA is expressed in most normal tissues as demonstrated by dot blot analysis of 50 normal tissue specimens (standardised to 8 different housekeeping genes) (Clontech). (FIG. 9). Analysis of BCON3 mRNA expression using a multiple tissue Northern blot displaying PolyA+mRNA from 16 different normal tissues (Clontech) shows that BCON3 is expressed in most tissues (FIG. 10B). Expression by in vitro transcription/translation expression using a partial BCON3 cDNA fragment shows BCON3 encodes a protein. Two major transcription/translation products are detected, one of 51 kDa, the size predicted from the open reading frame, and a second product of about 43 kDa, which may represent a partial translation product (FIG. 21).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. An isolated nucleic acid molecule encoding a serine proteinase comprising an amino acid sequence as set forth in SEQ ID NO:4 wherein at least a portion of said nucleic acid molecule is capable of being amplified by polymerase chain reaction (PCR) using the following primers:

5' ACAGAATTCTGCGTIGTIACIGCIGCICAYTG 3' [SEQ ID NO:1]; and

5' ACAGAATTCAXIGGICCICCIC/GT/AXTCICC 3' [SEQ ID NO:2];

or a complementary form of said primers.

2. An isolated nucleic acid molecule encoding a serine proteinase comprising an amino acid sequence as set forth in SEQ ID NO:6 wherein at least a portion of said nucleic acid molecule is capable of being amplified by polymerase chain reaction (PCR) using the following primers:

5' ACAGAATTCTGCGTIGTIACIGCIGCICAYTG 3' [SEQ ID NO:1]; and

5' ACAGAATTCAXIGGICCICCIC/GT/AXTCICC 3' [SEQ ID NO:2];

or a complementary form of said primers.

3. An isolated nucleic acid molecule comprising a sequence of nucleotides as set forth in SEQ ID NO:3 or a nucleotide sequence capable of hybridizing to the sequence set forth in SEQ ID NO:3 under medium stringency conditions at 42° C., wherein said sequence encodes a serine proteinase.

4. An isolated nucleic acid molecule comprising a sequence of nucleotides as set forth in SEQ ID NO:5 or a nucleotide sequence capable of hybridizing to the sequence set forth in SEQ ID NO:5 under medium stringency conditions at 42° C., wherein said sequence encodes a serine proteinase.

5. An isolated nucleic acid molecule comprising at least two genes each of said two genes has a nucleotide sequence selected from the group consisting of SEQ ID NO: 3, 5, 28, 29, or 30 or a nucleotide sequence capable of hybridizing to any one of the sequences under medium stringency conditions at 42° C., wherein said sequence encodes a serine proteinase.

6. An isolated nucleic acid molecule comprising a nucleotide selected from the group consisting of SEQ ID NO: 3 or 5, or nucleotide sequence capable of hybridizing to SEQ ID NO: 3 or SEQ ID NO: 5 under medium stringency conditions at 42° C., wherein said sequence encodes a shrine proteinase.

7. A vector comprising a nucleic acid molecule according to any one of claims 1, 2, 3, 4, 5 or 6.

8. An expression vector comprising a nucleic acid molecule according to any one of claims of 1, 2, 3, 4, 5, or 6.

9. A cell containing a vector comprising a nucleic acid molecule according to any one of claims 1, 2, 3, 4, 5 or 6.

10. A cell containing an expression vector comprising a nucleic acid molecule according to any one of claims 1, 2, 3, 4, 5 or 6.

* * * * *

SEQUENCE LISTING (1) GENERAL INFORMATION:

(iii) NUMBER OF SEQUENCES: 30

(2) INFORMATION FOR SEQ ID NO:1:

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified base
        (B) LOCATION: 15
        (D) OTHER INFORMATION: N equals Inosine (ix) FEATURE:
        (A) NAME/KEY: modified base
        (B) LOCATION: 18
        (D) OTHER INFORMATION: N equals Inosine (ix) FEATURE:
        (A) NAME/KEY: modified base
        (B) LOCATION: 21
        (D) OTHER INFORMATION: N equals Inosine (ix) FEATURE:
        (A) NAME/KEY: modified base
        (B) LOCATION: 24
        (D) OTHER INFORMATION: N equals Inosine (ix) FEATURE:
        (A) NAME/KEY: modified base
        (B) LOCATION: 27
        (D) OTHER INFORMATION: N equals Inosine (xi) SEQUENCE DESCRIPTION: SEQ ID NO:1:

ACAGAATTCT GGGTNGTNAC NGCNGCNCAY TG                                32

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified base
        (B) LOCATION: 12
        (D) OTHER INFORMATION: N equals Inosine (ix) FEATURE:
        (A) NAME/KEY: modified base
        (B) LOCATION: 15
        (D) OTHER INFORMATION: N equals Inosine (ix) FEATURE:
        (A) NAME/KEY: modified base
        (B) LOCATION: 18
        (D) OTHER INFORMATION: N equals Inosine (ix) FEATURE:
        (A) NAME/KEY: modified base
        (B) LOCATION: 21
        (D) OTHER INFORMATION: N equals Inosine (ix) FEATURE:
        (A) NAME/KEY: modified base
        (B) LOCATION: 27
        (D) OTHER INFORMATION: N equals Inosine (xi) SEQUENCE DESCRIPTION: SEQ ID NO:2:

ACAGAATTCA RNGGNCCNCC NSWRTCNCC                                    29

(2) INFORMATION FOR SEQ ID NO:3:
```

(i) SEQUENCE CHARACTERISTICS:
    (A) LENGTH: 1094 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: CDS
    (B) LOCATION: 17..955

(xi) SEQUENCE DESCRIPTION: SEQ ID NO:3:

```
CGCGGGAGAG GAGGCC ATG GGC GCG CGC GGG GCG CTG CTG CTG GCG CTG            49
               Met Gly Ala Arg Gly Ala Leu Leu Leu Ala Leu
                 1               5                  10

CTG CTG GCT CGG GCT GGA CTC AGG AAG CCG GAG TCG CAG GAG GCG GCG           97
Leu Leu Ala Arg Ala Gly Leu Arg Lys Pro Glu Ser Gln Glu Ala Ala
            15                  20                  25

CCG TTA TCA GGA CCA TGC GGC CGA CGG GTC ATC ACG TCG CGC ATC GTG          145
Pro Leu Ser Gly Pro Cys Gly Arg Arg Val Ile Thr Ser Arg Ile Val
        30                  35                  40

GGT GGA GAG GAC GCC GAA CTC GGG CGT TGG CCG TGG CAG GGG AGC CTG          193
Gly Gly Glu Asp Ala Glu Leu Gly Arg Trp Pro Trp Gln Gly Ser Leu
    45                  50                  55

CGC CTG TGG GAT TCC CAC GTA TGC GGA GTG AGC CTG CTC AGC CAC CGC          241
Arg Leu Trp Asp Ser His Val Cys Gly Val Ser Leu Leu Ser His Arg
 60                  65                  70                  75

TGG GCA CTC ACG GCG GCG CAC TGC TTT GAA ACT GAC CTT AGT GAT CCC          289
Trp Ala Leu Thr Ala Ala His Cys Phe Glu Thr Asp Leu Ser Asp Pro
                 80                  85                  90

TCC GGG TGG ATG GTC CAG TTT GGC CAG CTG ACT TCC ATG CCA TCC TTC          337
Ser Gly Trp Met Val Gln Phe Gly Gln Leu Thr Ser Met Pro Ser Phe
             95                 100                 105

TGG AGC CTG CAG GCC TAC TAC ACC CGT TAC TTC GTA TCG AAT ATC TAT          385
Trp Ser Leu Gln Ala Tyr Tyr Thr Arg Tyr Phe Val Ser Asn Ile Tyr
         110                 115                 120

CTG AGC CCT CGC TAC CTG GGG AAT TCA CCC TAT GAC ATT GCC TTG GTG          433
Leu Ser Pro Arg Tyr Leu Gly Asn Ser Pro Tyr Asp Ile Ala Leu Val
     125                 130                 135

AAG CTG TCT GCA CCT GTC ACC TAC ACT AAA CAC ATC CAG CCC ATC TGT          481
Lys Leu Ser Ala Pro Val Thr Tyr Thr Lys His Ile Gln Pro Ile Cys
140                 145                 150                 155

CTC CAG GCC TCC ACA TTT GAG TTT GAG AAC CGG ACA GAC TGC TGG GTG          529
Leu Gln Ala Ser Thr Phe Glu Phe Glu Asn Arg Thr Asp Cys Trp Val
                160                 165                 170

ACT GGC TGG GGG TAC ATC AAA GAG GAT GAG GCA CTG CCA TCT CCC CAC          577
Thr Gly Trp Gly Tyr Ile Lys Glu Asp Glu Ala Leu Pro Ser Pro His
            175                 180                 185

ACC CTC CAG GAA GTT CAG GTC GCC ATC ATA AAC AAC TCT ATG TGC AAC          625
Thr Leu Gln Glu Val Gln Val Ala Ile Ile Asn Asn Ser Met Cys Asn
        190                 195                 200

CAC CTC TTC CTC AAG TAC AGT TTC CGC AAG GAC ATC TTT GGA GAC ATG          673
His Leu Phe Leu Lys Tyr Ser Phe Arg Lys Asp Ile Phe Gly Asp Met
    205                 210                 215

GTT TGT GCT GGC AAT GCC CAA GGC GGG AAG GAT GCC TGC TTC GGT GAC          721
Val Cys Ala Gly Asn Ala Gln Gly Gly Lys Asp Ala Cys Phe Gly Asp
220                 225                 230                 235

TCA GGT GGA CCC TTG GCC TGT AAC AAG GAT GGA CTG TGG TAT CAG ATT          769
Ser Gly Gly Pro Leu Ala Cys Asn Lys Asp Gly Leu Trp Tyr Gln Ile
                240                 245                 250
```

```
GGA GTC GTG AGC TGG GGA GTG GGC TGT GGT CGG CCC AAT CGG CCC GGT      817
Gly Val Val Ser Trp Gly Val Gly Cys Gly Arg Pro Asn Arg Pro Gly
            255                 260                 265

GTC TAC ACC AAT ATC AGC CAC CAC TTT GAG TGG ATC CAG AAG CTG ATG      865
Val Tyr Thr Asn Ile Ser His His Phe Glu Trp Ile Gln Lys Leu Met
        270                 275                 280

GCC CAG AGT GGC ATG TCC CAG CCA GAC CCC TCC TGG CCG CTA CTC TTT      913
Ala Gln Ser Gly Met Ser Gln Pro Asp Pro Ser Trp Pro Leu Leu Phe
285                 290                 295

TTC CCT CTT CTC TGG GCT CTC CCA CTC CTG GGG CCG GTC TGA              955
Phe Pro Leu Leu Trp Ala Leu Pro Leu Leu Gly Pro Val  *
300                 305                 310

GCCTACCTGA GCCCATGCAG CCTGGGGCCA CTGCCAAGTC AGGCCCTGGT TCTCTTCTGT   1015

CTTGTTTGGT AATAAACACA TTCCAGTTGA TGCCTTGCAG GGCATTTTTC AAAAAAAAAA   1075

AAAAAAAAAA AAAAAAAAA                                                1094

(2) INFORMATION FOR SEQ ID NO:4:

(i) SEQUENCE CHARACTERISTICS:
        (A) LENGTH: 312 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Ala Arg Gly Ala Leu Leu Leu Ala Leu Leu Leu Ala Arg Ala
 1               5                  10                  15

Gly Leu Arg Lys Pro Glu Ser Gln Glu Ala Ala Pro Leu Ser Gly Pro
                20                  25                  30

Cys Gly Arg Arg Val Ile Thr Ser Arg Ile Val Gly Gly Glu Asp Ala
            35                  40                  45

Glu Leu Gly Arg Trp Pro Trp Gln Gly Ser Leu Arg Leu Trp Asp Ser
        50                  55                  60

His Val Cys Gly Val Ser Leu Leu Ser His Arg Trp Ala Leu Thr Ala
 65                 70                  75                  80

Ala His Cys Phe Glu Thr Asp Leu Ser Asp Pro Ser Gly Trp Met Val
                85                  90                  95

Gln Phe Gly Gln Leu Thr Ser Met Pro Ser Phe Trp Ser Leu Gln Ala
               100                 105                 110

Tyr Tyr Thr Arg Tyr Phe Val Ser Asn Ile Tyr Leu Ser Pro Arg Tyr
           115                 120                 125

Leu Gly Asn Ser Pro Tyr Asp Ile Ala Leu Val Lys Leu Ser Ala Pro
130                 135                 140

Val Thr Tyr Thr Lys His Ile Gln Pro Ile Cys Leu Gln Ala Ser Thr
145                 150                 155                 160

Phe Glu Phe Glu Asn Arg Thr Asp Cys Trp Val Thr Gly Trp Gly Tyr
                165                 170                 175

Ile Lys Glu Asp Glu Ala Leu Pro Ser Pro His Thr Leu Gln Glu Val
            180                 185                 190

Gln Val Ala Ile Ile Asn Asn Ser Met Cys Asn His Leu Phe Leu Lys
        195                 200                 205

Tyr Ser Phe Arg Lys Asp Ile Phe Gly Asp Met Val Cys Ala Gly Asn
    210                 215                 220

Ala Gln Gly Gly Lys Asp Ala Cys Phe Gly Asp Ser Gly Gly Pro Leu
225                 230                 235                 240
```

```
Ala Cys Asn Lys Asp Gly Leu Trp Tyr Gln Ile Gly Val Val Ser Trp
            245                 250                 255

Gly Val Gly Cys Gly Arg Pro Asn Arg Pro Gly Val Tyr Thr Asn Ile
            260                 265                 270

Ser His His Phe Glu Trp Ile Gln Lys Leu Met Ala Gln Ser Gly Met
            275                 280                 285

Ser Gln Pro Asp Pro Ser Trp Pro Leu Leu Phe Phe Pro Leu Leu Trp
    290                 295                 300

Ala Leu Pro Leu Leu Gly Pro Val
305                 310

(2) INFORMATION FOR SEQ ID NO:5:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 17..961

(xi) SEQUENCE DESCRIPTION: SEQ ID NO:5:
```

| | | |
|---|---|---|
| CGCGGGAGAG GAGGCC ATG GGC GCG CGC GGG GCG CTG CTG CTG GCG CTG | | 49 |
| Met Gly Ala Arg Gly Ala Leu Leu Leu Ala Leu | | |
| 1 5 10 | | |
| CTG CTG GCT CGG GCT GGA CTC AGG AAG CCG GAG TCG CAG GAG GCG GCG | | 97 |
| Leu Leu Ala Arg Ala Gly Leu Arg Lys Pro Glu Ser Gln Glu Ala Ala | | |
| 15 20 25 | | |
| CCG TTA TCA GGA CCA TGC GGC CGA CGG GTC ATC ACG TCG CGC ATC GTG | | 145 |
| Pro Leu Ser Gly Pro Cys Gly Arg Arg Val Ile Thr Ser Arg Ile Val | | |
| 30 35 40 | | |
| GGT GGA GAG GAC GCC GAA CTC GGG CGT TGG CCG TGG CAG GGG AGC CTG | | 193 |
| Gly Gly Glu Asp Ala Glu Leu Gly Arg Trp Pro Trp Gln Gly Ser Leu | | |
| 45 50 55 | | |
| CGC CTG TGG GAT TCC CAC GTA TGC GGA GTG AGC CTG CTC AGC CAC CGC | | 241 |
| Arg Leu Trp Asp Ser His Val Cys Gly Val Ser Leu Leu Ser His Arg | | |
| 60 65 70 75 | | |
| TGG GCA CTC ACG GCG GCG CAC TGC TTT GAA ACC TAT AGT GAC CTT AGT | | 289 |
| Trp Ala Leu Thr Ala Ala His Cys Phe Glu Thr Tyr Ser Asp Leu Ser | | |
| 80 85 90 | | |
| GAT CCC TCC GGG TGG ATG GTC CAG TTT GGC CAG CTG ACT TCC ATG CCA | | 337 |
| Asp Pro Ser Gly Trp Met Val Gln Phe Gly Gln Leu Thr Ser Met Pro | | |
| 95 100 105 | | |
| TCC TTC TGG AGC CTG CAG GCC TAC TAC ACC CGT TAC TTC GTA TCG AAT | | 385 |
| Ser Phe Trp Ser Leu Gln Ala Tyr Tyr Thr Arg Tyr Phe Val Ser Asn | | |
| 110 115 120 | | |
| ATC TAT CTG AGC CCT CGC TAC CTG GGG AAT TCA CCC TAT GAC ATT GCC | | 433 |
| Ile Tyr Leu Ser Pro Arg Tyr Leu Gly Asn Ser Pro Tyr Asp Ile Ala | | |
| 125 130 135 | | |
| TTG GTG AAG CTG TCT GCA CCT GTC ACC TAC ACT AAA CAC ATC CAG CCC | | 481 |
| Leu Val Lys Leu Ser Ala Pro Val Thr Tyr Thr Lys His Ile Gln Pro | | |
| 140 145 150 155 | | |
| ATC TGT CTC CAG GCC TCC ACA TTT GAG TTT GAG AAC CGG ACA GAC TGC | | 529 |
| Ile Cys Leu Gln Ala Ser Thr Phe Glu Phe Glu Asn Arg Thr Asp Cys | | |
| 160 165 170 | | |
| TGG GTG ACT GGC TGG GGG TAC ATC AAA GAG GAT GAG GCA CTG CCA TCT | | 577 |
| Trp Val Thr Gly Trp Gly Tyr Ile Lys Glu Asp Glu Ala Leu Pro Ser | | |
| 175 180 185 | | |

```
CCC CAC ACC CTC CAG GAA GTT CAG GTC GCC ATC ATA AAC AAC TCT ATG      625
Pro His Thr Leu Gln Glu Val Gln Val Ala Ile Ile Asn Asn Ser Met
        190                 195                 200

TGC AAC CAC CTC TTC CTC AAG TAC AGT TTC CGC AAG GAC ATC TTT GGA      673
Cys Asn His Leu Phe Leu Lys Tyr Ser Phe Arg Lys Asp Ile Phe Gly
        205                 210                 215

GAC ATG GTT TGT GCT GGC AAT GCC CAA GGC GGG AAG GAT GCC TGC TTC      721
Asp Met Val Cys Ala Gly Asn Ala Gln Gly Gly Lys Asp Ala Cys Phe
220                 225                 230                 235

GGT GAC TCA GGT GGA CCC TTG GCC TGT AAC AAG GAT GGA CTG TGG TAT      769
Gly Asp Ser Gly Gly Pro Leu Ala Cys Asn Lys Asp Gly Leu Trp Tyr
                240                 245                 250

CAG ATT GGA GTC GTG AGC TGG GGA GTG GGC TGT GGT CGG CCC AAT CGG      817
Gln Ile Gly Val Val Ser Trp Gly Val Gly Cys Gly Arg Pro Asn Arg
                255                 260                 265

CCC GGT GTC TAC ACC AAT ATC AGC CAC CAC TTT GAG TGG ATC CAG AAG      865
Pro Gly Val Tyr Thr Asn Ile Ser His His Phe Glu Trp Ile Gln Lys
                270                 275                 280

CTG ATG GCC CAG AGT GGC ATG TCC CAG CCA GAC CCC TCC TGG CCG CTA      913
Leu Met Ala Gln Ser Gly Met Ser Gln Pro Asp Pro Ser Trp Pro Leu
285                 290                 295

CTC TTT TTC CCT CTT CTC TGG GCT CTC CCA CTC CTG GGG CCG GTC TGAGCCTAC968
Leu Phe Phe Pro Leu Leu Trp Ala Leu Pro Leu Leu Gly Pro Val   *
300                 305                 310                 315

TGAGCCCATG CAGCCTGGGG CCACTGCCAA GTCAGGCCCT GGTTCTCTTC TGTCTTGTTT   1028

GGTAATAAAC ACATTCCAGT TGATGCCTTG CAGGGCATTT TTCAAAAAAA AAAAAAAAAA   1088

AAAAAAAAAA AA                                                      1100

(2) INFORMATION FOR SEQ ID NO:6:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Ala Arg Gly Ala Leu Leu Leu Ala Leu Leu Leu Ala Arg Ala
1               5                   10                  15

Gly Leu Arg Lys Pro Glu Ser Gln Glu Ala Ala Pro Leu Ser Gly Pro
                20                  25                  30

Cys Gly Arg Arg Val Ile Thr Ser Arg Ile Val Gly Gly Glu Asp Ala
            35                  40                  45

Glu Leu Gly Arg Trp Pro Trp Gln Gly Ser Leu Arg Leu Trp Asp Ser
        50                  55                  60

His Val Cys Gly Val Ser Leu Leu Ser His Arg Trp Ala Leu Thr Ala
65                  70                  75                  80

Ala His Cys Phe Glu Thr Tyr Ser Asp Leu Ser Asp Pro Ser Gly Trp
                85                  90                  95

Met Val Gln Phe Gly Gln Leu Thr Ser Met Pro Ser Phe Trp Ser Leu
                100                 105                 110

Gln Ala Tyr Tyr Thr Arg Tyr Phe Val Ser Asn Ile Tyr Leu Ser Pro
            115                 120                 125

Arg Tyr Leu Gly Asn Ser Pro Tyr Asp Ile Ala Leu Val Lys Leu Ser
        130                 135                 140

Ala Pro Val Thr Tyr Thr Lys His Ile Gln Pro Ile Cys Leu Gln Ala
```

```
145                 150                 155                 160
Ser Thr Phe Glu Phe Glu Asn Arg Thr Asp Cys Trp Val Thr Gly Trp
                165                 170                 175

Gly Tyr Ile Lys Glu Asp Glu Ala Leu Pro Ser Pro His Thr Leu Gln
                180                 185                 190

Glu Val Gln Val Ala Ile Ile Asn Asn Ser Met Cys Asn His Leu Phe
                195                 200                 205

Leu Lys Tyr Ser Phe Arg Lys Asp Ile Phe Gly Asp Met Val Cys Ala
                210                 215                 220

Gly Asn Ala Gln Gly Gly Lys Asp Ala Cys Phe Gly Asp Ser Gly Gly
225                 230                 235                 240

Pro Leu Ala Cys Asn Lys Asp Gly Leu Trp Tyr Gln Ile Gly Val Val
                245                 250                 255

Ser Trp Gly Val Gly Cys Gly Arg Pro Asn Arg Pro Gly Val Tyr Thr
                260                 265                 270

Asn Ile Ser His His Phe Glu Trp Ile Gln Lys Leu Met Ala Gln Ser
                275                 280                 285

Gly Met Ser Gln Pro Asp Pro Ser Trp Pro Leu Leu Phe Phe Pro Leu
                290                 295                 300

Leu Trp Ala Leu Pro Leu Leu Gly Pro Val
305                 310
```

(2) INFORMATION FOR SEQ ID NO:7:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 24..799

(xi) SEQUENCE DESCRIPTION: SEQ ID NO:7:

```
AGTTCAGATG AATGGGACTG TGA GAA CCA TCT GTG ACC AAA TTG ATA CAG        50
                        Glu Pro Ser Val Thr Lys Leu Ile Gln
                         1               5

GAA CAG GAG AAA GAG CCG CGG TGG CTG ACA TTA CAC TCC AAC TGG GAG      98
Glu Gln Glu Lys Glu Pro Arg Trp Leu Thr Leu His Ser Asn Trp Glu
 10              15                  20                  25

AGC CTC AAT GGG ACC ACT TTA CAT GAA CTT GTA GTA AAT GGG CAG TCT    146
Ser Leu Asn Gly Thr Thr Leu His Glu Leu Val Val Asn Gly Gln Ser
                 30                  35                  40

TGT GAG AGC AGA AGT AAA ATT TCT CTT CTG TGT ACT AAA CAA GAC TGT    194
Cys Glu Ser Arg Ser Lys Ile Ser Leu Leu Cys Thr Lys Gln Asp Cys
                 45                  50                  55

GGG CGC CGC CCT GCT GCC CGA ATG AAC AAA AGG ATC CTT GGA GGT CGG    242
Gly Arg Arg Pro Ala Ala Arg Met Asn Lys Arg Ile Leu Gly Gly Arg
                 60                  65                  70

ACG AGT CGC CCT GGA AGG TGG CCA TGG CAG TGT TCT CTG CAG AGT GAA    290
Thr Ser Arg Pro Gly Arg Trp Pro Trp Gln Cys Ser Leu Gln Ser Glu
     75                  80                  85

CCC AGT GGA CAT ATC TGT GGC TGT GTC CTC ATT GCC AAG AAG TGG GTT    338
Pro Ser Gly His Ile Cys Gly Cys Val Leu Ile Ala Lys Lys Trp Val
 90                  95                 100                 105

GTG ACA GTT GCC CAC TGC TTC GAG GGG AGA GAG AAT GCT GCA GTT TGG    386
Val Thr Val Ala His Cys Phe Glu Gly Arg Glu Asn Ala Ala Val Trp
```

```
                110               115                120
AAA GTG GTG CTT GGC ATC AAC AAT CTA GAC CAT CCA TCA GTG TTC ATG    434
Lys Val Val Leu Gly Ile Asn Asn Leu Asp His Pro Ser Val Phe Met
            125                 130                 135

CAG ACA CGC TTT GTG AGG ACC ATC ATC CTG CAT CCC CGC TAC AGT CGA    482
Gln Thr Arg Phe Val Arg Thr Ile Ile Leu His Pro Arg Tyr Ser Arg
            140                 145                 150

GCA GTG GTG GAC TAT GAC ATC AGC ATC GTT GAG CTG AGT GAA GAC ATC    530
Ala Val Val Asp Tyr Asp Ile Ser Ile Val Glu Leu Ser Glu Asp Ile
        155                 160                 165

AGT GAG ACT GGC TAC GTC CGG CCT GTC TGC TTG CCC AAC CCG GAG CAG    578
Ser Glu Thr Gly Tyr Val Arg Pro Val Cys Leu Pro Asn Pro Glu Gln
170                 175                 180                 185

TGG CTA GAG CCT GAC ACG TAC TGC TAT ATC ACA GGC TGG GGC CAC ATG    626
Trp Leu Glu Pro Asp Thr Tyr Cys Tyr Ile Thr Gly Trp Gly His Met
                190                 195                 200

GGC AAT AAA ATG CCA TTT AAG CTG CAA GAG GGA GAG GTC CGC ATT ATT    674
Gly Asn Lys Met Pro Phe Lys Leu Gln Glu Gly Glu Val Arg Ile Ile
                205                 210                 215

TCT CTG GAA CAT TGT CAG TCC TAC TTT GAC ATG AAG ACC ATC ACC ACT    722
Ser Leu Glu His Cys Gln Ser Tyr Phe Asp Met Lys Thr Ile Thr Thr
            220                 225                 230

CGG ATG ATA TGT GCT GGC TAT GAG TCT GGC ACA GTT GAT TCA TGC ATG    770
Arg Met Ile Cys Ala Gly Tyr Glu Ser Gly Thr Val Asp Ser Cys Met
235                 240                 245

GGT GAC TGG GGC GGT CCG TTG AAT TCT GT                             799
Gly Asp Trp Gly Gly Pro Leu Asn Ser
250                 255

(2) INFORMATION FOR SEQ ID NO:8:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:8:

Glu Pro Ser Val Thr Lys Leu Ile Gln Glu Gln Glu Lys Glu Pro Arg
 1               5                  10                  15

Trp Leu Thr Leu His Ser Asn Trp Glu Ser Leu Asn Gly Thr Thr Leu
                20                  25                  30

His Glu Leu Val Val Asn Gly Gln Ser Cys Glu Ser Arg Ser Lys Ile
            35                  40                  45

Ser Leu Leu Cys Thr Lys Gln Asp Cys Gly Arg Arg Pro Ala Ala Arg
        50                  55                  60

Met Asn Lys Arg Ile Leu Gly Gly Arg Thr Ser Arg Pro Gly Arg Trp
65                  70                  75                  80

Pro Trp Gln Cys Ser Leu Gln Ser Glu Pro Ser Gly His Ile Cys Gly
                85                  90                  95

Cys Val Leu Ile Ala Lys Lys Trp Val Thr Val Ala His Cys Phe
            100                 105                 110

Glu Gly Arg Glu Asn Ala Ala Val Trp Lys Val Val Leu Gly Ile Asn
            115                 120                 125

Asn Leu Asp His Pro Ser Val Phe Met Gln Thr Arg Phe Val Arg Thr
        130                 135                 140

Ile Ile Leu His Pro Arg Tyr Ser Arg Ala Val Val Asp Tyr Asp Ile
145                 150                 155                 160
```

-continued

```
Ser Ile Val Glu Leu Ser Glu Asp Ile Ser Glu Thr Gly Tyr Val Arg
            165                 170                 175

Pro Val Cys Leu Pro Asn Pro Glu Gln Trp Leu Glu Pro Asp Thr Tyr
        180                 185                 190

Cys Tyr Ile Thr Gly Trp Gly His Met Gly Asn Lys Met Pro Phe Lys
        195                 200                 205

Leu Gln Glu Gly Glu Val Arg Ile Ile Ser Leu Glu His Cys Gln Ser
    210                 215                 220

Tyr Phe Asp Met Lys Thr Ile Thr Thr Arg Met Ile Cys Ala Gly Tyr
225                 230                 235                 240

Glu Ser Gly Thr Val Asp Ser Cys Met Gly Asp Trp Gly Gly Pro Leu
            245                 250                 255

Asn Ser (2) INFORMATION FOR SEQ ID NO:9:

(i) SEQUENCE CHARACTERISTICS:
        (A) LENGTH: 2241 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 166..1773

(xi) SEQUENCE DESCRIPTION: SEQ ID NO:9:

ATTTAATACG ACTCACTATA GGGAATTTGG CCCTCGAGGA AGAATTCGGC ACGAGGCTGC     60

GGCGCACTGT GAGGGAGTCG CTGTGATCCG GGGCCCCGAA CCCGACTGGA GCTGAAGCGC    120

AGGCTGCGGG GCGCGGAGTC GGGAGGCCTG AGTGTTCCTT CCAGC ATG TCG GAG        174
                                                Met Ser Glu
                                                  1

GGG GAG TCC CAG ACA GTA CTT AGC AGT GGC TCA GAC CCA AAG GTA GAA      222
Gly Glu Ser Gln Thr Val Leu Ser Ser Gly Ser Asp Pro Lys Val Glu
      5                  10                  15

TCT TCA TCT TCA GCT CCT GGC CTG ACA TCA GTG TCA CCT CCT GTG ACC      270
Ser Ser Ser Ser Ala Pro Gly Leu Thr Ser Val Ser Pro Pro Val Thr
 20                  25                  30                  35

TCC ACA ACC TCA GCT GCT TCC CCA GAG GAA GAA GAA GAA AGT GAA GAT      318
Ser Thr Thr Ser Ala Ala Ser Pro Glu Glu Glu Glu Glu Ser Glu Asp
                 40                  45                  50

GAG TCT GAG ATT TTG GAA GAG TCG CCC TGT GGG CGC TGG CAG AAG AGG      366
Glu Ser Glu Ile Leu Glu Glu Ser Pro Cys Gly Arg Trp Gln Lys Arg
             55                  60                  65

CGA GAA GAG GTG AAT CAA CGG AAT GTA CCA GGT ATT GAC AGT GCA TAC      414
Arg Glu Glu Val Asn Gln Arg Asn Val Pro Gly Ile Asp Ser Ala Tyr
         70                  75                  80

CTG GCC ATG GAT ACA GAG GAA GGT GTA GAG GTT GTG TGG AAT GAG GTA      462
Leu Ala Met Asp Thr Glu Glu Gly Val Glu Val Val Trp Asn Glu Val
     85                  90                  95

CAG TTC TCT GAA CGC AAG AAC TAC AAG CTG CAG GAG GAA AAG GTT TGT      510
Gln Phe Ser Glu Arg Lys Asn Tyr Lys Leu Gln Glu Glu Lys Val Cys
100                 105                 110                 115

GCT GTG TTT GAT AAT TTG ATT CAA TTG GAG CAT CTT AAC ATT GTT AAG      558
Ala Val Phe Asp Asn Leu Ile Gln Leu Glu His Leu Asn Ile Val Lys
                120                 125                 130

TTT CAC AAA TAT TGG GCT GAC ATT AAA GAG AAC AAG GCC AGG GTC ATT      606
```

```
                Phe His Lys Tyr Trp Ala Asp Ile Lys Glu Asn Lys Ala Arg Val Ile
                            135                 140                 145

TTT ATC ACA GGA TAC ATG TCA TCT GGG AGT CTG AAG CAA TTT CTG AAG           654
Phe Ile Thr Gly Tyr Met Ser Ser Gly Ser Leu Lys Gln Phe Leu Lys
            150                 155                 160

AAG ACC CAA AAG AAC CAC CAG ACG ATG AAT GAA AAG GCA TGG AAG CGT           702
Lys Thr Gln Lys Asn His Gln Thr Met Asn Glu Lys Ala Trp Lys Arg
    165                 170                 175

TGG TGC ACA CAA ATC CTC TCT GCC CTA AGC TAC CTG CAC TCC TGT GAC           750
Trp Cys Thr Gln Ile Leu Ser Ala Leu Ser Tyr Leu His Ser Cys Asp
180                 185                 190                 195

CCC CCC ATC ATC CAT GGG AAC CTG ACC TGT GAC ACC ATC TTC ATC CAG           798
Pro Pro Ile Ile His Gly Asn Leu Thr Cys Asp Thr Ile Phe Ile Gln
                200                 205                 210

CAC AAC GGA CTC ATC AAG ATT GGC TCT GTG GCT CCT GAC ACT ATC AAC           846
His Asn Gly Leu Ile Lys Ile Gly Ser Val Ala Pro Asp Thr Ile Asn
            215                 220                 225

AAT CAT GTG AAG ACT TGT CGA GAA GAG CAG AAG AAT CTA CAC TTC TTT           894
Asn His Val Lys Thr Cys Arg Glu Glu Gln Lys Asn Leu His Phe Phe
        230                 235                 240

GCA CCA GAG TAT GGA GAA GTC ACT AAT GTG ACA ACA GCA GTG GAC ATC           942
Ala Pro Glu Tyr Gly Glu Val Thr Asn Val Thr Thr Ala Val Asp Ile
    245                 250                 255

TAC TCC TTT GGC ATG TGT GCA CTG GGG ATG GCA GTG CTG GAG ATT CAG           990
Tyr Ser Phe Gly Met Cys Ala Leu Gly Met Ala Val Leu Glu Ile Gln
260                 265                 270                 275

GGC AAT GGA GAG TCC TCA TAT GTG CCA CAG GAA GCC ATC AGC AGT GCC          1038
Gly Asn Gly Glu Ser Ser Tyr Val Pro Gln Glu Ala Ile Ser Ser Ala
                280                 285                 290

ATC CAG CTT CTA GAA GAC CCA TTA CAG AGG GAG TTC ATT CAA AAG TGC          1086
Ile Gln Leu Leu Glu Asp Pro Leu Gln Arg Glu Phe Ile Gln Lys Cys
            295                 300                 305

CTG CAG TCT GAG CCT GCT CGC AGA CCA ACA GCC AGA GAA CTT CTG TTC          1134
Leu Gln Ser Glu Pro Ala Arg Arg Pro Thr Ala Arg Glu Leu Leu Phe
        310                 315                 320

CAC CCA GCA TTG TTT GAA GTG CCC TCG CTC AAA CTC CTT GCG GCC CAC          1182
His Pro Ala Leu Phe Glu Val Pro Ser Leu Lys Leu Leu Ala Ala His
    325                 330                 335

TGC ATT GTG GGA CAC CAA CAC ATG ATC CCA GAG AAC GCT CTA GAG GAG          1230
Cys Ile Val Gly His Gln His Met Ile Pro Glu Asn Ala Leu Glu Glu
340                 345                 350                 355

ATC ACC AAA AAC ATG GAT ACT AGT GCC GTA CTG GCT GAA ATC CCT GCA          1278
Ile Thr Lys Asn Met Asp Thr Ser Ala Val Leu Ala Glu Ile Pro Ala
                360                 365                 370

GGA CCA GGA AGA GAA CCA GTT CAG ACT TTG TAC TCT CAG TCA CCA GCT          1326
Gly Pro Gly Arg Glu Pro Val Gln Thr Leu Tyr Ser Gln Ser Pro Ala
            375                 380                 385

CTG GAA TTA GAT AAA TTC CTT GAA GAT GTC AGG AAT GGG ATC TAT CCT          1374
Leu Glu Leu Asp Lys Phe Leu Glu Asp Val Arg Asn Gly Ile Tyr Pro
        390                 395                 400

CTG ACA GCC TTT GGG CTG CCT CGG CCC CAG CAG CCA CAG CAG GAG GAG          1422
Leu Thr Ala Phe Gly Leu Pro Arg Pro Gln Gln Pro Gln Gln Glu Glu
    405                 410                 415

GTG ACA TCA CCT GTC GTG CCC CCC TCT GTC AAG ACT CCG ACA CCT GAA          1470
Val Thr Ser Pro Val Val Pro Pro Ser Val Lys Thr Pro Thr Pro Glu
420                 425                 430                 435

CCA GCT GAG GTG GAG ACT CGC AAG GTG GTG CTG ATG CAG TGC AAC ATT          1518
Pro Ala Glu Val Glu Thr Arg Lys Val Val Leu Met Gln Cys Asn Ile
                440                 445                 450
```

```
GAG TCG GTG GAG GAG GGA GTC AAA CAC CAC CTG ACA CTT CTG CTG AAG    1566
Glu Ser Val Glu Glu Gly Val Lys His His Leu Thr Leu Leu Leu Lys
        455                 460                 465

TTG GAG GAC AAA CTG AAC CGG CAC CTG AGC TGT GAC CTG ATG CCA AAT    1614
Leu Glu Asp Lys Leu Asn Arg His Leu Ser Cys Asp Leu Met Pro Asn
            470                 475                 480

GAG AAT ATC CCC GAG TTG GCG GCT GAG CTG GTG CAG CTG GGC TTC ATT    1662
Glu Asn Ile Pro Glu Leu Ala Ala Glu Leu Val Gln Leu Gly Phe Ile
    485                 490                 495

AGT GAG GCT GAC CAG AGC CGG TTG ACT TCT CTG CTA GAA GAG ACC TTG    1710
Ser Glu Ala Asp Gln Ser Arg Leu Thr Ser Leu Leu Glu Glu Thr Leu
500                 505                 510                 515

AAC AAG TTC AAT TTT GCC AGG AAC AGT ACC CTC AAC TCA GCC GCT GTC    1758
Asn Lys Phe Asn Phe Ala Arg Asn Ser Thr Leu Asn Ser Ala Ala Val
                520                 525                 530

ACC GTC TCC TCT TAGAGCTCAC TCGGGCCAGG CCCTGATCTG CGCTGTGGCT        1810
Thr Val Ser Ser
            535

GTCCCTGGAC GTGCTGCAGC CCTCCTGTCC CTTCCCCCCA GTCAGTATTA CCCTGTGAAG  1870

CCCCTTCCCT CCTTTATTAT TCAGGAGGGC TGGGGGGGCT CCCTGGTTCT GAGCATCATC  1930

CTTTCCCCTC CCCTCTCTTC CTCCCCTCTG CACTTTGTTT ACTTGTTTTG CACAGACGTG  1990

GGCCTGGGCC TTCTCAGCAG CCGCCTTCTA GTTGGGGGCT AGTCGCTGAT CTGCCGGCTC  2050

CCGCCCAGCC TGTGTGGAAA GGAGGCCCAC GGGCACTAGG GGAGCCGAAT TCTACAATCC  2110

CGCTGGGGCG GCCGGGGCGG GAGAGAAAGG TGGTGCTGCA GTGGTGGCCC TGGGGGGCCA  2170

TTCGATTCGC CTCAGTTGCT GCTGTAATAA AAGTCTACTT TTTGCTAAAA AAAAAAAAA   2230

AAAAAAAAAA A                                                       2241

(2) INFORMATION FOR SEQ ID NO:10:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO:10:

Met Ser Glu Gly Glu Ser Gln Thr Val Leu Ser Ser Gly Ser Asp Pro
 1               5                  10                  15

Lys Val Glu Ser Ser Ser Ala Pro Gly Leu Thr Ser Val Ser Pro
            20                  25                  30

Pro Val Thr Ser Thr Thr Ser Ala Ala Ser Pro Glu Glu Glu Glu
        35                  40                  45

Ser Glu Asp Glu Ser Glu Ile Leu Glu Glu Ser Pro Cys Gly Arg Trp
    50                  55                  60

Gln Lys Arg Arg Glu Glu Val Asn Gln Arg Asn Val Pro Gly Ile Asp
65                  70                  75                  80

Ser Ala Tyr Leu Ala Met Asp Thr Glu Glu Gly Val Glu Val Val Trp
                85                  90                  95

Asn Glu Val Gln Phe Ser Glu Arg Lys Asn Tyr Lys Leu Gln Glu Glu
            100                 105                 110

Lys Val Cys Ala Val Phe Asp Asn Leu Ile Gln Leu Glu His Leu Asn
        115                 120                 125

Ile Val Lys Phe His Lys Tyr Trp Ala Asp Ile Lys Glu Asn Lys Ala
    130                 135                 140
```

```
Arg Val Ile Phe Ile Thr Gly Tyr Met Ser Gly Ser Leu Lys Gln
145                 150                 155                 160

Phe Leu Lys Lys Thr Gln Lys Asn His Gln Thr Met Asn Glu Lys Ala
            165                 170                 175

Trp Lys Arg Trp Cys Thr Gln Ile Leu Ser Ala Leu Ser Tyr Leu His
            180                 185                 190

Ser Cys Asp Pro Pro Ile Ile His Gly Asn Leu Thr Cys Asp Thr Ile
        195                 200                 205

Phe Ile Gln His Asn Gly Leu Ile Lys Ile Gly Ser Val Ala Pro Asp
        210                 215                 220

Thr Ile Asn Asn His Val Lys Thr Cys Arg Glu Gln Lys Asn Leu
225                 230                 235                 240

His Phe Phe Ala Pro Glu Tyr Gly Glu Val Thr Asn Val Thr Thr Ala
                245                 250                 255

Val Asp Ile Tyr Ser Phe Gly Met Cys Ala Leu Gly Met Ala Val Leu
                260                 265                 270

Glu Ile Gln Gly Asn Gly Glu Ser Ser Tyr Val Pro Gln Glu Ala Ile
                275                 280                 285

Ser Ser Ala Ile Gln Leu Leu Glu Asp Pro Leu Gln Arg Glu Phe Ile
290                 295                 300

Gln Lys Cys Leu Gln Ser Glu Pro Ala Arg Arg Pro Thr Ala Arg Glu
305                 310                 315                 320

Leu Leu Phe His Pro Ala Leu Phe Glu Val Pro Ser Leu Lys Leu Leu
                325                 330                 335

Ala Ala His Cys Ile Val Gly His Gln His Met Ile Pro Glu Asn Ala
            340                 345                 350

Leu Glu Glu Ile Thr Lys Asn Met Asp Thr Ser Ala Val Leu Ala Glu
            355                 360                 365

Ile Pro Ala Gly Pro Gly Arg Glu Pro Val Gln Thr Leu Tyr Ser Gln
370                 375                 380

Ser Pro Ala Leu Glu Leu Asp Lys Phe Leu Glu Asp Val Arg Asn Gly
385                 390                 395                 400

Ile Tyr Pro Leu Thr Ala Phe Gly Leu Pro Arg Pro Gln Gln Pro Gln
                405                 410                 415

Gln Glu Glu Val Thr Ser Pro Val Val Pro Pro Ser Val Lys Thr Pro
                420                 425                 430

Thr Pro Glu Pro Ala Glu Val Glu Thr Arg Lys Val Val Leu Met Gln
                435                 440                 445

Cys Asn Ile Glu Ser Val Glu Glu Gly Val Lys His His Leu Thr Leu
450                 455                 460

Leu Leu Lys Leu Glu Asp Lys Leu Asn Arg His Leu Ser Cys Asp Leu
465                 470                 475                 480

Met Pro Asn Glu Asn Ile Pro Glu Leu Ala Ala Glu Leu Val Gln Leu
                485                 490                 495

Gly Phe Ile Ser Glu Ala Asp Gln Ser Arg Leu Thr Ser Leu Leu Glu
                500                 505                 510

Glu Thr Leu Asn Lys Phe Asn Phe Ala Arg Asn Ser Thr Leu Asn Ser
            515                 520                 525

Ala Ala Val Thr Val Ser Ser
            530                 535

(2) INFORMATION FOR SEQ ID NO:11:

(i) SEQUENCE CHARACTERISTICS:
```

(A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GCACAGTCGA CCAAGCCGGA GTCGCAGAG                                   29

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GCACAAAGCT TGCCAGGAGG GGTCTGGCTG                                  30

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCACAACCAT GGCCAAGCCG GAGTCGCAGG AG                               32

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCACAAGATC TCCAGGAGGG GTCTGGCTG                                   29

(2) INFORMATION FOR SEQ ID NO:15:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:15:

Lys Pro Glu Ser Gln Glu Ala Ala Pro Leu Ser Gly Pro Cys
                 5                  10

(2) INFORMATION FOR SEQ ID NO:16:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:16:

Glu Asp Ala Glu Leu Gly Arg Trp Pro Trp Gln Gly Ser Leu Arg Leu Trp Asp
                 5                  10                  15

Cys (2) INFORMATION FOR SEQ ID NO:17:

(i) SEQUENCE CHARACTERISTICS:
            (A) LENGTH: 17 amino acids
            (B) TYPE: amino acid
            (D) TOPOLOGY: linear (ii) MOLECULE TYPE: protein (xi) SEQUENCE DESCRIPTION: SEQ ID NO:17:

Gly Tyr Ile Lys Glu Asp Glu Ala Leu Pro Ser Pro His Thr Leu Gln Cys
                 5                  10                  15

(2) INFORMATION FOR SEQ ID NO:18:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

GCACAGGTAC CGAGGCCATG GGCGCGCGC                                              29

(2) INFORMATION FOR SEQ ID NO:19:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

GCACATCTAG ATCAGTGGTG GTGGTGGTGG TGGACCGGCC CCAGGAGTGG                       50

(2) INFORMATION FOR SEQ ID NO:20:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

GCACAGCGGC GCGAGGCCA TGGGCGCGCG C                                            31

(2) INFORMATION FOR SEQ ID NO:21:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

GCACAGCGGC CGCTCAGTGG TGGTGGTGGT GGTGCCAGGA GGGGTCTGGC TG                52

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CTGACTTCCA TGCCATCCTT                                                    20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GCTCACGACT CCAATCTGAT                                                    20

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:24:

Arg Ile Val Gly Gly
            5

(2) INFORMATION FOR SEQ ID NO:25:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 2..856

(xi) SEQUENCE DESCRIPTION: SEQ ID NO:25:

```
C GAC CTA TTG TCA GGG CCC TGC GGT CAC AGG ACC ATC CCT TCC CGT          46
  Asp Leu Leu Ser Gly Pro Cys Gly His Arg Thr Ile Pro Ser Arg
   1               5                  10                  15

ATA GTG GGT GGC GAT GAT GCT GAG CTT GGC CGC TGG CCG TGG CAA GGG        94
Ile Val Gly Gly Asp Asp Ala Glu Leu Gly Arg Trp Pro Trp Gln Gly
             20                  25                  30

AGC CTG CGT GTA TGG GGC AAC CAC TTA TGT GGC GCA ACC TTG CTC AAC       142
Ser Leu Arg Val Trp Gly Asn His Leu Cys Gly Ala Thr Leu Leu Asn
         35                  40                  45
```

```
CGC CGC TGG GTG CTT ACA GCT GCC CAC TGC TTC CAA AAG GAT AAC GAT      190
Arg Arg Trp Val Leu Thr Ala Ala His Cys Phe Gln Lys Asp Asn Asp
         50                  55                  60

CCT TTT GAC TGG ACA GTC CAG TTT GGT GAG CTG ACT TCC AGG CCA TCT      238
Pro Phe Asp Trp Thr Val Gln Phe Gly Glu Leu Thr Ser Arg Pro Ser
 65                  70                  75

CTC TGG AAC CTA CAG GCC TAT TCC AAC CGT TAC CAA ATA GAA GAT ATT      286
Leu Trp Asn Leu Gln Ala Tyr Ser Asn Arg Tyr Gln Ile Glu Asp Ile
 80                  85                  90                  95

TTC CTG AGC CCC AAG TAC TCG GAG CAG TAT CCC AAT GAC ATA GCC CTG      334
Phe Leu Ser Pro Lys Tyr Ser Glu Gln Tyr Pro Asn Asp Ile Ala Leu
                100                 105                 110

CTG AAG CTG TCA TCT CCA GTC ACC TAC AAT AAC TTC ATC CAG CCC ATC      382
Leu Lys Leu Ser Ser Pro Val Thr Tyr Asn Asn Phe Ile Gln Pro Ile
            115                 120                 125

TGC CTC CTG AAC TCC ACG TAC AAG TTT GAG AAC CGA ACT GAC TGC TGG      430
Cys Leu Leu Asn Ser Thr Tyr Lys Phe Glu Asn Arg Thr Asp Cys Trp
        130                 135                 140

GTG ACC GGC TGG GGG GCT ATT GGA GAA GAT GAG AGT CTG CCA TCT CCC      478
Val Thr Gly Trp Gly Ala Ile Gly Glu Asp Glu Ser Leu Pro Ser Pro
    145                 150                 155

AAC ACT CTC CAG GAA GTG CAG GTA GCT ATT ATC AAC AAC AGC ATG TGT      526
Asn Thr Leu Gln Glu Val Gln Val Ala Ile Ile Asn Asn Ser Met Cys
160                 165                 170                 175

AAC CAT ATG TAC AAA AAG CCA GAC TTC CGC ACG AAC ATC TGG GGA GAC      574
Asn His Met Tyr Lys Lys Pro Asp Phe Arg Thr Asn Ile Trp Gly Asp
                180                 185                 190

ATG GTT TGC GCT GGC ACT CCT GAA GGT GGC AAG GAT GCC TGC TTT GGT      622
Met Val Cys Ala Gly Thr Pro Glu Gly Gly Lys Asp Ala Cys Phe Gly
            195                 200                 205

GAC TCG GGA GGA CCC TTG GCC TGC GAC CAG GAT ACG GTG TGG TAT CAG      670
Asp Ser Gly Gly Pro Leu Ala Cys Asp Gln Asp Thr Val Trp Tyr Gln
        210                 215                 220

GTT GGA GTT GTG AGC TGG GGA ATA GGC TGT GGT CGC CCC AAT CGC CCT      718
Val Gly Val Val Ser Trp Gly Ile Gly Cys Gly Arg Pro Asn Arg Pro
    225                 230                 235

GGA GTC TAT ACC AAC ATC AGT CAT CAC TAC AAC TGG ATC CAG TCA ACC      766
Gly Val Tyr Thr Asn Ile Ser His His Tyr Asn Trp Ile Gln Ser Thr
240                 245                 250                 255

ATG ATC CGC AAT GGG CTG CTC AGG CCT GAC CCA GTC CCC TTG CTA CTG      814
Met Ile Arg Asn Gly Leu Leu Arg Pro Asp Pro Val Pro Leu Leu Leu
                260                 265                 270

TTT CTT ACT CTG GCC TGG GCT TCC TCT TTG CTG AGG CCT GCC                856
Phe Leu Thr Leu Ala Trp Ala Ser Ser Leu Leu Arg Pro Ala
            275                 280                 285

TGAGCCCACA CGTGTACGTC ACACCTGTGA GGTCAGGGTG TGTCTCTTTT GTATCTTGCT     916

TGCTAATAAA CCTGTTAATA TTTAAAAAAA AAAAAAAAA AAA                        959

(2) INFORMATION FOR SEQ ID NO:26:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO:26:

Asp Leu Leu Ser Gly Pro Cys Gly His Arg Thr Ile Pro Ser Arg Ile
 1               5                  10                  15
```

```
Val Gly Gly Asp Asp Ala Glu Leu Gly Arg Trp Pro Trp Gln Gly Ser
            20                  25                  30

Leu Arg Val Trp Gly Asn His Leu Cys Gly Ala Thr Leu Leu Asn Arg
     35                  40                  45

Arg Trp Val Leu Thr Ala Ala His Cys Phe Gln Lys Asp Asn Asp Pro
 50                  55                  60

Phe Asp Trp Thr Val Gln Phe Gly Glu Leu Thr Ser Arg Pro Ser Leu
 65                  70                  75                  80

Trp Asn Leu Gln Ala Tyr Ser Asn Arg Tyr Gln Ile Glu Asp Ile Phe
                 85                  90                  95

Leu Ser Pro Lys Tyr Ser Glu Gln Tyr Pro Asn Asp Ile Ala Leu Leu
            100                 105                 110

Lys Leu Ser Ser Pro Val Thr Tyr Asn Asn Phe Ile Gln Pro Ile Cys
       115                  120                 125

Leu Leu Asn Ser Thr Tyr Lys Phe Glu Asn Arg Thr Asp Cys Trp Val
 130                 135                 140

Thr Gly Trp Gly Ala Ile Gly Glu Asp Glu Ser Leu Pro Ser Pro Asn
145                 150                 155                 160

Thr Leu Gln Glu Val Gln Val Ala Ile Ile Asn Asn Ser Met Cys Asn
             165                 170                 175

His Met Tyr Lys Lys Pro Asp Phe Arg Thr Asn Ile Trp Gly Asp Met
         180                 185                 190

Val Cys Ala Gly Thr Pro Glu Gly Gly Lys Asp Ala Cys Phe Gly Asp
     195                 200                 205

Ser Gly Gly Pro Leu Ala Cys Asp Gln Asp Thr Val Trp Tyr Gln Val
 210                 215                 220

Gly Val Val Ser Trp Gly Ile Gly Cys Gly Arg Pro Asn Arg Pro Gly
225                 230                 235                 240

Val Tyr Thr Asn Ile Ser His His Tyr Asn Trp Ile Gln Ser Thr Met
             245                 250                 255

Ile Arg Asn Gly Leu Leu Arg Pro Asp Pro Val Pro Leu Leu Leu Phe
         260                 265                 270

Leu Thr Leu Ala Trp Ala Ser Ser Leu Leu Arg Pro Ala
     275                 280                 285

(2) INFORMATION FOR SEQ ID NO:27:

(i) SEQUENCE CHARACTERISTICS:
        (A) LENGTH: 3866 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AGTGAGTCTC CTGCCTCAGC CTCCCAAGTA GCTGGGACTT CAGGTGTGTG CCACCATCCT      60

CAGCTAATTT TTTTTTTTTT TTTTTTTTTG AGAAGGAGTC TTGCTCTGTC GCCCAGGCTG     120

GAGTGCAGTG GCGCGATCTT CCAGGCCCCA CCGGGCCCTC AGGAAGGCCT TGCCTACCTG     180

CTTTAAGGGG ACTCCTGGCT CAGGGCCAGG CCCCTGGTGC TGGAGGAGGT GGTGGGTGGA     240

GGGCAGGGGG CACCAAGCGG GCAGCCAGGA CCCCCGGGCT GCAGACAAGA AAAGGACTGT     300

GGGGTCCACC GGGTCTGGGC CACATCAAGG AATGTGGTTG AAGACCCGCC CTTAGGAGCT     360

GAAAGCCAGG GCGCTACCAG GCCTGAGAGG CCCCAAACAG CCCTTGGGCC TGGTTTGGGA     420

GGATTAAGCT GGAGCTCCCA ACCCGCCCTG CCCCCAGGGG GCGACCCCGG GCCCGGCGCG     480
```

```
AGAGGAGGCA GAGGGGGCGT CAGGCCGCGG GAGAGGAGGC CATGGGCGCG CGCGGGGCGC    540

TGCTGCTGGC GCTGCTGCTG GCTCGGGCTG GACTCAGGAA GCCGGGTGAG CTCGGGGCGC    600

TGCTGGCGGG ATGGGGAGGC GGGGGAGCGG TGGGGAGGAC GGGAGGTGGA GGCCGCGGGG    660

AGTCACTTCT TGTCTCCCGC AGAGTCGCAG GAGGCGGCGC CGTTATCAGG TAGGGCGCCC    720

AGGACGCGCG ATTCCTGCCA GGGCCGTTGG GCCGAGGTGG ACGGGGGCG GTGAGGGGGT     780

AGAGGGGGGC CTTTACTGCT CTCTCGCCCC CGCCCCGGG ATCGAGAACT CTGTTGGCGT     840

GGAAAGTAAC TAACGGACGC TGGAGGGGGA TGGGCGGGCC CTGCAGAGCA CGTGGGAGGA    900

TCTCCAGTGT CACCTACTTC CTGCTGCACA CACGCGAGGG GACCCTGGGT GGGCAAAAAC    960

GTGCTTTCCC GGACGGGGTT GAAGGGGAGA AAGGGAGAGG TCGGGCTTGG GGGGCTGCCT   1020

CCCGCGGCTC AGCAGTTCCT CTGACCATCC GAGGACCATG CGGCCGACGG GTCATCACGT   1080

CGCGCATCGT GGGTGGAGAG GACGCCGAAC TCGGGCGTTG GCCGTGGCAG GGGAGCCTGC   1140

GCCTGTGGGA TTCCCACGTA TGCGGAGTGA GCCTGCTCAG CCACCGCTGG GCACTCACGG   1200

CGGCGCACTG CTTTGAAACG TGAGTGGGGG TGCAACGGA GGGGTGCGGG GACGGGCAGG    1260

AACAGGGCTG GAGGGAGTGC CACCGAACTT TACCTCTGGT CTGATGCCAG ACTTGGGCGT   1320

GAAAGTTGTG CGTGGATGCG GCCTGGTGTT CTCCTGAGCC CCAGGCTGTG CTGCAGCCGG   1380

TTACACCCAC TCCAGTTCCC TTTGGGTCTC CTGGAGGGAA CCCTGTTCAG GTTATTCCAG   1440

AATGTTCTTC CAGAACATTT CCACACACTT TTGGGTATTC TCTCCCTTTT TCTTTCAACC   1500

CAAAGTTCAC CACTGACCAT CCCACCCTCA TCCCCCCTCC TGGTGGACGG TGCGGTACAG   1560

TGTGGGGCAC TGAGCCAAGG CCAGCACCCC CGGGCCGCTG TGTGGACTCC ATCCTGCCAA   1620

TCCCACATTG GCGTGGTGCA TCTCCCCATT CCTCCTTGGG CTGCATGGGG GTGCCCCTGG   1680

AGGCCTTGGC TCAATGCAAG GCTCCTTGGG ACAGCTCTGG GAGGTGACAA GACCCCACCC   1740

TTCTGCTGCA GGAGCAGGTC CTAGGACTTT GGTTGTGGTC TGTCTGGGCT CCTTCATTTC   1800

TGCAGGGGAC CCTGGGTGTT AGCAAGTAGC AGCAACACCA CAGTTTCCCC TCCTGCACTG   1860

GACCCCAGTT GTGCTCAGGT AGCCAGCCCT CCATCCAGGG CCCCTGACTG CTCTCTTCTC   1920

TTCTGCCAGC TATAGTGACC TTAGTGATCC CTCCGGGTGG ATGGTCCAGT TTGGCCAGCT   1980

GACTTCCATG CCATCCTTCT GGAGCCTGCA GGCCTACTAC ACCCGTTACT TCGTATCGAA   2040

TATCTATCTG AGCCCTCGCT ACCTGGGGAA TTCACCCTAT GACATTGCCT TGGTGAAGCT   2100

GTCTGCACCT GTCACCTACA CTAAACACAT CCAGCCCATC TGTCTCCAGG CCTCCACATT   2160

TGAGTTTGAG AACCGGACAG ACTGCTGGGT GACTGGCTGG GGGTACATCA AAGAGGATGA   2220

GGGTGAGGCT GGGGACAGGC GGGTCAGGGA GGAACTGTCT TTGTTCACCT GTTCCCCTGC   2280

ATAGGCACAA TAGCCCCCTG CTTGGTCTGG GGGTGCAGGC TATGCCCCTC TTGCTTGCAG   2340

TCTCTCCTCA CCTGCCAGGG CAGGGACCAA ACACCCAGTT CTCTCCCTTC CAGGGGCTGT   2400

GGGGGCCAGA AGGAGAGTGT GAGAGGGAGG CCAGTTTGGC GCAAGCCTGT GGGTGGTGCG   2460

GTGGTGGAGG GGTTCTGGAG GGCTTGGCGA CATAAACCTC ATACTTGGAT TTATTCCTGC   2520

ATCTTTCCAC CTCCCCCAGT GCTCACCAAT GCCCCAGGCA TCACCAGGTT GCCCCTTCCC   2580

CCAAGGTCTG GCTTTGGATG CTTATGTGAA CACCGTTTTA AGTTGCCTTG GCCCCTTCCT   2640

CGGTTCCTTT TTGGCTGAGG AATCTCTCCA TGGCTGCAGG CAGGGCCATT GTTGCCATTC   2700

TACAGATAGG GAAAGTGCGG CTGGGGGAGC TCTGACAGCT GTCCCTCCCC GGGGCCTTCT   2760

GTGATGCTGC TGAGGGCCTC TGTTGTGCTG GGGTCTGGGT TGGAGCTGGG GGTAATGGAG   2820
```

```
ATGAACCTGC CAGGCACAGT GGGTGCCCCA GGGCCCCCAC CCCCGCAGCC TATGCCATCC    2880

CTCCATAGAG GGGCCTCAGG TTGCTGTCTC TCTCCTTCCC ACTATCGTCC GCACAGCACT    2940

GCCATCTCCC CACACCCTCC AGGAAGTTCA GGTCGCCATC ATAAACAACT CTATGTGCAA    3000

CCACCTCTTC CTCAAGTACA GTTTCCGCAA GGACATCTTT GGAGACATGG TTTGTGCTGG    3060

CAATGCCCAA GGCGGGAAGG ATGCCTGCTT CGTGAGTGTC CTTGCCACCA CTCCCAGCCC    3120

AGGAAAGCAT CCTGTGTCCC TGTGCCTTAT TTGACCCTCA TGCCAACCCC GGGAGGTGGA    3180

GACTGTTGCC CCACTCTGCA GATGCAGAAA CGGAGGCTTG GCTGCTGCCA GGGGGAGGAG    3240

GAGGATGTGC ACCCAGTCTA CCCAGCCCCA TAGCCCTTCC CACTCTCAGC CCCTCCCCTG    3300

CCCCACTCAC TCTGCCCCAG GCTGACCTCA GCCCCGCTGC TCCCCAGGGT GACTCAGGTG    3360

GACCCTTGGC CTGTAACAAG AATGGACTGT GGTATCAGAT GGAGTCGTG AGCTGGGGAG    3420

TGGGCTGTGG TCGGCCCAAT CGGCCCGGTG TCTACACCAA TATCAGCCAC CACTTTGAGT    3480

GGATCCAGAA GCTGATGGCC CAGAGTGGCA TGTCCCAGCC AGACCCCTCC TGGCCGCTAC    3540

TCTTTTTCCC TCTTCTCTGG GCTCTCCCAC TCCTGGGGCC GGTCTGAGCC TACCTGAGCC    3600

CATGCAGCCT GGGGCCACTG CCAAGTCAGG CCCTGGTTCT CTTCTGTCTT GTTTGGTAAT    3660

AAACACATTC CAGTTGATGC CTTGCAGGGC ATTCTTCAAA AGCAGTGGCT TCATGGACAG    3720

CTCATTCTCT CTTGTGCAGA CAGCCTGTCT GTGCCCCTGG CTCACACCCA CATCTGTTCT    3780

GCACCATAGA ACCATCTGGT TATTTCGATC AGAAAGAGAA TTGTGTGTTG CCCAGGCTGG    3840

TCTTGAACGC CTAGGGTGTC TCGATC                                        3866
```

(2) INFORMATION FOR SEQ ID NO:28:

(i) SEQUENCE CHARACTERISTICS:
        (A) LENGTH: 1165 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
CTGAACCGGG TTGTGGGCGG CGAGGACAGC ACTGACAGCG AGTGGCCCTG GATCGTGAGC     60

ATCCAGAAGA ATGGGACCCA CCACTGCGCA GGTTCTCTGC TCACCAGCCG CTGGGTGATC    120

ACTGCTGCCC ACTGTTTCAA GGACAACCTG AACAAACCAT ACCTGTTCTC TGTGCTGCTG    180

GGGGCCTGGC AGCTGGGGAA CCCTGGCTCT CGGTCCCAGA AGGTGGGTGT TGCCTGGGTG    240

GAGCCCCACC CTGTGTATTC CTGGAAGGAA GGTGCCTGTG CAGACATTGC CCTGGTGCGT    300

CTCGAGCGCT CCATACAGTT CTCAGAGCGG GTCCTGCCCA TCTGCCTACC TGATGCCTCT    360

ATCCACCTCC CTCCAAACAC CCACTGCTGG ATCTCAGGCT GGGGGAGCAT CCAAGATGGA    420

GTTCCCTTGC CCCACCCTCA GACCCTGCAG AAGCTGAAGG TTCCTATCAT CGACTCGGAA    480

GTCTGCAGCC ATCTGTACTG GCGGGGAGCA GGACAGGGAC CCATCACTGA GGACATGCTG    540

TGTGCCGGCT ACTTGGAGGG GGAGCGGGAT GCTTGTCTGG GCGACTCCGG GGCCCCCTC    600

ATGTGCCAGG TGGACGGCGC CTGGCTGCTG GCCGGCATCA TCAGCTGGGG CGAGGGCTGT    660

GCCGAGCGCA ACAGGCCCGG GGTCTACATC AGCCTCTCTG CGCACCGCTC CTGGGTGGAG    720

AAGATCGTGC AAGGGGTGCA GCTCCGCGGG CGCGCTCAGG GGGTGGGGC CCTCAGGGCA    780

CCGAGCCAGG GCTCTGGGGC CGCCGCGCGC TCCTAGGGCG CAGCGGGACG CGGGGCTCGG    840

ATCTGAAAGG CGGCCAGATC CACATCTGGA TCTGGATCTG CGGCGGCCTC GGGCGGTTTC    900
```

```
CCCCGCCGTA AATAGGCTCA TCTACCTCTA CCTCTGGGGG CCCGGACGGC TGCTGCGGAA        960

AGGAAACCCC CTCCCCGACC CGCCCGACGG CCTCAGGCCC CGCCTCCAAG GCATCAGGCC       1020

CCGCCCAACG GCCTCATGTC CCCGCCCCCA CGACTTCCGG CCCCGCCCCG GGCCCCAGCG       1080

CTTTTGTGTA TATAAATGTT AATGATTTTT ATAGGTATTT GTAACCCTGC CCACATATCT       1140

TATTTATTCC TCCAATTTCA ATAAA                                             1165
```

(2) INFORMATION FOR SEQ ID NO:29:

(i) SEQUENCE CHARACTERISTICS:
        (A) LENGTH: 933 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
AATGCGGCCA CTCCAAGGAG GCCGGGAGGA TTGTGGGAGG CCAAGACACC CAGGAAGGAC         60

GCTGGCCGTG GCAGGTTGGC CTGTGGTTGA CCTCAGTGGG GCATGTATGT GGGGGCTCCC        120

TCATCCACCC ACGCTGGGTG CTCACAGCCG CCCACTGCTT CCTGAGGTCT GAGGATCCCG        180

GGCTCTACCA TGTTAAAGTC GGAGGGCTGA CACCCTCACT TTCAGAGCCC CACTCGGCCT        240

TGGTGGCTGT GAGGAGGCTC CTGGTCCACT CCTCATACCA TGGGACCACC ACCAGCGGGG        300

ACATTGCCCT GATGGAGCTG GACTCCCCCT TGCAGGCCTC CCAGTTCAGC CCCATCTGCC        360

TCCCAGGACC CCAGACCCCC CTCGCCATTG GGACCGTGTG CTGGGTAAAC GGGCTGGGGG        420

TCCACTCAGG AGAGGCCCTG GCGAGTGTCC TTCAGGAGGT GGCTGTGCCC CTCCTGGACT        480

CGAACATGTG TGAGCTGATG TACCACCTAG AGAGCCCAG CCTGGCTGGC CAGCGCCTCA         540

TCCAGGACGA CATGCTCTGT GCTGGCTCTG TCCAGGGCAA GAAAGACTCC TGCCAGGGTG        600

ACTCCGGGGG GCCGCTGGTC TGCCCCATCA ATGATACGTG GATCCAGGCC GGCATTGTGA        660

GCTGGGGATT CGGCTGTGCC CGGCCTTTCC GGCCTGGTGT CTACACCCAG GTGCTAAGCT        720

ACACAGACTG GATTCAGAGA ACCCTGGCTG AATCTCACTC AGGCATGTCT GGGGCCCGCC        780

CAGGTGCCCC AGGATCCCAC TCAGGCACCT CCAGATCCCA CCCAGTGCTG CTGCTTGAGC        840

TGTTGACCGT ATGCTTGCTT GGGTCCCTGT GAACCATGAG CCATGGAGTC CGGGATCCCC        900

TTTCTGGTAG GATTGATGGA ATCTAATAAT AAA                                    933
```

(2) INFORMATION FOR SEQ ID NO:30:

(i) SEQUENCE CHARACTERISTICS:
        (A) LENGTH: 980 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
CCTGTGGTCG CCCCAGGATG CTGAACCGAA TGGTGGGCGG GCAGGACACG CAGGAGGGCG         60

AGTGGCCCTG GCAAGTCAGC ATCCAGCGCA ACGGAAGCCA CTTCTGCGGG GGCAGCCTCA        120

TCGCGGAGCA GTGGGTCCTG ACGGCTGCGC ACTGCTTCCG CAACACCTCT GAGACGTCCC        180

TGTACCAGGT CCTGCTGGGG GCAAGGCAGC TAGTGCAGCC GGGACCACAC GCTATGTATG        240

CCCGGGTGAG GCAGGTGGAG AGCAACCCCC TGTACCAGGG CACGGCCTCC AGCGCTGACG        300

TGGCCCTGGT GGAGCTGGAG GCACCAGTGC CCTTCACCAA TTACATCCTC CCCGTGTGCC        360
```

```
TGCCTGACCC CTCGGTGATC TTTGAGACGG GCATGAACTG CTGGGTCACT GGCTGGGGCA    420

GCCCCAGTGA GGAAGACCTC CTGCCCGAAC CGCGGATCCT GCAGAAACTC GCTGTGCCCA    480

TCATCGACAC ACCCAAGTGC AACCTGCTCT ACAGCAAAGA CACCGAGTTT GGCTACCAAC    540

CCAAAACCAT CAAGAATGAC ATGCTGTGCG CCGGCTTCGA GGAGGGCAAG AAGGATGCCT    600

GCAAGGGCGA CTCGGGCGGC CCCCTGGTGT GCCTCGTGGG TCAGTCGTGG CTGCAGGCGG    660

GGGTGATCAG CTGGGGTGAG GGCTGTGCCC GCCAGAACCG CCCAGGTGTC TACATCCGTG    720

TCACCGCCCA CCACAACTGG ATCCATCGGA TCATCCCCAA ACTGCAGTTC CAGCCAGCGA    780

GGTTGGGCGG CCAGAAGTGA GACCCCCGGG GCCAGGAGCC CCTTGAGCAG AGCTCTGCAC    840

CCAGCCTGCC CGCCCACACC ATCCTGCTGG TCCTCCCAGC GCTGCTGTTG CACCTGTGAG    900

CCCCACCAGA CTCATTTGTA AATAGCGCTC CTTCCTCCCC TCTCAAATAC CCTTATTTTA    960

TTTATGTTTC TCCCAATAAA                                                980
```